(12) United States Patent
Bendis et al.

(10) Patent No.: US 9,988,599 B2
(45) Date of Patent: Jun. 5, 2018

(54) MODULAR SINGLE-USE KITS AND METHODS FOR PREPARATION OF BIOLOGICAL MATERIAL

(71) Applicant: REVITICELL HOLDINGS, INC, Jacksonville, FL (US)

(72) Inventors: Gregory G. Bendis, Jacksonville, FL (US); Leslie E. Frilling, Fruit Cove, FL (US); John D. Murray, Jacksonville, FL (US); Robert L. Cafferata, Santa Rosa, CA (US); Gary A. Granfield, Jacksonville, FL (US)

(73) Assignee: REVITICELL HOLDINGS, INC., Jacksonville, FL (US)

( * ) Notice: Subject to any disclaimer, the term of this patent is extended or adjusted under 35 U.S.C. 154(b) by 0 days. days.

(21) Appl. No.: 15/505,731

(22) PCT Filed: Aug. 25, 2015

(86) PCT No.: PCT/US2015/046759
§ 371 (c)(1),
(2) Date: Feb. 22, 2017

(87) PCT Pub. No.: WO2016/033089
PCT Pub. Date: Mar. 3, 2016

(65) Prior Publication Data
US 2017/0275582 A1    Sep. 28, 2017

Related U.S. Application Data

(60) Provisional application No. 62/041,196, filed on Aug. 25, 2014.

(51) Int. Cl.
C12M 1/00    (2006.01)
C12M 1/12    (2006.01)
C12M 3/00    (2006.01)

(52) U.S. Cl.
CPC ............ *C12M 45/22* (2013.01); *C12M 21/08* (2013.01); *C12M 23/04* (2013.01); *C12M 23/28* (2013.01); *C12M 23/44* (2013.01)

(58) Field of Classification Search
CPC ...... C12M 45/22; C12M 23/04; C12M 23/28; C12M 23/44; C12M 21/08
See application file for complete search history.

(56) References Cited

U.S. PATENT DOCUMENTS

| 5,707,331 A | 1/1998 | Wells et al. |
| 5,895,346 A | 4/1999 | Wells et al. |

(Continued)

FOREIGN PATENT DOCUMENTS

| WO | WO 2005/011569 | 2/2005 |
| WO | WO 2007/102635 | 9/2007 |

(Continued)

OTHER PUBLICATIONS

Harvest Terumo, Harvest® Adiprep® Adipose Concentration System brochure, Jan. 2014, pp. 1-4.

(Continued)

*Primary Examiner* — Michael L Hobbs
(74) *Attorney, Agent, or Firm* — Saliwanchik, Lloyd & Eisenschenk

(57) ABSTRACT

Disclosed herein are standardized and optimized, modular single-use kits and methods for sterile or non-sterile preparation of biological material, such as cells or tissue, for immediate use, further preparation, or storage. These single-use kits and methods facilitate and improve a healthcare practitioner's ability to prepare biological material for research, diagnostic and therapeutic purposes in a convenient, consistent, repeatable, safe and effective manner.

19 Claims, 10 Drawing Sheets

(56) References Cited

U.S. PATENT DOCUMENTS

| | | |
|---|---|---|
| 6,129,761 A | 10/2000 | Hubbell |
| RE38,730 E | 4/2005 | Wells et al. |
| RE38,757 E | 7/2005 | Wells et al. |
| 7,445,125 B2 | 11/2008 | Ellsworth et al. |
| 7,699,766 B2 | 4/2010 | Ellsworth et al. |
| 7,754,494 B1 | 7/2010 | Verkaart et al. |
| 7,901,672 B2 | 3/2011 | Fraser et al. |
| 7,922,972 B2 | 4/2011 | Ellsworth et al. |
| 8,038,656 B2 | 10/2011 | Lloyd et al. |
| 8,105,580 B2 | 1/2012 | Fraser et al. |
| 8,119,121 B2 | 2/2012 | Fraser et al. |
| 8,152,708 B2 | 4/2012 | Ellsworth et al. |
| 8,348,887 B2 | 1/2013 | Benoit et al. |
| 8,404,198 B2 | 3/2013 | Amshey et al. |
| 9,044,547 B2 | 6/2015 | Tremolada |
| 2008/0050276 A1 | 2/2008 | Bedingham et al. |
| 2011/0162438 A1 | 7/2011 | Tokieda et al. |
| 2014/0186937 A1 | 7/2014 | Smith et al. |
| 2014/0199770 A1 | 7/2014 | Habrich et al. |

FOREIGN PATENT DOCUMENTS

| | | |
|---|---|---|
| WO | WO 2011/145075 | 11/2011 |
| WO | WO 2013/030761 | 3/2013 |
| WO | WO 2013/132192 | 9/2013 |
| WO | WO 2013/181740 | 12/2013 |

OTHER PUBLICATIONS

Güven, S. et al., "Validation of an Automated Procedure to Isolate Human Adipose Tissue-Derived Cells by Using the Sepax® Technology," *Tissue Engineering: Part C*, 2012, vol. 18, No. 8, pp. 575-582.

Medikan International, Inc., "LipoKit II," www.medikanint.com/lipkit.html, 2011.

Alexander, R.W. et al., "Autologous fat grafting: use of closed syringe microcannula system for enhanced autologous structural grafting," *Clinical, Cosmetic and Investigational Dermatology*, 2013, vol. 6, pp. 91-102.

Extended European Search Report, dated Apr. 2018, issued in related European Application No. 15835756.6.

US 9,988,599 B2

MODULAR SINGLE-USE KITS AND METHODS FOR PREPARATION OF BIOLOGICAL MATERIAL

CROSS-REFERENCE TO RELATED APPLICATIONS

The present application is the National Stage of International Application Number PCT/US15/046759 filed Aug. 25, 2015 which claims the benefit of U.S. Provisional Application Ser. No. 62/041,196, filed Aug. 25, 2014, each of which is hereby incorporated by reference herein in its entirety, including any figures, tables, nucleic acid sequences, amino acid sequences, or drawings.

FIELD

This disclosure relates to standardized and optimized, modular single-use kits and methods for sterile or non-sterile preparation of biological material, such as cells or tissue, for immediate use, further preparation, or storage.

BACKGROUND OF THE INVENTION

It is thought that reducing variability in the way healthcare is delivered can help control healthcare costs. Well-defined guidelines can improve reproducibility of care, and can contribute to a standard by which to measure and enhance quality. Increased consistency may also allow healthcare practitioners to be more efficient with their time, space, and personnel. Of course, a degree of variation is unavoidable, since healthcare practitioners must make treatment decisions based on their own knowledge and experience, an ever expanding constellation of complex details, and each individual patient's situation.

Biological products such as proteins and cells can be useful for the prevention, treatment, and/or cure of a disease or condition. These materials are very different from chemically synthesized drugs in that they are derived from living sources, are complex mixtures that may be difficult to fully characterize, and may have increased susceptibility to microbial contamination. Furthermore, while cells and tissues are useful for the repair, reconstruction, replacement or supplementation of a recipient's cells and/or tissues (as the case may be), utilization of such may sometimes be limited by a lack of availability and/or complications such as donor site morbidity, viability and/or compatibility, and/or due to immune system rejection.

Adipose tissue is loose connective tissue composed mostly of adipocytes and the stromal vascular fraction which includes preadipocytes, fibroblasts, vascular endothelial cells and a variety of immune cells. Adipose tissue is derived from preadipocytes and, in the case of white adipose tissue, its main role is to store energy in the form of lipids, although it also cushions and insulates the body. Brown adipose tissue also cushions and insulates the body but has the primary function of generating body heat. Adipose tissue is found in specific locations which are referred to as adipose deposits. Adipose deposits located in different parts of the body have different biochemical profiles. Many small blood vessels run through adipose tissue to provide support needed for its survival. Adipose tissue can be found in the integumentary system which includes the epidermis, dermis and hypodermis. The adipose tissue located just beneath the epidermis and dermis in the hypodermis is commonly referred to as subcutaneous tissue. Adipose tissue found around internal organs is commonly referred to as visceral fat. Visceral fat (also known as abdominal fat or organ fat) is located inside the abdominal cavity and packed in between organs such as the stomach, liver, intestines and kidneys. Intramuscular fat is interspersed in skeletal muscles.

Recently, there has been an increased focus on using adipose tissue as a source for so-called adipose stromal cells ("ASCs") which are progenitor cells that can be used for cell therapy and other therapeutic purposes. There are individuals and entities that have made observations and assertions regarding the therapeutic benefits of ASCs (or any synonyms for such progenitor cells) and the means to achieve such benefits. However, attempts to commercialize the preparation of adipose tissue to access ASCs have been primarily directed at large-scale automated processes or smaller inefficient systems with limited effectiveness. An example of a system that embodies such a large-scale automated processes is that which is disclosed in U.S. Pat. Nos. 7,901,672, 8,105,580, and 8,119,121, the entire contents of each of which are hereby incorporated by reference for all they teach regarding ASCs (and synonyms for such progenitor cells), stem cell therapies, and tissue engineering.

Preparation of adipose tissue occurs after it has been harvested (removed) from a patient by a physician. The harvesting procedure typically involves infiltration of a patient's adipose tissue with a solution (often referred to as tumescent solution) that is typically a mixture of, but not limited to, saline, anesthetic, and epinephrine. A suction-based cannula technique is typically used to harvest adipose tissue and, along with it, much of the tumescent solution. Because this technique produces a mixture of adipose tissue and tumescent solution (which is typically referred to as lipoaspirate), it is necessary for a healthcare practitioner to separate the adipose tissue desired for therapeutic purposes from the lipoaspirate.

Use of adipose tissue for therapeutic purposes is routinely performed by physicians in surgical operating rooms, outpatient facilities, clinics and hospitals throughout the world. However, predictable, consistent, repeatable and effective results are not typically achieved and procedures are not always as safe as they should be. The variety of supplies, equipment, techniques, and procedural steps used to prepare adipose tissue are often arbitrary, varying from patient-to-patient, which contributes to inconsistent outcomes. This variation can even occur within the same clinic, between different healthcare practitioners, and even when such procedures are performed by the same healthcare practitioner.

Primary reasons for the variability and inconsistencies in the current state of the art include the lack of (i) a work area that is set up in an appropriate manner, (ii) proper equipment, (iii) necessary supplies, (iv) safe and adequate consumables, and (v) an organized protocol with standardized procedures and a consistent methodological approach. Often, necessary supplies are not readily available and the various quantities of required consumables are not ordered or inventoried properly. Frequently, an inconsistent variety of supplies are used in various settings with arbitrary protocols that result in an unfortunate variety of patient-to-patient outcomes.

BRIEF SUMMARY OF THE INVENTION

Described herein are standardized and optimized, modular, single-use kits and methods for sterile or non-sterile preparation of biological material (such as cells and tissue) for immediate use, further preparation or storage. The single-use kits disclosed herein comprise at least one single-use component necessary for the preparation of biological material in accordance with a particular method as set forth in the instructions included with each particular type of single-use kit. The single-use kits and methods disclosed herein can be used for sterile preparation of biological material for clinical applications (such as regenerative medicine) and for diagnostic purposes, as well as for sterile or non-sterile research and development purposes. Non-sterile research and development purposes may include, for example, in vitro cellular arrays, tissue arrays and biological assays, as well as high-throughput drug screening.

The single-use kits and methods disclosed herein facilitate and improve a healthcare practitioner's ability to prepare biological material in a convenient, consistent, repeatable, safe, and effective manner. Methods for using the single-use kits are comprised of one or more steps (e.g., a sequence of steps) set forth in the instructions included with the single-use kits. The single-use kits include at least one modular single-use packaging frame that has a top and bottom and one or more levels that accommodate one or more modular single-use trays. Each tray has an identifying label (such as one or more numbers, letters, graphical indicia, or any combination thereof) that corresponds to (correlates with) one or more of the steps of the method set forth in the instructions included with the single-use kit.

In embodiments of the single-use kit disclosed herein where a plurality of trays are disposed within the packaging frame, the trays are sequentially labeled with number(s), letter(s), graphical indicia, or any combination thereof that correspond to (correlate with) one or more of the sequence of steps of the method set forth in the instructions included with the single-use kit. When viewing such embodiments in vertical orientation, the sequentially labeled trays are positioned in ascending or descending order (i.e., top to bottom or bottom to top).

One or more single-use components of the single-use kits disclosed herein are organized in each modular single-use tray. However, components may optionally be organized in other types of packaging units (e.g., boxes or packages that may be comprised of one or more compartments or sections for organizing the components). Single-use components that are required to be sterile in accordance with the instructions included in the single use kit can either be provided in sterile packaging prior to being placed in the trays (and/or other packaging units) or can be terminally sterilized after being placed in the trays (and/or other packaging units).

Modular, single-use packaging frames (and other packaging units) are sub-kits configured in various combinations to form the single-use kits disclosed herein. The sub-kits comprise various combinations of single-use components for various purposes related to the preparation of biological material. Sub-kits that are comprised in the single-use kits disclosed herein are identified in the instructions included with the single use kits with names such as, but not limited to, preparation sub-kit, solutions sub-kit, hydration sub-kit and reagent sub-kit, for example. Various sub-kits in various embodiments of the single-use kits can, for example, be used for the (i) concentration and use of cells or tissue, (ii) identification, isolation and use of nucleated cells, (iii) identification, isolation and use of stem cells, and (iv) identification, isolation, differentiation and use of stem cells.

BRIEF DESCRIPTION OF THE DRAWINGS

FIG. 1A depicts the single-use kit comprising a single packaging frame disposed with four trays and a protective cover that engages with the front of the packaging frame. FIG. 1B depicts the single packaging frame sans trays, and having a secondary interior cavity in the rear portion, which functions as a reservoir for the disposal of liquid biological waste. FIG. 1C depicts a section view of a portion of the single packaging frame with the reservoir.

DETAILED DESCRIPTION OF THE INVENTION

This disclosure generally provides for standardized and optimized, modular single-use kits and methods for sterile or non-sterile preparation of biological material for immediate use, further preparation, or storage, wherein each single-use kit comprises:

(a) at least one modular single-use packaging frame;

(b) at least one modular single-use tray disposed within the modular single-use packaging frame, wherein the tray has an identifying label;

(c) at least one single-use component organized within at least one modular single-use tray; and (d) instructions for use comprising a sequence of steps that set forth a method for using the single-use kit for preparation of biological material, wherein one or more of the steps of the instructions correspond to (correlate with) at least one label of a modular single-use tray.

Figure 1A:
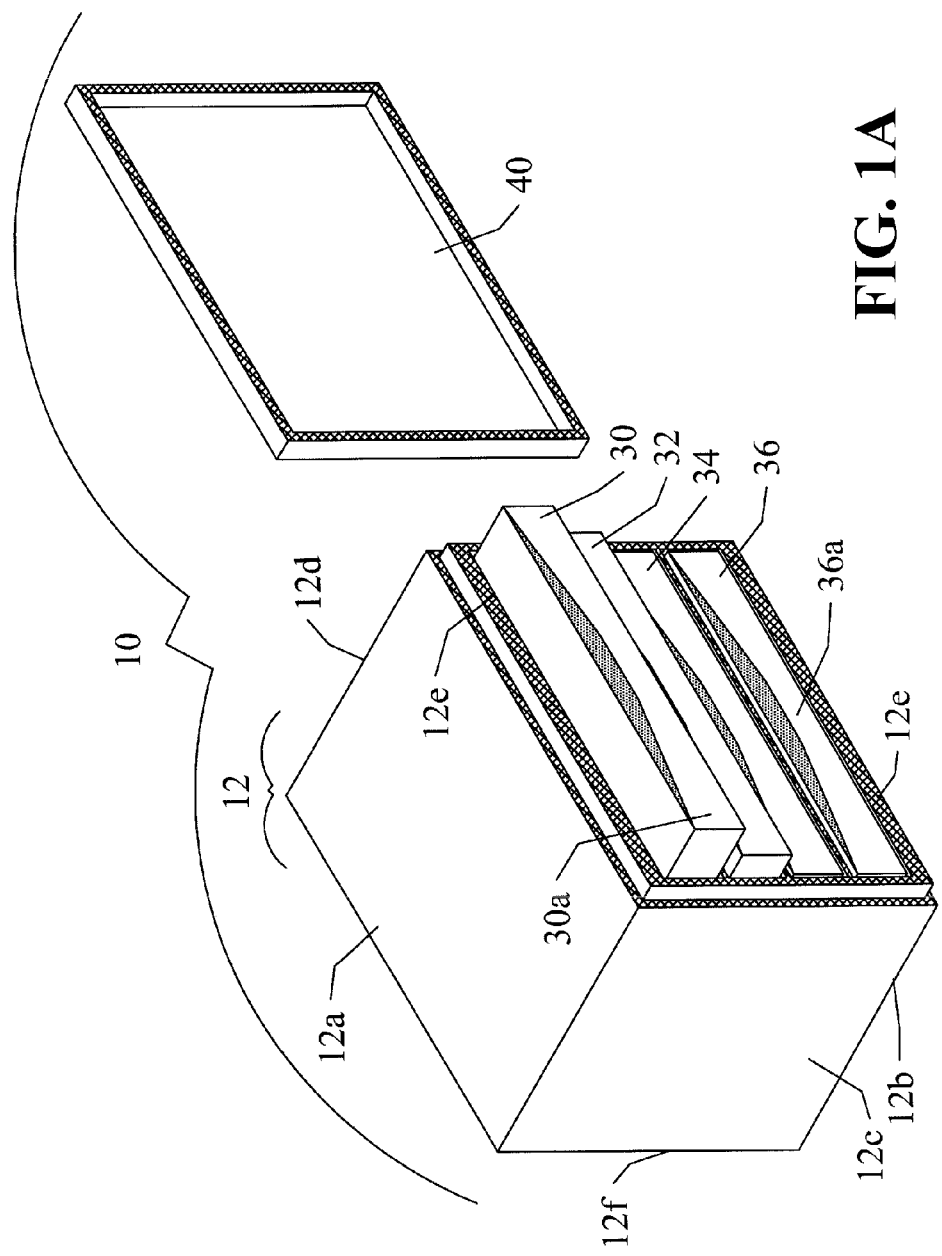
FIGS. 1A to 1C depict an embodiment of the single-use kits disclosed herein.
Figure 1C:
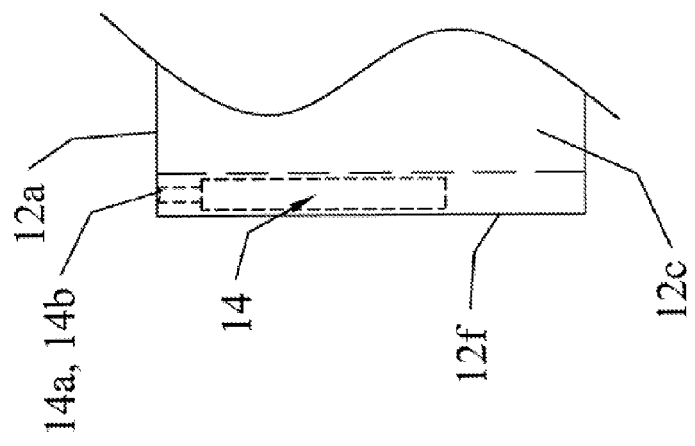
Figure 1B:
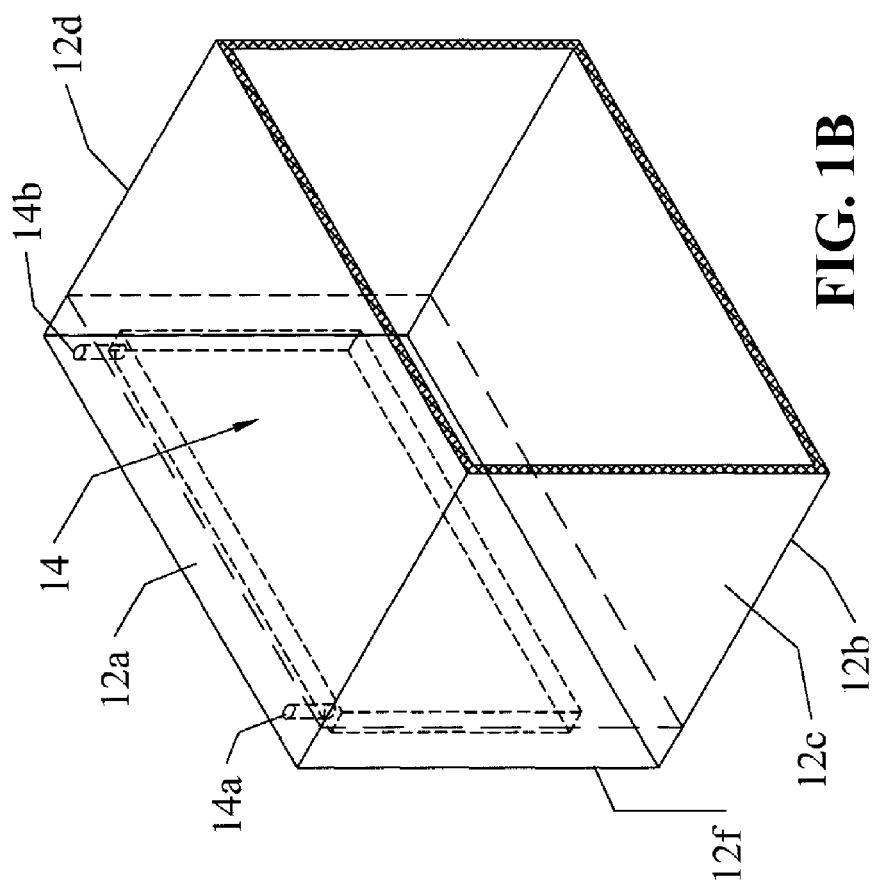
Figure 2:
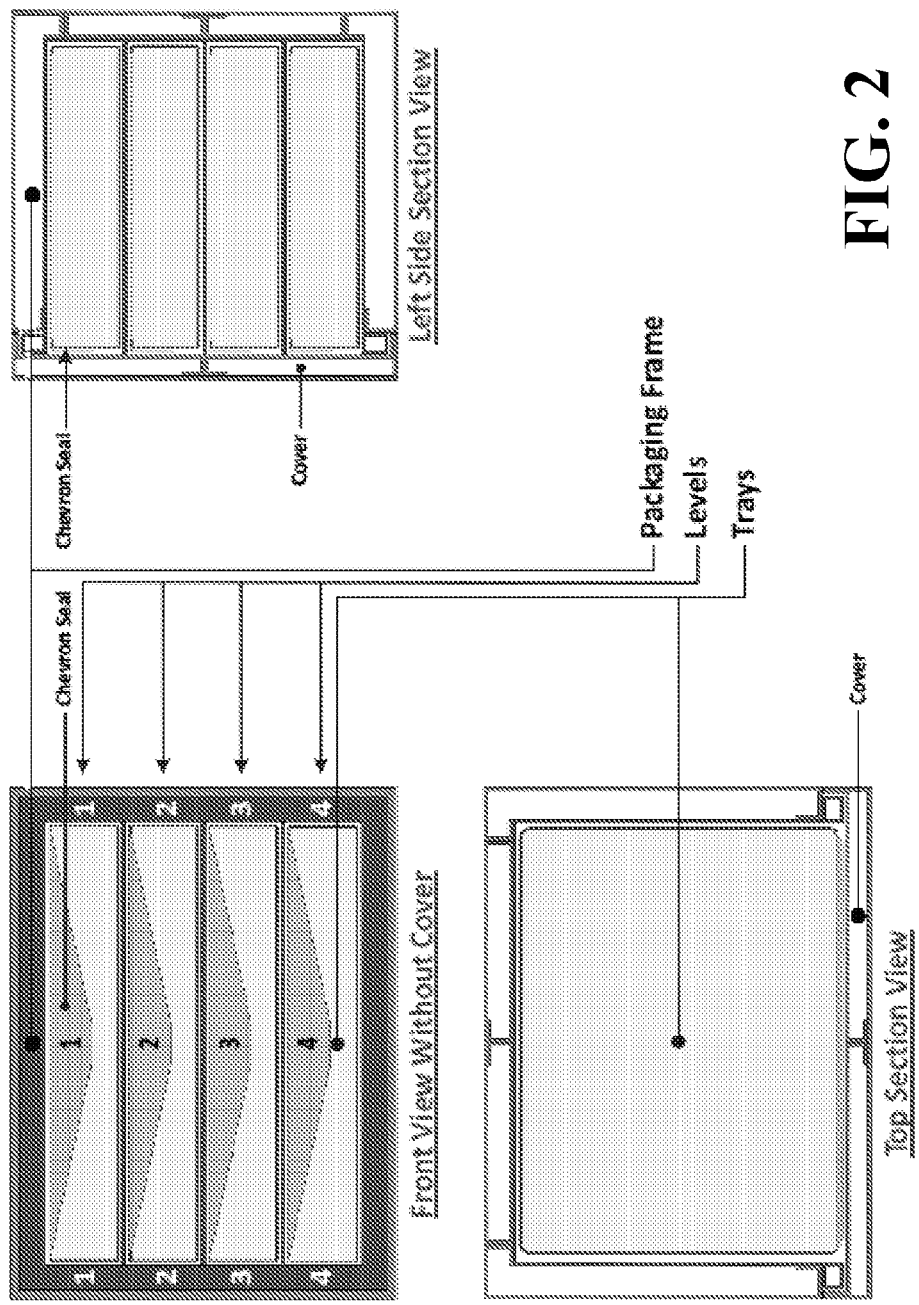
FIG. 2 depicts three views of an embodiment of the single-use kit disclosed herein that comprises a single packaging frame disposed with four trays and a protective cover that engages with the front of the packaging frame, as well as an individual chevron seal on each tray that ensures the sterility of the interior of the tray and the components organized therein. The tab of the chevron seal is positioned on the front of each tray to display the tray's identifying label; however, other tray seals and other modes of tray labeling may be used. The three views include a left side cut-away section view with the protective cover, front view without the protective cover, and top cut-away section view which reveals the tray inside.

Referring to FIG. 1A, the single-use kit disclosed herein (10) includes the modular single-use packaging frame disclosed herein (12), which fundamentally functions as a casing or housing for holding one or more of the modular single-use trays disclosed herein (30, 32, 34, 36). The packaging frame (12) can be virtually any shape, such as a cube, cuboid, cylinder or frustum. The number of sides and their dimensions relative to each other will dictate the overall shape. The packaging frame (12) shown in FIGS. 1A-1C is cuboid. In some embodiments of the single-use kits disclosed herein, the packaging frame (12) has a top (12a), bottom (12b), front portion (12e), two sidewalls (first and second, or left and right) (12c and 12d), and rear portion (12f), each of which may be substantially planar or curved, depending upon the desired shape of the packaging frame (12), and together define an interior or cavity accommodating one or more trays. In such embodiments, the left and right sidewalls (12c and 12d) and back portion (12f) extend from the base to define the interior of the packaging frame (12) and the left and right sidewalls (12c and 12d) are spaced apart from one another on opposite sides of the base and generally extend parallel to one another. In embodiments of the single-use kit disclosed herein where the tray or trays are accessed from the front of the packaging frame (12), the front portion (12e) generally defines an opening from which the tray or trays can movably extend in an outward fashion and the front and rear portions (12e and 12f) and left and right sidewalls (12c and 12d) can be modular portions fastened together in any suitable manner, or may be unitary, for example.

One or more outer portions of the packaging frame (12), such as the rear portion (12f), can include a surface feature (52) such as a protruding surface that can provide leverage to a person's hand and/or fingers and facilitates moving the packaging frame (12) with one hand if needed.

Optionally, in some embodiments of the single-use kits disclosed herein, the kit includes a reservoir (14) for the disposal of liquid biological waste. The reservoir (14) may be fixed within the packaging frame or moveable, may be flexible or rigid, and may be any convenient shape. In some embodiments of the single-use kits disclosed herein, the reservoir (14) is a flexible reservoir (such as a disposable "bio-disposal bag"), which may be stored in a rolled up configuration in a tray (e.g., the first tray), such as the location at (46) in FIG. 8. After the components are removed, the bag unrolls into the tray as the biological waste begins filling the bag. The tray can include a port (44) to accommodate a tube which connects to the bag.

Optionally, in some embodiments of the single-use kits disclosed herein, the packaging frame (12) has a secondary interior cavity (14), shown in FIGS. 1B and 1C which functions as a reservoir for the disposal of liquid biological waste. The secondary cavity is contained within the structure of the packaging frame, within one or more of the rear portion (12f), top (12a), bottom (12b), left sidewall (12c), and/or right sidewall (12d), and the interior of the secondary cavity is accessible by one or more re-sealable ports extending to the exterior of the packaging frame (12). The secondary cavity can be any convenient shape, such as, but not limited to, a rectangle, square, trapezoid, circle, ellipse, oval, or the like. In some embodiments, the secondary cavity (14) is perpendicular to the interior cavity that accommodates the modular single-use trays (30, 32, 34, and 36), and is located inside and adjacent to the rear portion of the packaging frame (12f), and extends from the top (12a) to the bottom (12b) of the packaging frame, or from the top (12a) extending only to the level of the third (34) or fourth (36) modular single-use tray. In some embodiments, the secondary cavity is accessible via two re-sealable ports (14a, 14b) that extend through the rear portion (12f), top (12a), bottom (12b), left sidewall (12c), or right sidewall (12d). For example, one or more ports can extend through the top (12a) as shown in FIGS. 1B and 1C. However, having the one or more ports extending through other walls may help prevent spillage and avoid potential leakage into the trays. For example, a first port (14a) can extend through the left sidewall (12c) and a second port (14b) can extend through the right sidewall (12d), adjacent or near the top (12a). In addition to providing a place to deposit liquid biological waste, one or more of the ports can serve as a vent for the reservoir. Ports can be made re-sealable by various closures such as caps or plugs.

Figure 8:
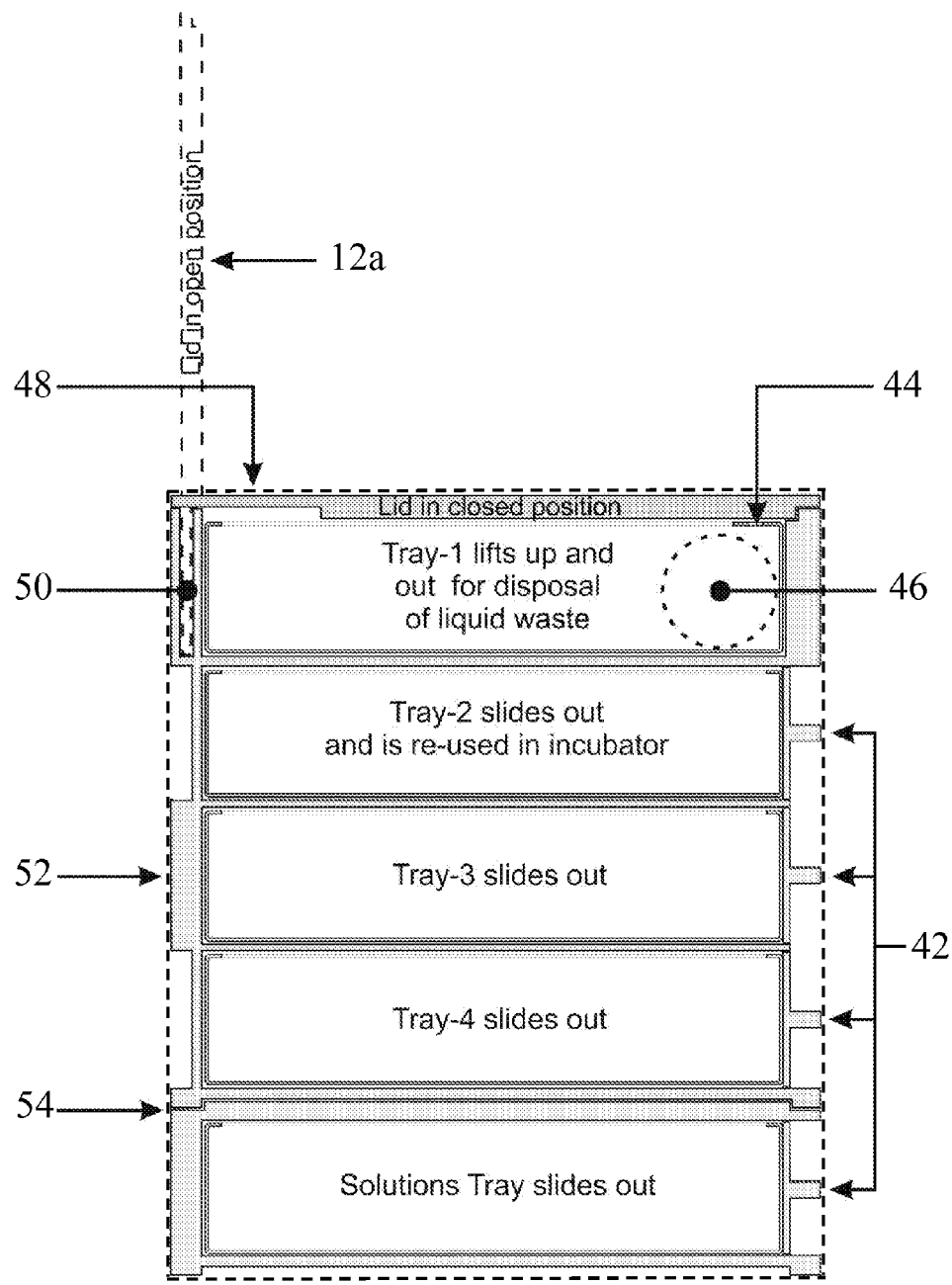
FIG. 8 depicts a cut-away side view of an embodiment of a single-use kit disclosed herein (the back of the kit is at left, and the front of the kit is at right). The dashed line surrounding trays 1-4 represents the sterile barrier of the preparation sub-kit that has been stocked with components, and is then terminally sterilized. The dashed line surrounding the bottom tray represents the sterile barrier of the solutions sub-kit that has been stocked with saline vials in a sterile environment.

Optionally, in some embodiments of the single-use kits disclosed herein, to facilitate the connecting of one packaging frame (12) to another, the top (12a) and bottom (12b) of the packaging frame (12) have complementary features that facilitate stable stacking of the packaging frame (12) with vertically adjacent packaging frames by contacting, and optionally engaging with, complementary features on the adjacent packaging frame. For example, in some embodiments, the bottom (12b) of the first packaging frame (12) has an extending protrusion and the top (12a) of the second packaging frame (12) has a complementary groove or recess for seating of the protrusion or, alternatively, the top of the first packaging frame (12a) has an extending protrusion and the bottom of the second packaging frame (12b) has a complementary groove or recess for seating of the protrusion or, alternatively, the top of both the first and second packaging frame (12a) and bottom of both the first and second packaging frame (12b) have complementary protrusions for the slidably interlocking of the adjacent packaging frame(s) (12). FIG. 8 shows complementary features in the form of an interlocking feature (54) between tray 4 and the solutions tray. The bottom tray can interlock with another tray placed beneath it. Interlocking can be accomplished by simply stacking together (i.e., no adhesive), and can be done at a health care practitioner's office so that the sub-kits are stored and brought into the operating room as a single unit (which should be done with the sterile barrier intact).

The single-use kit disclosed herein as depicted in FIG. 1A includes a protective cover (40) that engages with the front (12a) of the packaging frame (12). The packaging frame (12) may be rigid or semi-rigid, and may be composed of materials such as cardboard or plastic, and may contain other materials such as rubber (e.g., silicone rubber), metal, or a combination of such materials, for example, and preferably of medical grade. Examples of plastics that can be used include thermosetting plastics such as polyurethane, polyester, epoxy resin, phenolic resin, as well as thermoplastics such as polyethylene, polypropylene, and polyvinylchloride. The packaging frame (12) and protective cover (40) may be transparent, translucent, or opaque. Each modular single-use tray of the single-use kits disclosed herein has a number of side walls dictated by the overall shape of the single-use tray. For example, single-use trays having a quadrilateral shape have four sidewalls. Referring to the embodiment in FIG. 1A, each modular single-use tray has (a) four side walls which include (i) a first and second side wall (i.e., left and right sidewalls), (ii) a third sidewall functioning as a front side wall (with the exterior facing out toward the protective cover) referred to in FIG. 1A as (30a) and (36a), and (iii) a fourth sidewall functioning as a rear sidewall and, (b) a bottom (also referred to herein as a base). The side walls and base (together) define the interior of the tray in which one or more single-use components can be organized. Various arrangements may be used to make the trays moveable, such as runners and guides (as with a chest of drawers). Optionally, in embodiments of the single-use kit disclosed herein where packaging frames include two or more trays, the trays can be separated from each other by dividers, which may be planes of materials or rails extending from one side of the packaging frame to the other (from front-to-back and/or from left-to-right). Typically, the dimensions of the trays in a packaging frame will depend, at least in part, upon the number of trays and the components to be contained therein. For many applications, the dimensions of a four-tray packaging frame will be in the range of 9¼" wide×6¾" deep× 6¾" tall, and the dimensions of an individual tray will be in the range of 8" wide×5½" deep×1¼" tall. The trays in a packaging frame may have the same dimensions or different dimensions relative to each other. The front of each tray may appear visually identical or similar to the other trays in the packaging frame, or markedly different. Optionally, the front of each tray is recessed so that the facing surface of the tray front is flush with the edges of the packaging frame (and packaging-frame dividers if present). Trays may be rigid or semi-rigid, and may be composed of materials such as cardboard or plastic, and may contain other materials such as rubber (e.g., silicone rubber), metal, or a combination of such materials, for example, and preferably of medical-grade. Examples of plastics that can be used include thermosetting plastics such as polyurethane, polyester, epoxy resin, phenolic resin, as well as thermoplastics such as polyethylene, polypropylene, and polyvinylchloride. The trays may be transparent, translucent, or opaque.

Each modular single-use tray disclosed herein includes a base, which is generally planar. Sidewalls extend from the base to define the interior of the tray. In square or rectangular single-use trays, first and second sidewalls (i.e., left and right sidewalls) are spaced apart from one another on opposite sides of the base and generally extend parallel to one another. The third and fourth sidewalls (i.e., front and rear sidewalls) extend generally parallel to one another and perpendicular to the first and second sidewalls. The third and fourth sidewalls are at opposite ends of each of the first and second sidewalls. The four sidewalls can be modular portions fastened together in any suitable manner or may be unitary, for example.

The base of the each modular single-use tray disclosed herein has an interior surface on which the single-use components can be organized. The interior surface of the base of the tray may include one or more component outlines drawn or etched thereon to facilitate placement of each component. Optionally, to prevent unintentional movement of the one or more components within the tray (e.g., during transportation of the single-use kit), retention members may be included on the base to secure at least a portion of each component to the base of the tray so that one or more components can be held in an orderly arrangement. In such instance(s), retention members are configured to allow easy access to the components by a healthcare practitioner who uses the single-use kit. Examples of suitable retention members include clamps, elastic material, and wire. Optionally, an insert that rests on the base and has cavities for receiving and retaining at least a portion of one or more components is included in one or more trays or, optionally, the base of one or more trays is molded to achieve such purpose. Optionally, the trays include a pad or mat that rests on the base of the tray (between the component(s) and the base). The pad or mat may have a texture that reduces sliding of the component(s) across the base of the tray.

The modular single-use trays disclosed herein may further include a removable protective cover which may be composed of the same material as the tray sidewalls or of a different material. The protective cover may be transparent, translucent, or opaque. The purpose of the protective cover is to secure single-use component(s) organized within the tray until the cover is opened and to act as a sterile barrier when component(s) are sterile. Preferably, the protective cover is a peel back chevron-type seal and is tamper evident. Examples of suitable materials for the cover include polymer films, foils, or a combination thereof.

One or more surfaces of each modular single-use tray disclosed herein is labeled (with an identifying label) to correspond to one or more steps of the instructions for use of the single-use kit and, optionally, labeling on the modular single-use packaging frame (to indicate the proper location for each respective tray). Such identifying labeling distinguishes one tray in the packaging frame from another and each distinctive label is specifically referenced by one or more steps of the of the method set forth in the instructions included in the single-use kit, thereby correlating each distinctive label with the instructions that set forth a sequence of steps for a particular method to be used with a particular configuration of the single-use kit (e.g., a tissue engineering kit configured for augmentation). Identifying labeling on the trays may comprise one or more letters, numbers, graphical indicia and/or any combination thereof, for example. Identifying labels may be printed, placed upon, molded, carved, etched, stamped, and/or otherwise embossed on one or more of the surfaces of any tray, including the tray cover (if applicable). In some embodiments of the single-use kit disclosed herein, identifying labels on an arrangement of trays presents a healthcare practitioner who uses the single-use kit with the ability to access trays (and thereby components) in the same sequence as the sequence of steps of the method set forth in the instructions for a particular configuration of the single-use kit.

In some embodiments of the single-use kit disclosed herein, the modular single-use packaging frame with protective cover is sealed in a protective wrapping, after modular single-use trays organized with single-use components have been disposed therein. In further embodiments, when sterile preparation is required, the protective wrapping is designed as a sterile barrier and seal that a non-sterile healthcare practitioner can peel back so that a sterile healthcare practitioner can reach in and move the sterile packaging frame to the sterile work-area and/or sterile field. In further exemplified embodiments, the sterile tray(s) can slide partially or fully in and out of the sterile packaging frame so that a sterile healthcare practitioner can access the sterile components organized within the sterile tray(s). For example, the sterile tray(s) may be pulled out like a drawer to extend outwardly from the front of the sterile packaging frame so that a sterile healthcare practitioner can access the interior of the sterile tray(s) and the sterile component(s) organized therein. Each front side wall (face) of the trays can include a pull that keeps the tray in place until needed ((42) in FIG. 8). In other exemplified embodiments, a non-sterile healthcare practitioner can remove the protective wrapping and the protective cover from the packaging frame and either (a) present the packaging frame to a sterile healthcare practitioner (without touching any part of the sterile trays) so that the sterile healthcare practitioner can remove each individual sterile tray for placement in the sterile work-area and/or sterile field or (b) remove individual trays (and the protective cover from each, if applicable) so that the sterile healthcare practitioner can reach in and move each sterile component to the sterile work-area and/or sterile field.

Optionally, the top of the packaging frame (12*a*) may be configured such that it can be lifted (as a lid) similar to a jewelry box, and optionally, removed, as shown in the embodiment of FIG. 8. Solid lines show the top (12*a*) in the closed position, and dashed lines show the top (12*a*) in the open, vertical position. Optionally, the top (12*a*) may be opened and stowed in a vertical position as shown. The top (12*a*) can include a flange (48) that is received and held in place by a slot (50) in the packaging frame (12) (such as in the rear side wall (12*f*)) such that the top (12*a*) may be held in a vertical orientation. The top flange (48) slides into and out of the slot (50) as needed. Quick-reference instructions can be located on the inside of the top (12*a*) so that the instructions are viewable by the user when the top (12*a*) is in an open position. In embodiments in which the top (12*a*) is removable, the first tray under the top (12*a*) may be removable by lifting up and out of the packaging frame (12). In some embodiments, the first tray functions to hold a flexible reservoir (44), such as a disposable bag.

The single-use kits and methods disclosed herein have been developed to reduce the variability and inconsistencies that often result when biological material is prepared without standardized components and a consistent methodological approach. In this context, the term "standardized" refers to the (i) modularity of the single-use kits, packaging frames and trays which makes possible a variety of configurations that conform to the same basic design of the single-use kit and (ii) consistency of the specifications for each single-use component that is identified for a specific purpose in the instructions included with each single-use kit. Such consistency of specifications decreases the potential for any variation that might otherwise result with the use of non-standardized components, with or without corresponding instructions that set forth a particular method for using the components. For purposes of this disclosure, in the context of components, the term "specifications" refers to the physical and functional characteristics applicable to each component but not necessarily the particular manufacturer or part number, for example. The single-use kits and methods disclosed herein have been developed to facilitate the highly standardized, small-scale, personalized, point-of-care preparation of biological material when performed manually by a healthcare practitioner of ordinary skill and competency. As a result, predictable, consistent, repeatable, safe and effective results can be achieved between similarly situation patients when single-use kits, and the included instructions that set forth the method for using each particular type of single-use kit, are used by a variety of healthcare practitioners, even when used at different times and in different places.

Single-use components described in this disclosure may include, but are not limited to, printed material(s), the instructions (which set forth the method of using a particular single-use kit and/or using a particular sub-kit of such particular single use kit), protocol check-list(s), label(s), work-area cover(s), syringe-rack mat(s), bio-disposal bag(s), reusable freezer bag(s), vial(s), syringe(s) with removable plunger rods of various colors, syringe(s) with fixed plunger rods of various colors, syringe(s) with an attached needle, needle(s), transfer-hub(s), vial-to-syringe adapter(s), ampoule-to-syringe adapter(s), liquid(s) or solution(s) in pre-filled vial(s), liquid(s) or solution(s) in pre-filled ampoule(s), liquid(s) or solution(s) in prefilled syringe(s), and reagent(s). Syringes, needles, transfer-hubs, vial-to-syringe adapters, ampoule-to-syringe adapters, vials and/or ampoules may have connections (also referred to as connectors) for transfer of syringe, vial and/or ampoule contents. Such connections (connectors) can be of any known type such as a quick-connect/release connection (e.g., Luer Taper, Luer-Lock™ or Luer-Slip™), a T-connector, a Y-connector, a cross-connector or a custom configuration, for example. In some embodiments of the single-use kits disclosed herein, the connections (connectors) include at least one valve and/or length of tubing.

Vial-to-syringe adapters of the single-use kits disclosed herein facilitate connecting a syringe directly to a vial instead of using a transfer-hub on an ampoule. In some embodiments, the viral-to-syringe adapter is a Clave™ vial-to-syringe adapter (Hospira, Lake Forest, Ill.) or a Vented Vial Adapter™ (Yukon Medical, Research Trial Park, N.C.).

The single-use components described herein can be organized in the modular single-use trays in a spatial arrangement that is consistent with the order in which they are to be used in accordance with the method set forth in the instructions included with the single-use kit. For example, single-use components can be arranged sequentially (e.g., left to right or front to back) in a line, array, or grid such that, for a given single-use component, the single-use component to be used next in accordance with the method set forth in the instructions is arranged in an adjacent position.

In some embodiments of the single-use kits disclosed herein, single-use components have labeling that corresponds to (correlates with) references in the instructions included with the single use kit. For example, labeling on syringes may include any or all of the following Preparation Syringe-1, Preparation Syringe-2, Preparation Syringe-3, Preparation Syringe-4, Preparation Syringes-5, Preparation Syringe-6, Preparation Syringe-7, Preparation Syringe-8, Reagent Syringe-A Reagent Syringe-B, Concentrate Syringe-A, Concentrate Syringe-B, Adipocyte Syringe-Y, and/or Adipocyte Syringes-Z.

Syringes disclosed herein are comprised of a syringe barrel (which is open at the top and restricted at the bottom in the form of a syringe-tip) and a syringe plunger (which is comprised of a plunger seal connected to a plunger rod). Syringes may also include a syringe-tip cap which can seal the syringe-tip when other instruments or components are not attached (e.g., a needle, vial or an ampoule). The plunger seal has a diameter, and is composed of a suitable material(s), to form a slidable seal with the inner surface of the syringe barrel. The plunger seal can be inserted at the top of the syringe barrel and can be pushed inward (toward the syringe-tip) by applying pressure on the plunger rod. As the plunger seal moves along the inner surface of the syringe barrel, the contents contained in the syringe barrel is aspirated through (forced out of) the syringe-tip. In order to fill the syringe barrel, the plunger rod is gently pulled back (away from the syringe-tip) and the plunger seal slides along the inner surface toward the top of (but not out of) the syringe barrel (pulling the plunger seal out of the barrel would break the vacuum and the sterile seal). The syringes may be of various volumes (capacities), depending upon the procedure in which the syringe is utilized. For example, syringes may be as small as 0.5 cc and as large as 50 cc. In some embodiments, the syringe is a 35 cc syringe. In other embodiments, the syringe is a 1 cc syringe.

Unless otherwise indicated herein, the syringes disclosed herein each have a plunger rod that cannot be disconnected from (or reconnected to) the plunger seal as part of the syringe's normal use. However, some embodiments of the single-use kits disclosed herein include syringes that have plunger rods that can be disconnected from (and reconnected to) the plunger seal (for example, with a twisting motion). A syringe having a plunger rod that can be disconnected from (and reconnected to) the plunger seal with a twisting motion is described in U.S. Pat. No. 8,038,656, the entire contents of which, including the structure and operation of the detachable plunger rod syringe, is hereby incorporated herein by reference in its entirety.

Embodiments of the single-use kit described herein that include plunger rods that can be disconnected from the plunger seal prior to centrifugation, for example, make it possible for a reasonably small centrifuge to be used when syringe barrels contain certain biological material to be centrifuged. A syringe barrel is filled by applying backpressure to the syringe rod which causes it to extend farther and farther out of the top of the syringe barrel as it is filled. Whereas most reasonably small centrifuges (such as those with centrifuge slots accommodating 50 cc test tubes) could accommodate the length of the barrel of the syringes disclosed herein, such centrifuges cannot accommodate the length of the syringe when the plunger rod is extended. To remove the plunger rod (so that the syringe barrel could fit in the centrifuge) would break the sterile seal in cases where the plunger rod cannot be disconnected from the plunger seal. A larger centrifuge could be modified to accommodate syringes with extended plunger rods but such would not be efficient and centrifugation may exert undesirable forces on the plunger rods when connected to the plunger seals. Accordingly, the syringe described herein that comprises a plunger rod that can be disconnected from (and reconnected to) a plunger seal makes it possible to use a reasonably small centrifuge, and to maintain the sterility of the syringe barrel contents, by disconnecting the plunger rod before centrifugation and reconnecting it after so that it is possible to continue using the syringe. Using these syringes in this way represent a "closed system" wherein the biological material can be prepared without being exposed to air, so that the viability of the biological material is not compromised (which may occur when some cell types are exposed to air).

The single-use kits disclosed herein may include one or more modular single-use packaging frame(s), each disposed with modular, single-use trays(s) that are organized with single-use component(s). If a single-use kit includes only one packaging frame, then the single-use kit and the packaging frame are one-and-the-same (such is the case in Example 1 and Example 2 below). If a single-use kit includes more than one packaging frame (and/or a packaging frame plus one or more other packages that contain single-use components of the single-use kit), then each packaging frame (and each of such other packaging) is a sub-kit of the single-use kit (such is the case in Example 3 and Example 4 below).

The packaging frames that dispose the trays organized with the components disclosed herein (and other packaging that contains components of the single-use kit disclosed herein) are sealed with tamper-evident wrapping. Optionally, individual trays disposed in a packaging frame may also be sealed with a tamper-evident cover. If the components are sterile, then such components are either provided in sterile packaging prior to being placed in the trays (or other packaging) or are terminally sterilized after being placed in the trays (or other packaging).

In some embodiments of the single-use kits and methods disclosed herein, the single-use kits are intended for sterile preparation of biological materials (e.g., cells, tissue, organs, polynucleotides, genomic DNA, DNA fragments, RNA, proteins, peptides, etc.) for immediate therapeutic use in a human or animal subject, further preparation, or use at some point in the future. In such embodiments, the biological material may be autologous (from the subject) or non-autologous (not from the subject such as allogeneic—from a matched, related or un-related donor, syngeneic—from an identical sibling of the recipient, or xenogeneic—from a species that is different than that of the recipient).

The single-use kits disclosed herein may be produced for various purposes, such as, but not limited to (i) research kits for purposes of clinical studies and other such experimental purposes that may not require the sterile preparation of biological material, (ii) tissue engineering kits for purposes of preparing biological material wherein the included instructions set forth a method for using components for the sterile harvesting, preparation and utilization of biological material such as adipose tissue, for example, (iii) cell preservation kits for purposes of identifying and preserving certain cells for future use, (iv) diagnostic kits for use by healthcare practitioners who need to identify the nature and cause of a particular patient ailment, and/or to determine the effectiveness and/or dosage (or other such parameters) of a certain treatment for a particular patient, (v) stem cell therapy kits for purposes of identifying, isolating and/or differentiating and utilizing (or storing) certain cells for therapeutic purposes (or for further preparation for immediate or future use), and (vi) veterinary kits for purposes of identifying, isolating and/or differentiating and utilizing (or storing) certain cells for therapeutic use in animals (or for further preparation for immediate or future use). The foregoing examples of the types of single-use kits are all within the scope of the single-use kits disclosed herein. Any one or more of the foregoing examples may include embodiments that comprise various versions which may be produced for one or more specific reasons or purposes.

In some embodiments of the single-use kits disclosed herein, the instructions provided in the single-use kits call for the biological material to be adipose tissue. Preparation of adipose tissue is exemplified throughout this disclosure; however, preparation of other cell types and tissues, as well as other biological materials, is an intended use of the single-use kits.

The instructions that set forth the method for using each particular type of single-use kit disclosed herein can take a variety of forms or articles. For example, the printed instructions may be a single sheet of paper folded multiple times, an accordion-style folded instruction pamphlet, or a booklet. Instructions may also be presented in various formats, such as quick reference guides and flow charts.

In some embodiments of the single-use kit disclosed herein, instructions included in the single-use kit may call for, but single-use kits may not include, certain ancillary supplies and equipment to be provided by healthcare practitioners who use the single-use kit and/or by third-parties. Such ancillary supplies and equipment may include, for example (i) harvesting and injection cannula(s), syringe rack(s), bio-disposal rack(s), a centrifuge with carrier, centrifuge carrier inserts with syringe adapters, an incubating rocker, refrigeration and/or freezer unit(s), pre-op cold-block(s), and/or preparation cold-block(s).

Cold-blocks are for use in accordance with the instructions included with the standardized and optimized, modular single-use kits that are used in the sterile or non-sterile preparation of biological material (such as cells or tissue) for immediate use, further preparation, or storage. Cold-blocks are ancillary to the single-use kits (i.e., cold-blocks are typically not provided as a part of a single-use kit).

Cold-blocks are made of a material (such as metal (e.g., aluminum) or stone) that can maintain a cold temperature (i.e., is resistant to heat transfer) for a comparatively longer period of time than other materials (such as a porous, light-weight wood). Each cold-block comprises a solid base having a plurality of holes, wherein each hole is configured to receive and hold a vessel, such as a vial or syringe, in a desired orientation (typically perpendicular to the plane of the base, or at a slight acute angle from the plane of the base), such that the contents of the vessel can be readily accessed and maintained at a cold temperature for a duration longer than in the absence of the cold-block. Cold-blocks are to be autoclaved after each use and placed into a refrigeration unit (in the unopened autoclave bag).

Pre-op cold-blocks are used with the standardized and optimized, modular single-use kits when the included instructions call for a preoperative protocol. The purpose of using a pre-op cold-block is to maintain a cold temperature for hydration vials that are provided in the hydration sub-kit (which is a part of the standardized and optimized, modular single-use kits when the included instructions call for such).

A pre-op cold-block has a plurality of holes (ten, for example) into which the hydration vials of the hydration sub-kit are to be placed in accordance with the instructions included with the single-use kit. The diameter of the holes are slightly larger than the diameter of the hydration vials. The depth of the holes, and the other dimensions of the pre-op cold-block, are dependent upon the material used to produce the pre-op cold-block.

Preparation cold-blocks are used with the standardized and optimized, modular single-use kits at the time of a patient's procedure in accordance with the included instructions. The purpose of using a preparation cold-block is to maintain a cold temperature for Adipocyte Syringes and Concentrate Syringes that are provided in the preparation sub-kit (which is a part of the standardized and optimized, modular single-use kits when the included instructions call for such).

A preparation cold-block has a plurality of holes (four, for example) into which Adipocyte Syringes and Concentrate Syringes are to be placed in accordance with the instructions included with the single-use kit. The diameter of the holes are slightly larger than the diameter of the Adipocyte Syringes and Concentrate Syringes. The depth of the holes and the other dimensions of the preparation cold-block are dependent upon the material used to produce the preparation cold-block.

In further embodiments of the single-use kits disclosed herein, the instructions included with the single-use kits call for centrifugation when the single-use kits include components for such purpose. Generally, centrifugation is performed at room temperature or less, from 30 seconds to one hour at speeds from 50×g to 5,000×g. Representative, non-limiting examples of centrifugation times and speeds include 3 minutes at 800×g, 3 minutes at 1200×g, 5 minutes at 500×g, 7 minutes at 600×g, 10 minutes at 500×g, 15 minutes at 600×g, 5 minutes at 800×g, 7 minutes at 800×g, 5 minutes at 1000×g, 10 minutes at 1000×g, etc. In some embodiments, the centrifugation time and speed is three minutes at 1020×g. Higher or lower speeds and/or longer or shorter centrifugation times and/or different brake level settings may be used and are within the scope of this disclosure.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of the single-use kit disclosed herein (or of any embodiment thereof disclosed herein) can be combined with any and/or all other elements or limitations (individually or in any combination) of the single-use kit of the invention disclosed herein (or of any embodiment thereof disclosed herein); and, any or all of such combinations are contemplated with the scope of the invention disclosed herein without limitation thereto.

Cells, Tissues, and Organs for Therapeutic and Other Uses

A variety of cells, tissues, and organs may be used in conjunction with the single-use kits and methods disclosed herein. The cells can range in plasticity from totipotent to pluripotent, and from pluripotent to multipotent, but are always to be derived from an adult source. Cells may range from precursor or progenitor to those that are highly specialized, such as cells of the central nervous system (e.g., neurons and glia). Cells can be obtained from a variety of sources, including tissue such as adipose tissue, umbilical cord blood, peripheral blood, bone marrow or brain matter, for example. The cells may be primary cells for therapeutic treatments (when prepared with sterile single-use components and methods) or may be cells of cell lines useful for in vitro bioassays based on the cells' responses to drugs or other agents (e.g., for toxicity and efficacy studies), for example. The cells may be genetically modified or not genetically modified.

As will be understood by one of skill in the art, there are over 200 cell types in the human body. Embodiments of the single-use kits and methods disclosed herein can be used in conjunction with any of these cell types for therapeutic or other purposes. For example, any cell arising from the ectoderm, mesoderm, or endoderm germ cell layers can be used. Examples of cell types are provided in Table 1, below. It will be understood by one of skill in the art that the single-use kits disclosed herein are also applicable for veterinary purposes.

TABLE 1

| Examples of Cell Types |
| --- |
| Keratinizing Epithelial Cells |
| keratinocyte of epidermis |
| basal cell of epidermis |
| keratinocyte of fingernails and toenails |
| basal cell of nail bed |
| hair shaft cells |
| medullary |
| cortical |
| cuticular |

TABLE 1-continued

Examples of Cell Types hair-root sheath cells cuticular
of Huxley's layer
of Henle's layer
external
hair matrix cell Cells of Wet Stratified Barrier Epithelia surface epithelial cell of stratified squamous epithelium of cornea
tongue, oral cavity, esophagus, anal canal, distal urethra, vagina
basal cell of these epithelia
cell of urinary epithelium Epithelial Cells Specialized for Exocrine Secretion cells of salivary gland mucous cell
serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution
of mucus and enzymes
cell of seminal vesicle, secreting components of seminal fluid,
including fructose
cell of prostate gland, secreting other components of seminal fluid
cell of bulbourethral gland, secreting mucus
cell of Bartholin's gland, secreting vaginal lubricant
cell of gland of Littre, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung Cells Specialized for Secretion of Hormones cells of anterior pituitary, secreting growth hormone
follicle-stimulating hormone
luteinizing hormone
prolactin
adrenocorticotropic hormone
thyroid-stimulating hormone
cell of intermediate pituitary, secreting melanocyte-stimulating hormone
cells of posterior pituitary, secreting oxytocin
vasopressin
cells of gut and respiratory tract, secreting serotonin
endorphin
somatostatin
gastrin
secretin
cholecystokinin
insulin
glucagons
bombesin
cells of thyroid gland, secreting
thyroid hormone
calcitonin TABLE 1-continued Examples of Cell Types cells of parathyroid gland, secreting parathyroid hormone
oxyphil cell
cells of adrenal gland, secreting epinephrine
norepinephrine
steroid hormones mineralocorticoids
glucocorticoids
cells of gonads, secreting testosterone
estrogen
progesterone
cells of juxtaglomerular apparatus of kidney juxtaglomerular cell
macula densa cell
peripolar cell
mesangial cell Epithelial Absorptive Cells in Gut, Exocrine Glands, and Urogenital Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage
Hepatocyte
fat cells (e.g., adipocyte)

white fat
brown fat
lipocyte of liver
Epithelial Cells Serving Primarily a Barrier Function, Lining the Lung,
Gut, Exocrine Glands, and Urogenital Tract
type I pneumocyte
pancreatic duct cell
non-striated duct cell of sweat gland, salivary gland, mammary gland,
etc.
parietal cell of kidney glomerulus
podocyte of kidney glomerulus
cell of thin segment of loop of Henle
collecting duct cell
duct cell of seminal vesicle, prostate gland, etc.

Epithelial Cells Lining Closed Internal Body Cavities vascular endothelial cells of blood vessels and lymphatics
(e.g., microvascular cell)

fenestrated
continuous
splenic
synovial cell
serosal cell
squamous cell lining perilymphatic space of ear
cells lining endolymphatic space of ear squamous cell
columnar cells of endolymphatic sac with microvilli
without microvilli
"dark" cell
vestibular membrane cell
stria vascularis basal cell
stria vascularis marginal cell
cell of Claudius
cell of Boettcher TABLE 1-continued Examples of Cell Types choroid plexus cell
squamous cell of pia-arachnoid
cells of ciliary epithelium of eye pigmented
nonpigmented
corneal "endothelial" cell Ciliated Cells with Propulsive Function of respiratory tract
of oviduct and of endometrium of uterus
of rete testis and ductulus efferens
of central nervous system Cells Specialized for Secretion of Extracellular Matrix epithelial:

ameloblast
planum semilunatum cell of vestibular apparatus of ear
interdental cell of organ of Corti
nonepithelial:

fibroblasts
pericyte of blood capillary (Rouget cell)
nucleus pulposus cell of intervertebral disc
cementoblast/cementocyte
odontoblast/odontocyte
chondrocytes of hyaline cartilage
of fibrocartilage
of elastic cartilage
osteoblast/osteocyte
osteoprogenitor cell
hyalocyte of vitreous body of eye
stellate cell of perilymphatic space of ear Contractile Cells skeletal muscle cells red
white
intermediate
muscle spindle-nuclear bag
muscle spindle-nuclear chain
satellite cell
heart muscle cells ordinary
nodal
Purkinje fiber
Cardiac valve tissue
smooth muscle cells
myoepithelial cells:

of iris
of exocrine glands

Cells of Blood and Immune System red blood cell (erythrocyte)
Megakaryocyte
Macrophages monocyte
connective tissue macrophage
Langerhan's cell
osteoclast
dendritic cell
microglial cell
Neutrophil
Eosinophil
Basophil
mast cell
plasma cell TABLE 1-continued Examples of Cell Types T lymphocyte helper T cell
suppressor T cell
killer T cell
B lymphocyte IgM
IgG
IgA
IgE
killer cell
stem cells and committed progenitors for the blood and immune system Sensory Transducers Photoreceptors rod
cones blue sensitive
green sensitive
red sensitive
Hearing inner hair cell of organ of Corti
outer hair cell of organ of Corti
acceleration and gravity type I hair cell of vestibular apparatus of ear
type II hair cell of vestibular apparatus of ear
Taste type II taste bud cell
Smell olfactory neuron
basal cell of olfactory epithelium
blood pH carotid body cell type I
type II
Touch Merkel cell of epidermis
primary sensory neurons specialized for touch
Temperature primary sensory neurons specialized for temperature cold sensitive
heat sensitive
Pain primary sensory neurons specialized for pain
configurations and forces in musculoskeletal system proprioceptive primary sensory neurons Autonomic Neurons Cholinergic
Adrenergic
Peptidergic
Supporting Cells of Sense Organs and of Peripheral Neurons
supporting cells of organ of Corti inner pillar cell
outer pillar cell
inner phalangeal cell
outer phalangeal cell
border cell
Hensen cell
supporting cell of vestibular apparatus
supporting cell of taste bud

TABLE 1-continued

Examples of Cell Types supporting cell of olfactory epithelium
Schwann cell
satellite cell
enteric glial cell

Neurons and Glial Cells of Central Nervous System

Neurons
glial cells astrocyte
oligodendrocyte

Lens Cells anterior lens epithelial cell
lens fiber

Pigment Cells

Melanocyte
retinal pigmented epithelial cell
iris pigment epithelial cell

Germ Cells oogonium/oocyte
Spermatocyte
Spermatogonium
blast cells
fertilized ovum

Nurse Cells ovarian follicle cell
Sertoli cell
thymus epithelial cell (e.g., reticular cell)
placental cell Cells and tissues of various types can be administered to alleviate the symptoms of a wide variety of disease states and pathological conditions in various stages of pathological development. For example, cells can be used to treat acute disorders (e.g., stroke or myocardial infarction), and administered acutely, sub-acutely, or in the chronic state. Similarly, cells can be used to treat chronic disorders (e.g., Parkinson's disease, diabetes, or muscular dystrophy), and administered preventatively and/or prophylactically, early in the disease state, in moderate disease states, or in severe disease states. For example, cells can be administered to a target site or sites on or within human or animal subjects in order to replace or compensate for the subject's own damaged, lost, or otherwise dysfunctional cells. The administering of cells can include infusion of the cells into the subject's bloodstream and cells can be administered for cosmetic purposes which may be elective (i.e., discretionary versus a medical necessity). The cells to be administered may be cells of the same cell type as those damaged, lost, or otherwise dysfunctional, or a different cell type.

Cells can be administered to a patient by a physician in an amount determined by the patient's physician to be effective in achieving a desired result such as a therapeutic benefit (i.e., the amount that can effectively treat the pathological condition of a particular patient). For purposes of this disclosure, the terms "treat" or "treatment" include preventing, inhibiting, reducing the occurrence of and/or ameliorating the physiological effects of the pathological condition to be treated. Doses of cells can be determined by one of ordinary skill in the art, with consideration given to such factors as cell survival rate following administration, the number of cells necessary to induce a physiologic response in the normal state, and the species of the subject.

Cells (and tissues composed of cells) can be administered to a subject by any method of delivery appropriate for the procedure, such as intravascularly, intracranially, intracerebrally, intramuscularly, intradermally, intravenously, intraocularly, orally, nasally, topically, or by open surgical procedure, depending upon the anatomical site or sites to which the cells are to be delivered.

Cells can be administered to a subject in isolation or within a pharmaceutical composition comprising the cells and a pharmaceutically acceptable carrier, and can be used for both therapy and diagnostic purposes. As used herein, a pharmaceutically acceptable carrier may be comprised of saline, solvents, dispersion media, coatings, antibacterial and antifungal agents, isotonic agents, and the like, for example. Pharmaceutical compositions can be formulated according to a variety of known methods for preparing pharmaceutically useful compositions. Formulations are described in a number of sources that are well known and readily available to those of ordinary skill in the art; for example, *Remington's Pharmaceutical Science* (Martin E. W., Easton Pa., Mack Publishing Company, 19$^{th}$ ed.). Formulations suitable for parenteral administration, for example, may include aqueous sterile injection solutions (which may contain antioxidants, buffers, bacteriostats, and solutes that render the formulation isotonic with the blood of the intended recipient) and aqueous and non-aqueous sterile suspensions (which may contain suspending agents and thickening agents).

Cells can be administered on or within a variety of carriers that can be formulated as a solid, liquid, semi-solid, or other physical state. For example, genetically modified cells or non-genetically modified cells can be suspended within an injectable hydrogel composition (U.S. Pat. No. 6,129,761) or encapsulated within microparticles (e.g., microcapsules) that are administered to the subject. Carriers are preferably biocompatible and optionally biodegradable. Suitable carriers may include controlled release systems, for example, wherein the cells and/or the biological factors produced by the cells are released from the carrier at the target anatomic site or sites in a controlled-release fashion (in which case the mechanism of release may include degradation of the carrier due to pH conditions, temperature, or endogenous or exogenous enzymes, for example).

Cells can be administered in or on various scaffolds, such as synthetic or biological tissue scaffolds (Griffith G. and Naughton G., Science, 2002, 295:1009-1013; Langer R., *Stem Cell Research News*, Apr. 1, 2002, pp. 2-3). Porous scaffold constructs may be composed of a variety of natural and synthetic matrices, such as biominerals (e.g., calcium phosphate) and polymers (e.g., alginate) that are optionally cross-linked, and serve as a template for cell proliferation and ultimately tissue formation. Three-dimensional control of pore size and morphology, mechanical properties, degradation and resorption kinetics, and surface topography of the scaffold can be optimized for controlling cellular colonization rates and organization within an engineered scaffold/tissue construct. In this way, the morphology and properties of the scaffold can be engineered to provide control of the distribution of bioactive agents (e.g., proteins, peptides, etc.) and cells. In addition to use as vehicles for delivery of the cells, scaffolds can be utilized to grow the cells in vitro. Scaffolds can contain interconnecting networks of pores and facilitate attachment, proliferation, and biosynthesis of cartilaginous matrix components, where desired. A challenge inherent to strategies that deploy synthetic scaffolding to achieve three-dimensionality is the difficulty of creating the geometric attributes of native tissue. One solution to overcome this challenge, for example, is three dimensional (3D) bio-printing which can be used in conjunction with the single-use kits disclosed herein.

The single-use kits and methods disclosed herein make it possible for biological material to be prepared so that cell types can be identified, configured, treated, and/or modulated for research purposes and/or to treat a particular subject. In some embodiments of the single-use kits disclosed herein, one or more specific cell types (which may be human or another mammalian animal) are identified, configured, treated, and/or modulated to facilitate investigation of, or treatment for, a disease or a condition of a particular subject (which may be human or another mammalian type). In further embodiments, one or more specific cell types are derived from two or more distinct subject donors, or from a donor of another mammalian type. In still further embodiments, the subject-specific cells are manipulated in vitro prior to administration, wherein such manipulation includes one or more of expansion, differentiation, directed differentiation, proliferation, exposure to proteins or nucleic acids, incorporation of genetic vectors, incorporation of genetic or non-genetic cell-tracing moieties, de-differentiation (i.e., generation of induced pluripotent stem cells or equivalents), and cryopreservation (or other such methods of cell preservation).

An aspect of the invention concerns a method for sterile or non-sterile preparation of biological material, comprising providing a standardized and optimized, modular, single-use kit disclosed herein, and carrying out the sequence of steps in the printed instructions directing use of the single-use kit.

In some embodiments, the sequence of steps set forth in the instructions are for the sterile preparation of biological material, wherein the sequence of steps comprises:
(1) setting up a sterile work area;
(2) setting up equipment;
(3) centrifuging biological material;
(4) collecting certain portions of the centrifuged biological material to be set aside;
(5) collecting certain portions of the biological material for further preparation;
(6) further preparing certain portions of the biological material (e.g., by using incubation and/or a reagent treatment); and
(7) combining certain portions of the further-prepared biological material with certain portions of the biological material that was set aside.

In some embodiments, the sequence of steps set forth in the instructions are for the sterile harvesting and sterile preparation of biological material, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment); and
(9) combining certain portions of the further-prepared biological material with certain portions of the biological material that was set aside.

In some embodiments, the sequence of steps set forth in the instructions are for the sterile harvesting, sterile preparation, preservation and storage of biological material, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining certain portions of the further-prepared biological material with certain portions of the biological material that was set aside;
(10) preparing the combined biological material for storage; and
(11) packaging and shipping the combined biological material to be stored.

In some embodiments, the sequence of steps set forth in the instructions are for the sterile harvesting and sterile preparation of biological material which is to be further prepared, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining certain portions of the further-prepared biological material with certain portions of the biological material that was set aside;
(10) preparing the combined biological material for further preparation; and
(11) temporarily storing the combined biological material to be further prepared.

In some embodiments, the sequence of steps set forth in the instructions are for sterile harvesting, sterile preparation, and sterile utilization of biological material for non-autologous implantation or other therapeutic use, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;

(8) further preparing certain portions of the biological material (e.g., by using incubation and/or a reagent treatment);

(9) combining of certain portions of the further-prepared biological material with certain portions of the biological material that was set aside; and

(10) temporarily storing the combined biological material to be used in a patient other than the donor patient.

In some embodiments, the sequence of steps set forth in the instructions are for sterile harvesting, sterile preparation, and sterile utilization of biological material for autologous implantation or other therapeutic use, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining of certain portions of the further-prepared biological material with certain portions of the biological material that was set aside; and
(10) using the combined biological material to treat the donor patient.

In some embodiments, the sequence of steps set forth in the instructions are for the non-autologous sterile harvesting, sterile preparation, identification, isolation, and use of nucleated cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate nucleated cells; and
(9) temporarily storing the nucleated cells to be used in a patient other than the donor patient.

In some embodiments, the sequence of steps set forth in the instructions are for the autologous sterile harvesting, sterile preparation, identification, isolation, and use of nucleated cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate nucleated cells; and
(9) using the nucleated cells to treat the donor patient.

In some embodiments, the sequence of steps set forth in the instructions are for the non-autologous sterile harvesting, sterile preparation, identification, isolation, and use of stem cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate stem cells; and
(9) temporarily storing the stem cells to be used in a patient other than the donor patient.

In some embodiments, the sequence of steps set forth in the instructions are for the non-autologous sterile harvesting, sterile preparation, identification, isolation, and use of stem cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate stem cells; and
(9) using the stem cells to treat a patient other than the donor patient.

In some embodiments, the sequence of steps set forth in the instructions are for the non-autologous sterile harvesting, sterile preparation, identification, isolation, differentiation, and use of stem cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify, isolate and differentiate certain stem cells; and
(9) temporarily storing the differentiated stem cells to be used in a patient other than the donor patient.

In some embodiments, the sequence of steps set forth in the instructions are for the autologous sterile harvesting, sterile preparation, identification, isolation, differentiation, and use of stem cells, and wherein the sequence of steps comprises:

(1) setting up a sterile work area;
(2) setting up equipment;
(3) preparing the patient;

(4) harvesting the biological material;

(5) centrifuging biological material (with or without a rinse solution);

(6) collecting certain portions of the biological material for further preparation;

(7) further preparing certain portions of the biological material (e.g., by using incubation and/or a reagent treatment);

(8) analyzing the prepared biological material to identify, isolate and differentiate certain stem cells; and (9) using the differentiated stem cells to treat the donor patient.

In each of the aforementioned embodiments of the methods of the invention, and in embodiments of the methods described in connection with the version 1.0, version 2.0, version 2.0-S, and version 3.0 tissue engineering kits described herein, the methods include setting up a sterile work area, setting up equipment, and preparing the patient. Setting up a sterile work area includes, but is not necessarily limited to:

(a) (i) [Non-sterile healthcare practitioner] opening the preparation sub-kit wrapping (which acts as the sterile barrier for the packaging frame) so that the sterile healthcare practitioner can reach in and move the sterile packaging frame to the sterile field; alternatively, (ii) [Non-sterile healthcare practitioner] opening the preparation sub-kit wrapping and removing the protective cover from the packaging frame so that the sterile healthcare practitioner can reach in and move the sterile trays to the sterile field; alternatively, (iii) [Non-sterile healthcare practitioner] opening the preparation sub-kit wrapping, removing the protective cover from the packaging frame, removing each tray when directed by sterile healthcare practitioner. (Not setting trays on sterile field.) The protective seal is removed from each tray when directed by the sterile healthcare practitioner and either the sterile healthcare practitioner is allowed to reach in and remove sterile components or the contents of the tray are dumped onto the sterile field as directed by the sterile healthcare practitioner. Care is taken not to touch components or any part of the tray protected by the protective seal. Tray P-2 is placed in an incubating rocker when empty and the other trays are disposed of when empty.

The remaining steps are set forth assuming that one of the first two of these three alternatives has been selected.

(b) Remove work-area cover from Tray P-1 and cover work area; then, place contents of Tray P-1 on work-area cover (which is sterile) and dispose of Tray P-1

(c) [Non-sterile healthcare practitioner] open and hold autoclave bags containing harvesting cannula, syringe rack, bio-disposal rack and injection cannula so that sterile healthcare practitioner can remove items for placement on work-area cover and/or sterile field as is appropriate. Syringe-rack mat (from Tray P-1) is to be placed below syringe rack.

(d) Place bio-disposal bag (from Tray P-1) over bio-disposal rack and then place assembly on work-area cover; hand protocol check-list to non-sterile healthcare practitioner for use in a non-sterile area.

(e) [Non-sterile healthcare practitioner] fill in appropriate information on protocol check-list, being sure to include a patient reference number (which does not directly disclose patient identity) that corresponds to patient's file.

Note that bio-disposal bag is only for collection of syringe contents (i.e., liquids) and is to be properly disposed of after each procedure—it is not to be used for any components or other items that could puncture bag.

Setting up equipment includes, but is not necessarily limited to:

(a) [Non-sterile healthcare practitioner] turning on centrifuge power switch (but not starting spinning of carrier), and adjusting the speed and break-force settings if necessary.

(b) [Non-sterile healthcare practitioner] opening autoclave bag(s) containing carrier inserts so that the sterile healthcare practitioner can reach in and place them in a centrifuge carrier.

In some embodiments, setting up equipment further includes:

[Non-sterile healthcare practitioner] turning on the incubating rocker power switch and adjusting temperature and tilt-level settings if necessary.

Preparing the patient includes, but is not necessarily limited to:

(a) identifying harvesting area(s);

(b) preparing harvesting areas(s) using physician-provided sterile preparation;

(c) anesthetizing access site(s) using physician-provided anesthetic;

(d) creating access site(s) by incising skin with physician-provided scalpel; and, if the biological material is adipose, (e) gently infusing patient's subcutaneous adipose tissue via access site(s) by injecting physician-provided solution which contains a mixture of saline, anesthetic and epinephrine.

Single-Use Kits and Methods for Adipose Tissue Preparation

In some embodiments of the single-use kits disclosed herein in which the biological material is adipose tissue, the methods set forth in the instructions included with each particular type of single-use kit involve the use of subcutaneous fat collected from areas of the patient's body where an excess is stored (such as from, but not limited to, the buttocks, hips, thighs and/or waist). In other embodiments, adipose tissue is obtained from other sources such as, for example, by removal and preparation of the falciform ligament in the case of some types of single-use kits for veterinary purposes.

In general, human adipose tissue is removed from a site of subcutaneous fat using a cannula (essentially a very-large gauge needle) and aspirator (a suction device such as a syringe). To access subcutaneous fat, an incision is made and a solution which typically includes saline and lidocaine (referred to as tumescent solution) is then injected to numb and break up the identified fat deposit (epinephrine is often a part of the tumescent solution to constrict blood vessels in order to reduce bleeding). This technique for removing fat is known as liposuction and the fat removed along with the tumescent solution is referred to as lipoaspirate. In the case of liposuction for purposes of harvesting adipose tissue to be prepared using the single-use kits disclosed herein, a syringe is preferably used as the aspirator to remove the adipose tissue with a gentle suction. In the case of lipoplasty, where liposuction is used as a technique to shape the body, ultrasonic probes, water assisted or other vacuum assisted techniques are typically used to aggressively remove and to dispose of adipose tissue.

In some embodiments of the single-use kits disclosed herein, the included instructions that set forth the method for using the single-use kits call for subcutaneous fat to be harvested as a lipoaspirate and then centrifuged for separation into four layers referred to herein as: (i) tissue concentrate which, being the most dense, settles to the bottom layer;

(ii) aqueous solution which is the layer of tumescent solution and other fluids that form the second layer which floats above the tissue concentrate; (iii) parenchyma which is the fatty tissue that forms the third layer and floats above the aqueous solution; and (iv) a small lipid-containing (glycerin) layer that is the least dense, which floats above the parenchyma as the fourth and top-most layer of centrifuged lipoaspirate.

The fatty tissue of parenchyma is primarily comprised of adipocytes. The most viable of these adipocytes settle to the bottom of the parenchyma layer, whereas the least viable or damaged adipocytes rise to the top, just below the glycerin layer. Adipocytes at the bottom of the parenchyma layer survive longer and are more effective for treating a patient, especially when combined with tissue concentrate. Tissue concentrate comprises the stromal vascular fraction, which includes ASCs (adipose stromal cells, which are progenitor cells) that can be used for tissue engineering, cell therapy and other therapeutic purposes. Some embodiments of the single-use kits disclosed herein are referred to as tissue engineering kits which include instructions that set forth methods for preparing adipose tissue to yield tissue concentrate and the most viable adipocytes for physician use in treating patients.

In exemplified embodiments of the single-use kit disclosed herein (such as in Examples 1-4 below), the included instructions set forth steps of a method that is autologous (e.g., using adipose tissue that is used to treat a donor patient). In further exemplified embodiments (such as in Examples 2-4 below), the included instructions set forth methods that call for the incubation of adipose tissue. In still further exemplified embodiments, (such as in Examples 3-4), the included instructions set forth methods that call for rinsing adipose tissue during the first instance of centrifugation.

In exemplified embodiments of the single-use kit disclosed herein (such as in Example 4 below), the included instructions set forth methods that call for an enzymatic digestion step which significantly increases the quantity of tissue concentrate and, accordingly, the number of ASCs that can be recovered (as has been evidenced in a number of studies). Such an enzymatic digestion step involves a portion of the harvested adipose tissue (not to be reintroduced to the patient in its entirety) to be treated (ex vivo) with an enzymatic reagent, then rinsed to remove the enzymatic reagent prior to a select portion of the adipose tissue being set aside for physician use in treating a patient. Enzymatic digestion degrades collagens in the extracellular matrix of adipose tissue with microbial-derived collagenases and, thereby, makes it possible for ASCs to be released.

The single-use kits and methods disclosed herein provide for the sterile transfer of adipose tissue and/or various solutions and/or various enzymatic reagents between two or more syringes as a part of the closed system described above. Adipose tissue so transferred can be in the form of lipoaspirate, tissue concentrate, parenchyma, aqueous solution and/or glycerin and solutions so transferred can include, but are not limited to, sterile water, saline, phosphate buffered saline and/or an enzymatic reagent suspended in any of the foregoing solutions. Generally, enzymatic reagents used to aid in the digestion of parenchyma are microbial-derived and include, but are not limited to collagenases, proteases, hyaluronidase, lipases and DNAases (non-limiting examples of proteases may include dipases, elastases, trypsin and/or papain). Specific enzyme reagents that are suitable for such digestion include, but are not limited to, collagenases and/or recombinant collagenases such as LIBERASE® (a registered trademark of Roche Diagnostics Operations, Inc. Corporation, Indianapolis, Ind.) and XIAFLEX® (a registered trademark of Auxilium US Holdings, LLC Wilmington, Del.).

Some embodiments of the single-use kits disclosed herein include an enzymatic reagent in a lyophilized form and a hydrating agent for reconstituting the enzymatic reagent (such as sterile water, for example). In further embodiments, a phosphate buffered solution, Lactated Ringer's Solution, or other such buffered solution, for example, is included in order to prepare a working solution of the enzymatic reagent. In still further embodiments, a solution such as sterile saline, for example, is included for purposes of rinsing adipose tissue after treating it with the enzymatic reagent.

Some embodiments of the single-use kits disclosed herein include instructions that set forth methods for preparing adipose tissue to yield tissue concentrate to be stored or further prepared for immediate or future use. Embodiments of single-use kits wherein tissue concentrate (or certain cells thereof) are preserved for storage are referred to herein as cell preservation kits. Embodiments of single-use kits wherein tissue concentrate is further prepared for use of certain cells thereof is referred to herein as stem cell therapy kits when used for humans and veterinary kits when used for animals.

In some embodiments of the single-use kits disclosed herein, the included instructions set forth steps of a method which includes a preoperative protocol that is to be conducted prior to the time of a patient's procedure. In further embodiments, the preoperative protocol includes steps for the reconstitution (e.g., hydration) of a lyophilized enzymatic reagent and the distribution of the resulting reconstituted reagent into storage vials. In still further embodiments, a reagent sub-kit and a hydration sub-kit are used to conduct the preoperative protocol. In exemplified embodiments, (a) the reagent sub-kit is a box (i.e., not a packaging frame but another type of package) that comprises canisters and each canister contains a vial within which there is an enzymatic reagent blend that is sterile, GMP-rated and in a lyophilized form and (b) the hydration sub-kit is a packaging frame of the single-use kit disclosed herein disposed with two trays wherein (i) the first tray is organized with instructions for conducting the preoperative protocol, a work-area cover, a reusable freezer bag, syringes with needle attached, a syringe prefilled with sterile water, and a syringe needle and (ii) the second tray is organized with storage vials with sterile interiors and protective caps. Other embodiments include additional and/or other sub-kits and/or components and instructions that set forth various methods for conducting the preoperative protocol.

In some embodiments of the single-use kits disclosed herein, the included instructions set forth steps of a method which includes an operative protocol that is to be conducted at the time of a patient's procedure. In further embodiments, the operative protocol includes steps divided into phases for the harvesting, preparation and utilization of adipose tissue. In exemplified embodiments (as is the case in Examples 1-4 below), the operative protocol includes four distinct phases: (i) the set-up phase which comprises laying out sterile, single-use components and configuring equipment which is ancillary to the operative protocol, (ii) the harvesting phase which comprises removing a patient's adipose tissue in the form of lipoaspirate (i.e., adipose tissue with a solution such as saline, lidocaine and epinephrine), (iii) the preparation phase which comprises preparing adipose tissue for physician use, and (iv) the utilization phase which comprises a physician's use of the prepared adipose tissue (or parts thereof, including various cell types) for treating a patient. Other embodiments include additional and/or other sub-kits and/or components and/or instructions that set forth various methods for conducting the operative protocol (including that for filtration affinity chromatography, for example).

In some embodiments of the single-use kits disclosed herein, the included instructions set forth steps of methods that require use of a preparation sub-kit to conduct the operative protocol. In exemplified embodiments (such as Examples 1-4 below) the preparation sub-kit is a packaging frame of the single-use kit disclosed herein and (a) the first tray of the packaging frame is organized with instructions for conducting the operative protocol, a protocol check-off list, a work-area cover, a syringe-rack mat, a bio-disposal bag, transfer-hubs, and/or vial-to-syringe adapters and (b) other trays of the packaging frame are organized with needle(s), syringe(s) with color-coded plunger rod that can be disconnected and reconnected to the plunger seals, syringe(s) with color-coded plunger rod that cannot be disconnected.

In some embodiments of the single-use kits disclosed herein, the included instructions set forth steps of methods that require use of a reservoir as part of the kit for the disposal of liquid biological waste. The reservoir may be fixed within the packaging frame or moveable, and may be flexible or rigid. In some embodiments of the single-use kits disclosed herein, the included instructions set forth steps of methods that require use of an interior cavity of the packaging frame (which acts as a reservoir) for the disposal of liquid biological waste. In some embodiments of the single-use kits disclosed herein, the included instructions set forth steps of methods that require the use of a flexible reservoir (a bag), which may be stored in a rolled up configuration in a tray (e.g., the first tray), such as the location at (46) in FIG. 8. After the components are removed, the bag unrolls into the tray as the biological waste begins filling the bag.

In some embodiments of the single-use kits disclosed herein, the included instructions set forth steps of methods that require use of a preparation sub-kit and a solutions sub-kit to conduct the operative protocol. In exemplified embodiments (such as Examples 3-4 below) the solutions sub-kit is a package (i.e., not a packaging frame but another type of package) that comprises vials of sterile saline.

In some embodiments of the single-use kits disclosed herein, the included instructions set forth steps of methods that require use of one or more storage vials of the reconstituted enzymatic reagent (prepared and stored as a part of the preoperative protocol) to conduct the operative protocol. In exemplified embodiments (such as Example 4 below), the solutions sub-kit disclosed herein includes (a) vials of a buffered solution for bringing the reconstituted enzymatic reagent to a working solution and (b) vials of sterile saline for rinsing adipose tissue after having been treated with the enzymatic reagent.

In further embodiments of the single-use kits disclosed herein, certain combinations of sub-kits, trays and components may be used for tissue engineering, in which case the single-use kit is referred to as a tissue engineering kit. For example, plastic surgeons and dermatologists can use a tissue engineering kit configured for augmentation for purposes of preparing adipose tissue for facial augmentation.

Version 1.0 Tissue Engineering Kit

One exemplified embodiment of the single-use kit disclosed herein is referred to as a version 1.0 tissue engineering kit which, when configured for volume augmentation, includes a sterile three-tray preparation sub-kit organized with sterile components including instructions that set forth a method for conducting an operative protocol which includes the centrifugation of lipoaspirate and the preparation of adipose tissue in order to make tissue concentrate and the most viable adipocytes available for physician use in treating a patient.

To prepare such a blend of tissue concentrate and adipocytes, after centrifugation of lipoaspirate and recovery of tissue concentrate and parenchyma, a portion (or portions) of the tissue concentrate is (are) mixed with a portion (or portions) of the parenchyma (which contain the most viable adipocytes). An example of a version 1.0 tissue engineering kit configured for augmentation is illustrated in the first column of FIG. 3 and the first column of FIG. 4 and an example that sets forth the components of, and the method for using, the version 1.0 tissue engineering kit configured for augmentation is set forth in Example 1. All or any portion of the method described in Example 1 may be provided in the printed instructions included with such an embodiment of the version 1.0 tissue engineering kit.

In some embodiments, the sequence of steps comprises:
(1) setting up a sterile work area;
(2) setting up equipment;
(3) preparing the patient;
(4) harvesting adipose tissue from the patient's access site or sites;
(5) centrifuging harvested adipose tissue;
(6) transferring post-centrifugation layers;
(7) combining tissue concentrate and adipocytes of transferred layers; and
(8) utilizing combined tissue concentrate and adipocytes.

Version 2.0 Tissue Engineering Kit

Another exemplified embodiment of the single-use kit disclosed herein is referred to as a version 2.0 tissue engineering kit which, when configured for volume augmentation, includes a four-tray preparation sub-kit organized with sterile components including instructions that set forth a method for conducting an operative protocol which includes the centrifugation of lipoaspirate and the preparation of adipose tissue with an incubation procedure in order to make tissue concentrate and the most viable adipocytes available for physician use in treating a patient. (The addition of the incubation procedure, as compared to the method for using a version 1.0 tissue engineering kit, produces a comparatively larger quantity of tissue concentrate.)

To prepare such a blend of tissue concentrate and adipocytes, after the centrifugation of lipoaspirate and recovery of tissue concentrate and parenchyma, (i) a portion (or portions) of the parenchyma (which contain the most viable adipocytes) is (are) set aside as reserved parenchyma and (ii) another portion (or portions) of the parenchyma is (are) incubated in a third-party incubating rocker at a temperature, tilt angle, speed level and for a time to facilitate digestion of the adipose tissue by endogenous enzymes in the adipose tissue (without addition of exogenous enzymes). After the foregoing procedure, the incubated parenchyma and tissue concentrate are centrifuged and a second quantity of tissue concentrate is recovered. The recovered second quantity of tissue concentrate is then mixed with the reserved parenchyma. An example of a version 2.0 tissue engineering kit configured for augmentation is illustrated in the second column of FIG. 3 and the second column of FIG. 4 and an example that sets forth the components of, and the method for using the version 2.0 tissue engineering kit configured for augmentation is set forth in Example 2. All or any portion of the method described in Example 2 may be provided in the printed instructions included with such an embodiment of the 2.0 tissue engineering kit.

In some embodiments, the sequence of steps comprises:
(1) setting up a sterile work area;
(2) setting up equipment;
(3) preparing the patient;
(4) harvesting adipose tissue from the patient's access site or sites;
(5) centrifuging harvested adipose tissue;
(6) transferring post-centrifugation layers;
(7) setting aside adipocytes for utilization;
(8) combining parenchyma and tissue concentrate;
(9) incubating parenchyma and tissue concentrate;
(10) centrifuging the incubated parenchyma and tissue concentrate;
(11) combining tissue concentrate layer with set-aside adipocytes; and
(12) utilizing combined tissue concentrate and adipocytes.

Version 2.0-S Tissue Engineering Kit

Another exemplified embodiment of the single-use kit disclosed herein is referred to as a version 2.0-S tissue engineering kit which, when configured for volume augmentation, includes (i) a four-tray preparation sub-kit organized with sterile components including instructions that set forth a method for conducting an operative protocol which includes the centrifugation of lipoaspirate and the preparation of adipose tissue with an incubation procedure in order to make tissue concentrate and the most viable adipocytes available for physician use in treating a patient and (ii) a solutions sub-kit organized with vials of sterile saline to be used during the centrifugation of the lipoaspirate. (The addition of a sterile saline during centrifugation, as compared to the method for using a version 2.0 tissue engineering kit, produces a comparatively larger quantity of tissue concentrate.)

Figure 5:
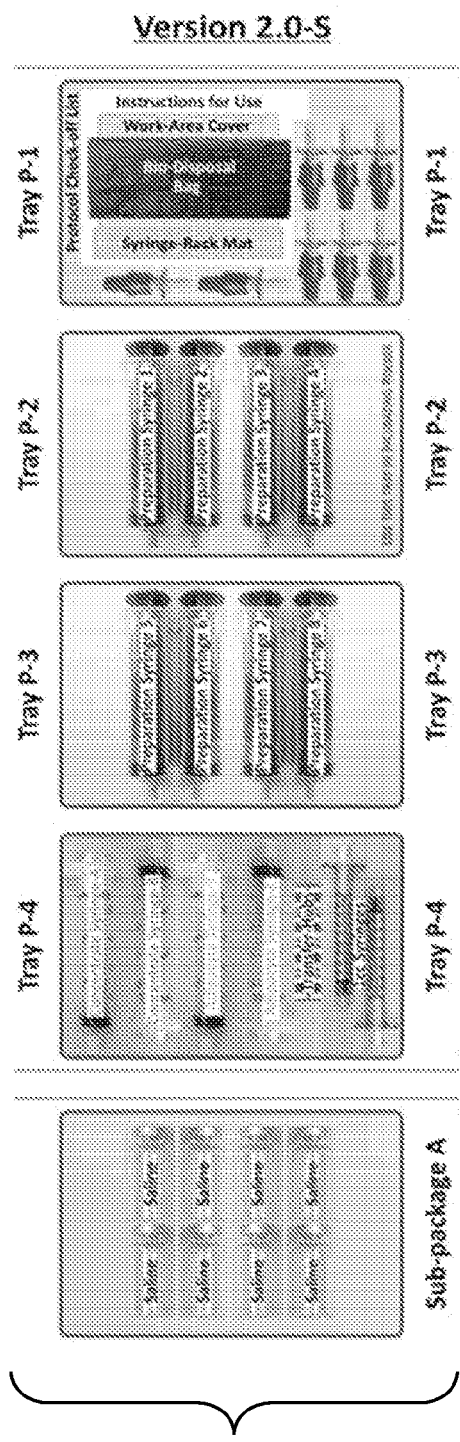
FIG. 5 depicts an enlargement of a portion of FIG. 3, showing an embodiment of a version 2.0-S tissue engineering kit.

To prepare such a blend of tissue concentrate and adipocytes, the lipoaspirate is rinsed during centrifugation with the sterile saline provided in the solutions sub-kit and, after this first centrifugation and recovery of tissue concentrate and parenchyma, (i) a portion (or portions) of the parenchyma (which contains the most viable adipocytes) is (are) set aside as reserved parenchyma and (ii) another portion (or portions) of the parenchyma is (are) incubated after having been mixed with a portion (or portions) of the tissue concentrate in a third-party incubating rocker at a temperature, tilt angle, speed level and for a time to facilitate digestion of the adipose tissue by endogenous enzymes in the adipose tissue (without addition of exogenous enzymes). After the foregoing procedure, the incubated parenchyma and combined tissue concentrate is centrifuged for a second time and a second quantity of tissue concentrate is recovered. The recovered second quantity of tissue concentrate is then mixed with the reserved parenchyma. An example of a version 2.0-S tissue engineering kit configured for augmentation is illustrated in the third column of FIG. 3 and in FIG. 5 and an example that sets forth the components of, and the method for using the version 2.0-S tissue engineering kit configured for augmentation is set forth in Example 3. All or any portion of the method described in Example 3 may be provided in the printed instructions included with such an embodiment of the 2.0-S tissue engineering kit.

In some embodiments, the sequence of steps comprises:
(1) setting up a sterile work area;
(2) setting up equipment;
(3) preparing the patient;
(4) harvesting adipose tissue from the patient's access site or sites;
(5) adding a saline solution to harvested adipose tissue;
(6) centrifuging harvested adipose tissue and saline solution;
(7) transferring post-centrifugation layers;
(8) setting aside adipocytes for utilization;
(9) combining parenchyma and tissue concentrate;
(10) incubating parenchyma and tissue concentrate;
(11) centrifuging the incubated parenchyma and tissue concentrate;
(12) transferring post-centrifugation layers;
(13) combining tissue concentrate layer with set-aside adipocytes; and
(14) utilizing combined tissue concentrate and adipocytes.

Version 3.0 Tissue Engineering Kit

Another exemplified embodiment of the single-use kit disclosed herein is referred to as a version 3.0 tissue engineering kit which, when configured for volume augmentation, includes (i) a four-tray preparation sub-kit organized with sterile components including instructions that sets forth a method for conducting an operative protocol which includes the centrifugation of lipoaspirate and the preparation of adipose tissue with an incubation procedure in order to make tissue concentrate and the most viable adipocytes available for physician use in treating a patient, (ii) a solutions sub-kit organized with (a) vials of sterile saline to be used during the centrifugation of the lipoaspirate, (b) vials of a sterile buffered solution to be used to bring an enzymatic reagent to a working solution, and (c) vials of sterile saline to be used during the centrifugation of adipose tissue after being treated with an enzymatic reagent, (iii) a two-tray hydration sub-kit organized with components including instructions that sets forth a method for conducting an preoperative protocol for the purpose of reconstituting (hydrating) a lyophilized enzymatic reagent), and (iv) a reagent sub-kit that contains the enzymatic reagent to be used with the version 3.0 tissue engineering kit. (The addition of an enzymatic reagent during incubation, as compared to the method for using a version 2.0-S tissue engineering kit, produces a comparatively larger quantity of tissue concentrate).

Figure 6A:
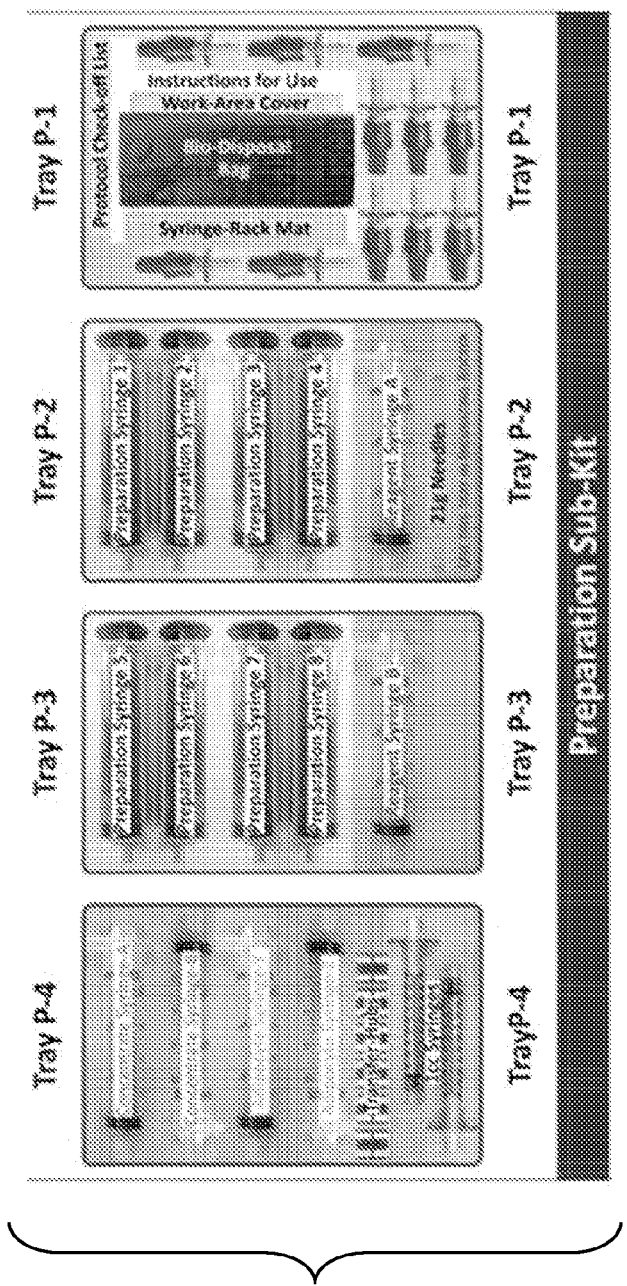
FIGS. 6A and 6B depict enlargements of a portion of FIG. 3, showing an embodiment of a version 3.0 tissue engineering kit, with a preparation sub-kit shown in FIG. 6A, and a solutions sub-kit, hydration sub-kit, and reagent sub-kit shown in FIG. 6B.
Figure 6B:
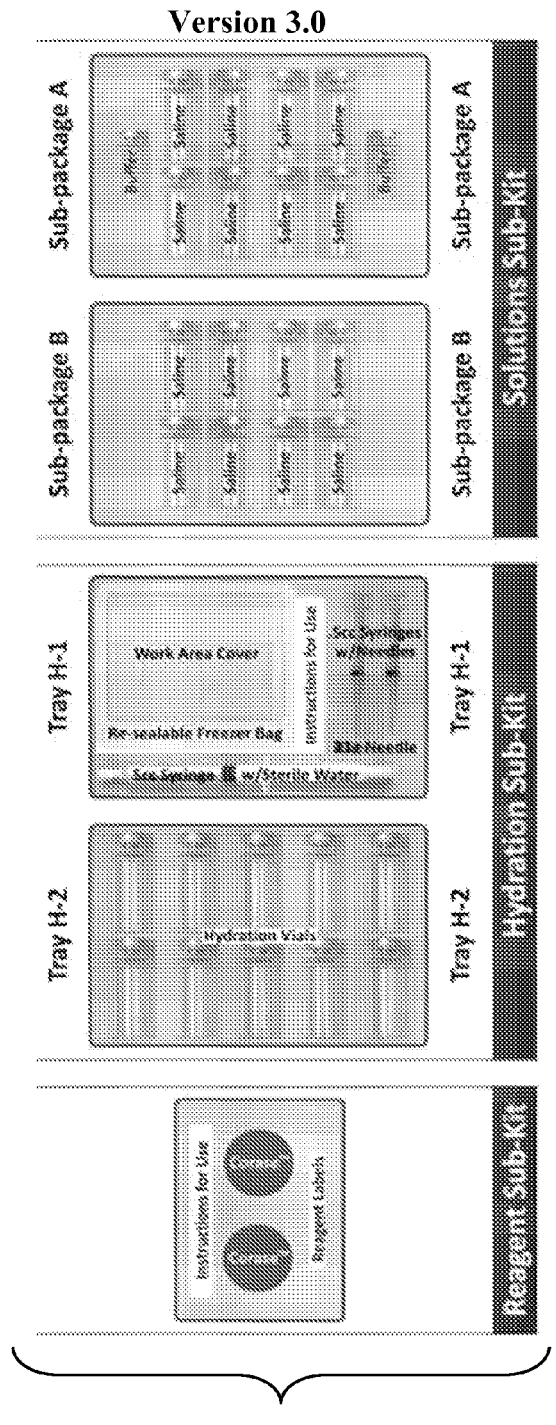
Figure 7:
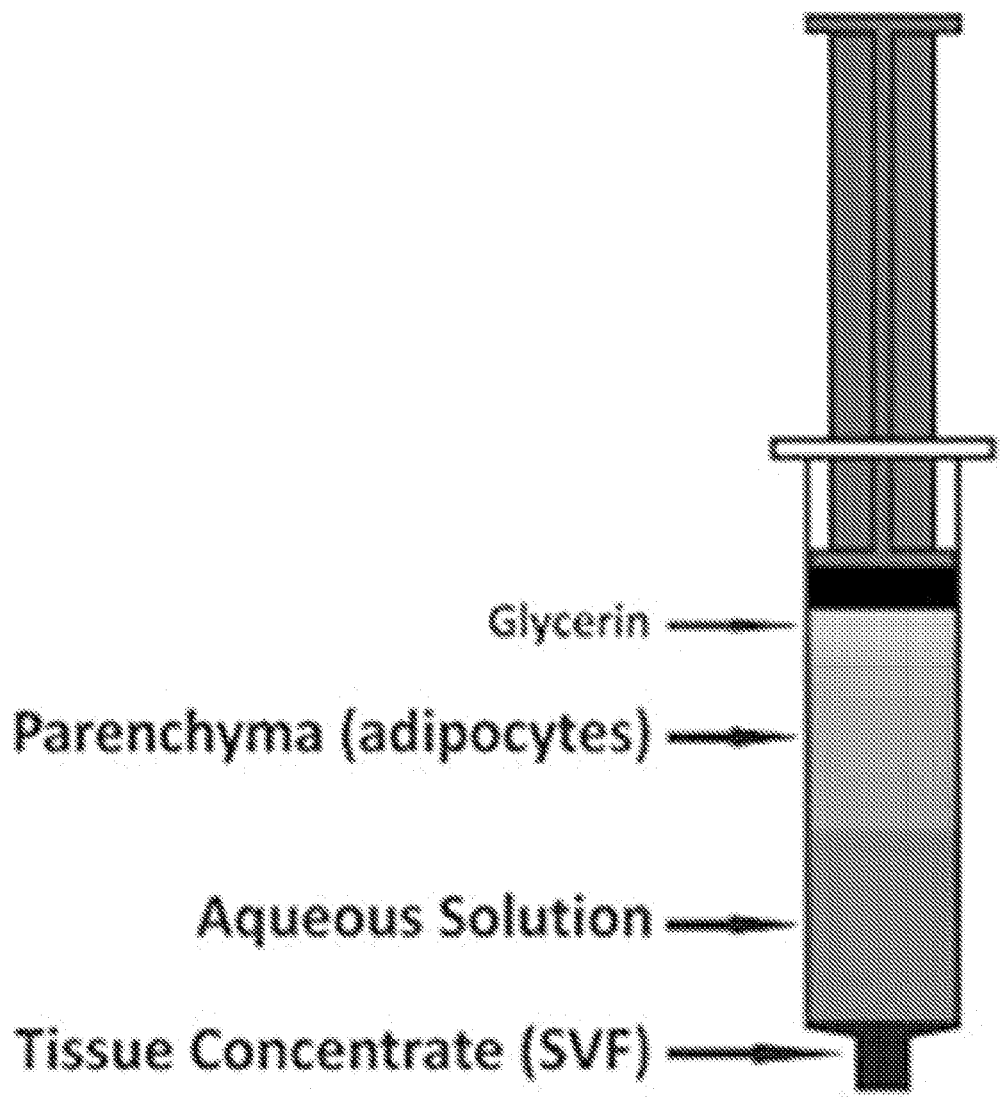
FIG. 7 depicts a syringe of the single-use kit disclosed herein after having been centrifuged pursuant to an embodiment of a method of the invention, wherein lipoaspirate is separated into its four constituent parts (from top to bottom: glycerin, parenchyma (adipocytes), aqueous solution, and tissue concentrate (stromal vascular fraction or "SVF"). In further embodiments where a sterile method is used to separate lipoaspirate layers, SVF and the most viable adipocytes can be prepared for therapeutic use in a patient.

To prepare such a blend of tissue concentrate and adipocytes, a preoperative protocol is first conducted for the purpose of reconstituting (hydrating) a lyophilized enzymatic reagent and distributing it into vials for use during the operative protocol. Next, the operative protocol is conducted where the lipoaspirate is rinsed during centrifugation with a portion of the sterile saline provided in the solutions sub-kit and, after this first centrifugation and recovery of tissue concentrate and parenchyma, (i) a portion (or portions) of the parenchyma is (are) set aside as reserved parenchyma and (ii) another portion (or portions) of the parenchyma is (are) mixed with an enzymatic reagent in a buffered solution and with a portion (or portions) of the tissue concentrate and this mixture is incubated in a third-party incubating rocker at a temperature, tilt angle, speed level and for a time to facilitate digestion of the adipose tissue. After the foregoing procedure, the digested parenchyma, enzymatic reagent in a buffered solution and tissue concentrate are centrifuged with the remaining portion of the sterile saline provided in the solutions sub-kit and a second quantity of tissue concentrate is recovered. The recovered second quantity of tissue concentrate is then mixed with the reserved parenchyma. An example of a version 3.0 tissue engineering kit configured for augmentation is illustrated in the fourth column of FIG. 3 and in FIGS. 6A-6B and an example that sets forth the components of, and the method for using the 3.0 tissue engineering kit configured for augmentation is set forth in Example 4. All or any portion of the method described in Example 4 may be provided in the printed instructions included with such an embodiment of the 3.0 tissue engineering kit.

In some embodiments, the sequence of steps comprise a preoperative protocol and an operative protocol, wherein the preoperative protocol comprises the steps of:
(1) setting up a work area;
(2) reconstituting the enzymatic reagent;
(3) transferring the reagent solution; and
(4) labeling and storing the hydration vials; and wherein the operative protocol comprises the steps of:
(1) setting up a sterile work area;
(2) setting up equipment;
(3) preparing the patient;
(4) harvesting adipose tissue from the patient's access site or sites;
(5) adding a saline solution to harvested adipose tissue;
(6) centrifuging harvested adipose tissue and saline solution;
(7) transferring post-centrifugation layers;
(8) setting aside adipocytes for utilization;
(9) combining parenchyma and tissue concentrate;
(10) preparing the reagent solution;
(11) incubating parenchyma, tissue concentrate and reagent solution;
(12) adding a saline solution to parenchyma, tissue concentrate and reagent solution;
(13) centrifuging parenchyma, tissue concentrate, reagent solution and saline solution;
(14) combining tissue concentrate layer with set-aside adipocytes; and
(15) utilizing combined tissue concentrate and adipocytes.

EXEMPLIFIED EMBODIMENTS

Examples of embodiments of the invention include, but are not limited to:

Embodiment 1

A standardized and optimized, modular, single-use kit for sterile or non-sterile preparation of biological material, the single-use kit comprising:
at least one modular single-use packaging frame;
at least one modular single-use tray disposed within the packaging frame comprised in the single-use kit, wherein at least one single-use tray disposed within the packaging frame comprised in the single-use kit has an identifying label;
at least one single-use component organized within any single-use tray disposed within the packaging frame comprised in the single-use kit; and
printed instructions for use comprising a sequence of steps directing use of the single-use kit for the sterile or non-sterile preparation of biological material, wherein one or more of the steps of the instructions corresponds to (correlates with) the identifying label on one or more of any single-use tray disposed within the packaging frame comprised in the single-use kit.

Embodiment 2

The kit of embodiment 1, wherein a plurality of the labeled trays are disposed within the packaging frame comprised in the kit, with each labeled tray having at least one component organized therein.

Embodiment 3

The kit of embodiment 2, wherein the plurality of labeled trays are labeled sequentially, with numbers or letters in ascending or descending order, and one or more steps of the instructions correspond to (correlate with) the sequentially labeled trays.

Embodiment 4

The kit of embodiment 3, wherein the components and the sequence of steps set forth in the instructions are for the preparation of biological material.

Embodiment 5

The kit of embodiment 3, wherein the components are sterile and the sequence of steps set forth in the instructions are for the sterile preparation of biological material (e.g., for use as a sterile research kit, diagnostic kit, or other kit for preparing biological material).

Embodiment 6

The kit of embodiment 3, wherein the components are sterile and the sequence of steps set forth in the instructions are for the sterile harvesting and sterile preparation of biological material (e.g., for use as a diagnostic kit or other single-use kit disclosed herein wherein the biological material is not immediately reintroduced into the subject).

Embodiment 7

The kit of embodiment 6, wherein the components and the sequence of steps set forth in the instructions are for preparation of biological material that is not autologous.

Embodiment 8

The kit of embodiment 7, wherein the components and the sequence of steps set forth in the instructions are for the preliminary preparation of biological material (the biological material is not to be immediately reintroduced into the subject).

Embodiment 9

The kit of embodiment 7, wherein the components and the sequence of steps set forth in the instructions are for the preservation and storage of biological material.

Embodiment 10

The kit of embodiment 6, wherein the components and the sequence of steps set forth in the instructions are for preparation of biological material that is autologous.

Embodiment 11

The kit of embodiment 10, wherein the components and the sequence of steps set forth in the instructions are for the preliminary preparation of biological material (the biological material is not to be immediately introduced into the subject).

Embodiment 12

The kit of embodiment 10, wherein the components and the sequence of steps set forth in the instructions are for the preservation and storage of the autologous biological material.

Embodiment 13

The kit of embodiment 3, wherein the components are sterile and the sequence of steps set forth in the instructions are for the sterile harvesting, sterile preparation, and sterile utilization of biological material for implantation or other such therapeutic use(s).

Embodiment 14

The kit of embodiment 13, wherein the components and sequence of steps set forth in the instructions are for preparing biological material that is autologous.

Embodiment 15

The kit of embodiment 14, wherein the components and sequence of steps set forth in the instructions are for preparing biological material that is human adipose tissue.

Embodiment 16

The kit of any one of embodiments 1 to 3, wherein one or more of the sequence of steps set forth in the instructions are for the concentration and use of cells and/or tissue.

Embodiment 17

The kit of any one of embodiments 1 to 3, wherein one or more of the sequence of steps set forth in the instructions are for the identification, isolation and use of nucleated cells.

Embodiment 18

The kit of any one of embodiments 1 to 3, wherein one or more of the sequence of steps set forth in the instructions are for the identification, isolation and use of stem cells.

Embodiment 19

The kit of any one of embodiments 1 to 3, wherein one or more of the sequence of steps set forth in the instructions are for the identification, isolation, differentiation and use of stem cells.

Embodiment 20

The kit of embodiment 3, wherein the kit has a single packaging frame (referred to herein as a preparation sub-kit) that is disposed with at least one tray organized with syringes that each comprise a syringe barrel and plunger, wherein the syringe barrel has a syringe-tip with a quick-release connector (e.g., Luer Taper, Luer-Lock or Luer-Slip), wherein the plunger comprises a plunger seal and plunger rod, wherein the plunger rod is used to move (slide) the plunger seal along the inner surface of the syringe barrel, and wherein the plunger seal maintains a sterile seal when inner surface of the plunger barrel or when being moved (slid) along the inner surface of the syringe barrel.

Embodiment 21

The kit of embodiment 20, wherein plunger rods can be disconnected from (and reconnected to) plunger seals while plunger seals remain in the syringe barrel of each respective syringe (thereby maintaining a sterile seal when a plunger rod is disconnected).

Embodiment 22

The kit of embodiment 20, wherein one or more of the sequence of steps set forth in the instructions require use of a centrifuge that spins centrifuge-carrier inserts horizontally at a speed of 2400 RPM (1020×g) and with a break-force of 5 for three minutes.

Embodiment 23

The kit of embodiment 20, wherein one or more of the sequence of steps set forth in the instructions require use of an incubating rocker that operates at a temperature of 37° C. and at a tilt-level of 6 for twenty minutes.

Embodiment 24

The kit of embodiment 20, wherein the kit further comprises other packaging (referred to herein as a solutions sub-kit) and at least one component (e.g., a vial or other container) organized therein that contains a liquid to be used with the preparation sub-kit of embodiment 20.

Embodiment 25

The kit of embodiment 20, wherein the kit further comprises another single packaging frame (referred to herein as a hydration sub-kit) that is disposed with at least one tray organized with at least one component to be used prior to a patient's procedure in order to prepare aliquots of an enzymatic reagent to be used with the preparation sub-kit of embodiment 20 at the time of a patient's procedure.

Embodiment 26

The kit of embodiment 25, wherein the kit has a single packaging frame (referred to herein as a reagent sub-kit) and at least one component (e.g., a canister in which is contained a vial) is organized therein that contains an enzymatic reagent to be used with the hydration sub-kit of embodiment 25 so that the enzymatic reagent can be hydrated and distributed into aliquots to be stored for use with the preparation sub-kit of embodiment 20.

Embodiment 27

The kit of any preceding embodiment, wherein the packaging frame comprises a top and bottom with complementary features that facilitate stable stacking of the packaging frame with vertically adjacent packaging frames.

Embodiment 28

The kit of any preceding embodiment, wherein the packaging frame comprises a plurality of labeled trays, wherein the trays can be slid partially out of, or be completely removed from, the packaging frame.

Embodiment 29

The kit of embodiment 20, wherein three labeled trays are disposed in the packaging frame including a first labeled tray, a second labeled tray, and a third labeled tray, wherein:
the first labeled tray (labeled, for example, as P-1) is organized with a work area cover, a bio-disposal bag, two transfer hubs, and printed instructions for using the preparation sub-kit comprised of a sequence of seven steps (referred to herein as the operative protocol) which is divided into a set-up phase, harvesting phase, preparation phase, and utilization phase,
the second labeled tray (labeled, for example, as P-2) is organized with two syringes of embodiment 21 having a 35 cc syringe-barrel capacity (each comprising a detachable plunger rod of a first color), and three syringe-tip caps for the 35 cc syringes, and
the third labeled tray (labeled, for example, as P-3) is organized with three syringes of embodiment 20 having a 35 cc syringe-barrel capacity (each comprising a detachable plunger rod of a second color), three syringe-tip caps for the 35 cc syringes, and two syringes of embodiment 20 having a 1 cc syringe-barrel capacity (each comprising a fixed plunger rod of a third color).

Embodiment 30

The kit of embodiment 29, wherein sterile components are separately packaged prior to being organized in each labeled tray, and the single packaging frame with the labeled trays and components therein is sealed with tamper-evident wrapping.

Embodiment 31

The kit of embodiment 15, wherein the components and instructions for preparing human adipose tissue are comprised in the preparation sub-kit of embodiment 30 (referred to herein as a version 1.0 tissue engineering kit).

Embodiment 32

The kit of embodiment 31, wherein the instructional steps of the operative protocol require the components of the preparation sub-kit and ancillary equipment including the centrifuge of (and in accordance with) embodiment 22, four centrifuge carrier inserts with syringe adapters, a syringe rack, a bio-disposal rack, a harvesting cannula, and an injection cannula.

Embodiment 33

The kit of embodiment 20, wherein four labeled trays are disposed in the single packaging frame, including a first labeled tray, a second labeled tray, a third labeled tray, and a fourth labeled tray, wherein:
the first labeled tray (labeled, for example, as P-1) is organized with a work area cover, a protocol check-off list, a syringe-rack mat, a bio-disposal bag, four transfer hubs, and printed instructions for using the preparation sub-kit comprised of a sequence of eleven steps (referred to herein as the operative protocol) which is divided into a set-up phase, harvesting phase, preparation phase, and utilization phase,
the second labeled tray (labeled, for example, as P-2) is organized with four syringes of embodiment 21 (labeled, for example, as preparation syringes 1-4) having a 35 cc syringe-barrel capacity (each comprising a detachable plunger rod of a first color), and four syringe-tip caps for the 35 cc syringes,
the third labeled tray (labeled, for example, as P-3) is organized with four syringes of embodiment 21 (labeled, for example, as preparation syringes 5-8) having a 35 cc syringe-barrel capacity (each comprising a detachable plunger rod of a second color), and four syringe-tip caps for the 35 cc syringes, and
the fourth labeled tray (labeled, for example, as P-4) is organized with one syringe of embodiment 20 (labeled, for example, as concentrate syringe) having a 35 cc syringe-barrel capacity (comprising a fixed plunger rod of a third color), two syringes of embodiment 20 (one labeled, for example, as Adipocyte Syringes Y and the other labeled, for example, as Adipocyte Syringe-Z) having a 35 cc syringe-barrel capacity (each comprising a fixed plunger rod of a fourth color), two syringes of embodiment 20 having a 1 cc syringe-barrel capacity (comprising a fixed plunger rod of a fifth color), and two transfer-hubs.

Embodiment 34

The kit of embodiment 33 wherein the cover on each labeled tray is a peel-back, chevron-type seal and the single packaging frame, labeled trays and components are terminally sterilized after the single packaging frame with labeled trays and components therein is sealed with tamper-evident wrapping.

Embodiment 35

The kit of embodiment 15, wherein the components and instructions for preparing human adipose tissue are comprised in the preparation sub-kit of embodiment 34 (referred to herein as a version 2.0 tissue engineering kit).

Embodiment 36

The kit of embodiment 35, wherein the instructional steps of the operative protocol require the components of the preparation sub-kit and ancillary equipment including the centrifuge of embodiment 22, eight centrifuge carrier inserts with syringe adapters, the incubating rocker of embodiment 23, a preparation cold-block, a syringe rack, a bio-disposal rack, a harvesting cannula, and an injection cannula.

Embodiment 37

The kit of embodiment 20, wherein four labeled trays are disposed in the single packaging frame, including a first labeled tray, a second labeled tray, a third labeled tray, and a fourth labeled tray, wherein:
the first labeled tray (labeled, for example, as P-1) is organized with a work area cover, a protocol check-off list, a syringe-rack mat, a bio-disposal bag, eight syringe-to-vial adapters, and printed instructions for using the preparation sub-kit comprised of a sequence of eleven steps (referred to herein as the operative protocol) which is divided into a set-up phase, harvesting phase, preparation phase, and utilization phase,
the second labeled tray (labeled, for example, as P-2) is organized with four syringes of embodiment 21 (labeled, for example, as preparation syringes 1-4) having a 35 cc syringe-barrel capacity (each comprising a detachable plunger rod of a first color), and four syringe-tip caps for the 35 cc syringes, the third labeled tray (labeled, for example, as P-3) is organized with four syringes of embodiment 21 (labeled, for example, as preparation syringes 5-8) having a 35 cc syringe-barrel capacity (each comprising a detachable plunger rod of a second color), and four syringe-tip caps for the 35 cc syringes, and the fourth labeled tray (labeled, for example, as P-4) is organized with one syringe of embodiment 20 (labeled, for example, as concentrate syringe) having a 35 cc syringe-barrel capacity (comprising a fixed plunger rod of a third color), two syringes of embodiment 20 (one labeled, for example, as Adipocyte Syringe-Y and the other labeled, for example, as Adipocyte Syringe-Z) having a 35 cc syringe-barrel capacity (each comprising a fixed plunger rod of a fourth color), two syringes of embodiment 20 having a 1 cc syringe-barrel capacity (comprising a fixed plunger rod of a fifth color), and two transfer-hubs.

Embodiment 38

The kit of embodiment 37, wherein the cover on each labeled tray is a peel-back, chevron-type seal and the single packaging frame, labeled trays and components are terminally sterilized after the single packaging frame with labeled trays and components therein is sealed with tamper-evident wrapping.

Embodiment 39

The kit of embodiment 24, wherein eight 20 cc vials of sterile saline and printed instructions are contained within the solutions sub-kit, wherein the printed instructions are for using the solutions sub-kit.

Embodiment 40

The kit of embodiment 39, wherein sterile components are separately packaged in sterile holders prior to being sealed with tamper-evident wrapping.

Embodiment 41

The kit of embodiment 15, wherein the components and instructions for preparing human adipose tissue are contained in the preparation sub-kit of embodiment 38 and the solutions sub-kit of embodiment 40 (collectively referred to herein as a version 2.0-S tissue engineering kit).

Embodiment 42

The kit of embodiment 41, wherein the instructional steps of the operative protocol require the components of the preparation sub-kit and solutions sub-kit as well as ancillary equipment including the centrifuge of embodiment 22, eight centrifuge carrier inserts with syringe adapters, the incubating rocker of embodiment 23, a preparation cold-block, a syringe rack, a bio-disposal rack, a harvesting cannula, and an injection cannula.

Embodiment 43

The kit of embodiment 26, wherein the reagent sub-kit includes two canisters that each contains a 5 mg vial of sterile, GMP-rated, enzymatic reagent in a lyophilized form, twenty hydration vial labels, and the printed instructions are for using the reagent sub-kit.

Embodiment 44

The kit of embodiment 43, wherein the packaging is sealed with tamper-evident wrapping.

Embodiment 45

The kit of embodiment 25, wherein two labeled trays are disposed in the packaging frame including a first labeled tray and a second labeled tray, wherein:

the first labeled tray (labeled, for example, as tray H-1) is organized with a work area cover, a re-sealable freezer bag, a 5 cc syringe prefilled with sterile water, a sterile 21 gauge needle, two sterile 0.5 cc syringes that each have an attached sterile needle, and printed instructions, wherein the printed instructions are for using the hydration sub-kit comprised of a sequence of four steps referred to as the preoperative protocol, the second labeled tray (labeled, for example as tray H-2) is organized with ten 20 cc hydration vials each capped to seal the sterile interior.

Embodiment 46

The kit of embodiment 45, wherein sterile components are separately packaged prior to being organized in each labeled tray, and the packaging frame with the labeled trays and components therein is sealed with tamper-evident wrapping.

Embodiment 47

The kit of embodiment 20, wherein four labeled trays are disposed in the packaging frame, including a first labeled tray, a second labeled tray, a third labeled tray, and a fourth labeled tray, wherein:

the first labeled tray (labeled, for example, as tray P-1) is organized with a work area cover, a protocol check-off list, a syringe-rack mat, a bio-disposal bag, eleven syringe-to-vial adapters, and printed instructions, wherein the printed instructions are for using the preparation sub-kit comprised of a sequence of twelve steps referred to as the operative protocol which is divided into a set-up phase, harvesting phase, preparation phase, and utilization phase, the second labeled tray (labeled, for example, as tray P-2) is organized with four syringes of embodiment 21 (labeled, for example, as preparation syringes 1-4) having a 35 cc syringe-barrel capacity (each comprising a detachable plunger rod of a first color), four syringe-tip caps for the 35 cc syringes, one syringe of embodiment 20 (labeled, for example, as reagent syringe-A) having a 35 cc syringe-barrel capacity (and comprising a fixed plunger rod of a second color), and two 21 g needles, the third labeled tray (labeled, for example, as tray P-3) is organized with four syringes of embodiment 21 (labeled, for example, as preparation syringes 5-8) having a 35 cc syringe-barrel capacity (each comprising a detachable plunger rod of a third color), four syringe-tip caps for the 35 cc syringes, one syringe of embodiment 20 (labeled, for example, as reagent syringe-B) having a 35 cc syringe-barrel capacity (and comprising a fixed plunger rod of the same color as reagent syringe-A), and two transfer-hubs, and the fourth labeled tray (labeled, for example, as tray P-4) is organized with one syringe of embodiment 20 (labeled, for example, as concentrate syringe) having a 35 cc syringe-barrel capacity (comprising a fixed plunger rod of a fourth color), two syringes of embodiment 20 (one labeled, for example, as Adipocyte Syringe-Y and the other labeled, for example as Adipocyte Syringe-Z) having a 35 cc syringe-barrel capacity (each comprising a fixed plunger rod of a fifth color), two syringes of embodiment 20 having a 1 cc syringe-barrel capacity (comprising a fixed plunger rod of a sixth color), and two transfer-hubs.

Embodiment 48

The kit of embodiment 47, wherein the cover on each labeled tray is a peel-back, chevron-type seal and the packaging frame, labeled trays and components are terminally sterilized after the packaging frame with labeled trays and components therein is sealed with tamper-evident wrapping.

Embodiment 49

The kit of embodiment 24, wherein sixteen 20 cc vials of sterile saline, two 15 cc vials of a sterile buffered solution, and printed instructions for using the solutions sub-kit are contained therein.

Embodiment 50

The kit of embodiment 49, wherein the sterile components are separately contained in sterile packaging prior to being sealed with tamper-evident wrapping.

Embodiment 51

The kit of embodiment 15, wherein the components and instructions for preparing human adipose tissue are comprised in the reagent sub-kit of embodiment 44, the hydration sub-kit of embodiment 46, the preparation sub-kit of embodiment 48, and the solutions sub-kit of embodiment 50 (collectively referred to herein as a version 3.0 tissue engineering kit).

Embodiment 52

The kit of embodiment 51, wherein the instructional steps of the preoperative protocol require components of the reagent sub-kit and the hydration sub-kit as well as ancillary equipment including a pharmaceutical-grade freezer/refrigeration unit(s) and a pre-op cold-block.

Embodiment 53

The kit of embodiment 51, wherein the instructional steps of the operative protocol require components of the preparation sub-kit and the solutions sub-kit as well as ancillary equipment including the centrifuge of embodiment 22, eight centrifuge carrier inserts with syringe adapters, the incubating rocker of embodiment 23, a preparation cold-block, a syringe rack, bio-disposal rack, a harvesting cannula, and an injection cannula.

Embodiment 54

The kit of any preceding claim, further comprising a reservoir for the disposal of liquid biological waste.

Embodiment 55

The kit of embodiment 54, wherein the reservoir is in a single-use tray.

Embodiment 56

The kit of embodiment 54, wherein the reservoir is a disposable bag, and wherein the single-use tray includes a port to accommodate a tube for connection to the bag.

Embodiment 57

The kit of embodiment 54, wherein the packaging frame comprises at least one wall, and wherein the at least one wall has the reservoir therein, with at least one port in the reservoir aligned with at least one port in the at least one wall, for the disposal of liquid biological waste.

Embodiment 58

The kit of embodiment 57, wherein the at least one wall comprises five walls including a rear portion, a top, a bottom a left sidewall, and a right sidewall, and wherein the reservoir is within and adjacent to the rear portion of the packaging frame.

Embodiment 59

The kit of embodiment 57, wherein the reservoir has an interior and the left and right sidewall of the packaging frame each have a top, wherein the reservoir has a first resealable port extending from the interior of the reservoir through the left sidewall, and wherein the reservoir has a second resealable port extending from the interior of the reservoir through the right sidewall.

Embodiment 60

A method for sterile or non-sterile preparation of biological material, comprising providing a standardized and optimized, modular, single-use kit of any one of embodiments 1 to 59, and carrying out the sequence of steps in the printed instructions directing use of the single-use kit.

Embodiment 61

The method of embodiment 60, wherein the sequence of steps set forth in the instructions are for the sterile preparation of biological material, and wherein the sequence of steps comprises:
(1) setting up a sterile work area;
(2) setting up equipment;
(3) centrifuging biological material;
(4) collecting certain portions of the centrifuged biological material to be set aside;
(5) collecting certain portions of the biological material for further preparation;
(6) further preparing certain portions of the biological material (e.g., by using incubation and/or a reagent treatment); and
(7) combining certain portions of the further-prepared biological material with certain portions of the biological material that was set aside.

Embodiment 62

The method of embodiment 61, wherein the sequence of steps set forth in the instructions are for the sterile harvesting and sterile preparation of biological material, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment); and
(9) combining certain portions of the further-prepared biological material with certain portions of the biological material that was set aside.

Embodiment 63

The method of embodiment 60, wherein the sequence of steps set forth in the instructions are for the sterile harvesting, sterile preparation, preservation and storage of biological material, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining certain portions of the further-prepared biological material with certain portions of the biological material that was set aside;
(10) preparing the combined biological material for storage; and
(11) packaging and shipping the combined biological material to be stored.

Embodiment 64

The method of embodiment 60, wherein the sequence of steps set forth in the instructions are for the sterile harvesting and sterile preparation of biological material which is to be further prepared, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining certain portions of the further-prepared biological material with certain portions of the biological material that was set aside;
(10) preparing the combined biological material for further preparation; and
(11) temporarily storing the combined biological material to be further prepared.

Embodiment 65

The method of embodiment 60, wherein the sequence of steps set forth in the instructions are for sterile harvesting, sterile preparation, and sterile utilization of biological material for non-autologous implantation or other therapeutic use, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining of certain portions of the further-prepared biological material with certain portions of the biological material that was set aside; and
(10) temporarily storing the combined biological material to be used in a patient other than the donor patient.

Embodiment 66

The method of embodiment 60, wherein the sequence of steps set forth in the instructions are for sterile harvesting, sterile preparation, and sterile utilization of biological material for autologous implantation or other therapeutic use, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the centrifuged biological material to be set aside;
(7) collecting certain portions of the biological material for further preparation;
(8) further preparing certain portions of the biological material (e.g., by using incubation and/or a reagent treatment);
(9) combining of certain portions of the further-prepared biological material with certain portions of the biological material that was set aside; and
(10) using the combined biological material to treat the donor patient.

Embodiment 67

The method of embodiment 60, wherein the sequence of steps set forth in the instructions are for the non-autologous sterile harvesting, sterile preparation, identification, isolation, and use of nucleated cells, and wherein the sequence of steps comprises:

(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate nucleated cells; and
(9) temporarily storing the nucleated cells to be used in a patient other than the donor patient.

Embodiment 68

The method of embodiment 60, wherein the sequence of steps set forth in the instructions are for the autologous sterile harvesting, sterile preparation, identification, isolation, and use of nucleated cells, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate nucleated cells; and
(9) using the nucleated cells to treat the donor patient.

Embodiment 69

The method of embodiment 60, wherein the sequence of steps set forth in the instructions are for the non-autologous sterile harvesting, sterile preparation, identification, isolation, and use of stem cells, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate stem cells; and
(9) temporarily storing the stem cells to be used in a patient other than the donor patient.

Embodiment 70

The method of embodiment 60, wherein the sequence of steps set forth in the instructions are for the non-autologous sterile harvesting, sterile preparation, identification, isolation, and use of stem cells, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify and isolate stem cells; and
(9) using the stem cells to treat a patient other than the donor patient.

Embodiment 71

The method of embodiment 60, wherein the sequence of steps set forth in the instructions are for the non-autologous sterile harvesting, sterile preparation, identification, isolation, differentiation, and use of stem cells, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify, isolate and differentiate certain stem cells; and
(9) temporarily storing the differentiated stem cells to be used in a patient other than the donor patient.

Embodiment 72

The method of embodiment 60, wherein the sequence of steps set forth in the instructions are for the autologous sterile harvesting, sterile preparation, identification, isolation, differentiation, and use of stem cells, and wherein the sequence of steps comprises:
(1) setting up a sterile work area;
(2) setting up equipment;
(3) preparing the patient;
(4) harvesting the biological material;
(5) centrifuging biological material (with or without a rinse solution);
(6) collecting certain portions of the biological material for further preparation;
(7) further preparing certain portions of the biological material (e.g., by using incubation and/or a reagent treatment);
(8) analyzing the prepared biological material to identify, isolate and differentiate certain stem cells; and
(9) using the differentiated stem cells to treat the donor patient.

Embodiment 73

The method of embodiment 60, wherein the single-use kit is the version 1.0 tissue engineering kit of embodiment 31, and wherein the sequence of steps comprises:

(1) setting up a sterile work area;
(2) setting up equipment;
(3) preparing the patient;
(4) harvesting adipose tissue from the patient's access site or sites;
(5) centrifuging harvested adipose tissue;
(6) transferring post-centrifugation layers;
(7) combining tissue concentrate and adipocytes of transferred layers; and
(8) utilizing combined tissue concentrate and adipocytes.

Embodiment 74

The method of embodiment 60, wherein the single-use kit is the version 2.0 tissue engineering kit of embodiment 35, and wherein the sequence of steps comprises:
(1) setting up a sterile work area;
(2) setting up equipment;
(3) preparing the patient;
(4) harvesting adipose tissue from the patient's access site or sites;
(5) centrifuging harvested adipose tissue;
(6) transferring post-centrifugation layers;
(7) setting aside adipocytes for utilization;
(8) combining parenchyma and tissue concentrate;
(9) incubating parenchyma and tissue concentrate;
(10) centrifuging the incubated parenchyma and tissue concentrate;
(11) combining tissue concentrate layer with set-aside adipocytes; and
(12) utilizing combined tissue concentrate and adipocytes.

Embodiment 75

The method of embodiment 60, wherein the single-use kit is the version 2.0-S tissue engineering kit of embodiment 41, and wherein the sequence of steps comprises:
(1) setting up a sterile work area;
(2) setting up equipment;
(3) preparing the patient;
(4) harvesting adipose tissue from the patient's access site or sites;
(5) adding a saline solution to harvested adipose tissue;
(6) centrifuging harvested adipose tissue and saline solution;
(7) transferring post-centrifugation layers;
(8) setting aside adipocytes for utilization;
(9) combining parenchyma and tissue concentrate;
(10) incubating parenchyma and tissue concentrate;
(11) centrifuging the incubated parenchyma and tissue concentrate;
(12) transferring post-centrifugation layers;
(13) combining tissue concentrate layer with set-aside adipocytes; and
(14) utilizing combined tissue concentrate and adipocytes.

Embodiment 76

The method of embodiment 60, wherein the single-use kit is the version 3.0 tissue engineering kit of embodiment 51, wherein the sequence of steps comprise a preoperative protocol and an operative protocol, and wherein the preoperative protocol comprises the steps of:
(1) setting up a work area;
(2) reconstituting the enzymatic reagent;
(3) transferring the reagent solution; and
(4) labeling and storing the hydration vials; and wherein the operative protocol comprises the steps of:
(1) setting up a sterile work area;
(2) setting up equipment;
(3) preparing the patient;
(4) harvesting adipose tissue from the patient's access site or sites;
(5) adding a saline solution to harvested adipose tissue;
(6) centrifuging harvested adipose tissue and saline solution;
(7) transferring post-centrifugation layers;
(8) setting aside adipocytes for utilization;
(9) combining parenchyma and tissue concentrate;
(10) preparing the reagent solution;
(11) incubating parenchyma, tissue concentrate and reagent solution;
(12) adding a saline solution to parenchyma, tissue concentrate and reagent solution;
(13) centrifuging parenchyma, tissue concentrate, reagent solution and saline solution;
(14) combining tissue concentrate layer with set-aside adipocytes; and
(15) utilizing combined tissue concentrate and adipocytes.

Embodiment 77

The method of embodiment 60, wherein one or more of the sequence of steps set forth in the instructions are for the concentration and use of cells and/or tissue.

Embodiment 78

The method of embodiment 60, wherein one or more of the sequence of steps set forth in the instructions are for the identification, isolation and use of nucleated cells.

Embodiment 79

The method of embodiment 60, wherein one or more of the sequence of steps set forth in the instructions are for the identification, isolation and use of stem cells.

Embodiment 80

The method of embodiment 60, wherein one or more of the sequence of steps set forth in the instructions are for the identification, isolation, differentiation and use of stem cells.

Embodiment 81

The method of embodiment 60, wherein the kit is the kit of embodiment 20, and wherein one or more of the sequence of steps set forth in the instructions require use of a centrifuge that spins centrifuge-carrier inserts horizontally at a speed of 2400 RPM (1020×g) and with a break-force of 5 for three minutes.

Embodiment 82

The method of embodiment 60, wherein the kit is the kit of embodiment 20, and wherein one or more of the sequence of steps set forth in the instructions require use of an incubating rocker that operates at a temperature of 37° C. and at a tilt-level of 6 for twenty minutes.

Embodiment 83

The method of embodiment 60, wherein the kit is the kit of embodiment 31, and wherein the instructional steps of the operative protocol require the components of the preparation sub-kit and ancillary equipment including the centrifuge of (and in accordance with) embodiment 22, four centrifuge carrier inserts with syringe adapters, a syringe rack, a bio-disposal rack, a harvesting cannula, and an injection cannula.

Embodiment 84

The method of embodiment 60, wherein the kit is the kit of embodiment 35, and wherein the instructional steps of the operative protocol require the components of the preparation sub-kit and ancillary equipment including the centrifuge of embodiment 22, eight centrifuge carrier inserts with syringe adapters, the incubating rocker of embodiment 23, a preparation cold-block, a syringe rack, a bio-disposal rack, a harvesting cannula, and an injection cannula.

Embodiment 85

The method of embodiment 60, wherein the kit is the kit of embodiment 41, and wherein the instructional steps of the operative protocol require the components of the preparation sub-kit and solutions sub-kit as well as ancillary equipment including the centrifuge of embodiment 22, eight centrifuge carrier inserts with syringe adapters, the incubating rocker of embodiment 23, a preparation cold-block, a syringe rack, a bio-disposal rack, a harvesting cannula, and an injection cannula.

Embodiment 86

The method of embodiment 60, wherein the kit is the kit of embodiment 51, and wherein the instructional steps of the preoperative protocol require components of the reagent sub-kit and the hydration sub-kit as well as ancillary equipment including a pharmaceutical-grade freezer/refrigeration unit and a pre-op cold-block.

Embodiment 87

The method of embodiment 60, wherein the kit is the kit of embodiment 51, and wherein the instructional steps of the operating protocol require components of the preparation sub-kit and the solutions sub-kit as well as ancillary equipment including the centrifuge of embodiment 22, eight centrifuge carrier inserts with syringe adapters, the incubating rocker of embodiment 23, a preparation cold-block, a syringe rack, bio-disposal rack, a harvesting cannula, and an injection cannula.

Definitions

As used herein, the terms "a," "an," "the" and similar referents in the context of describing the invention (especially in the context of the following claims) are to be construed to cover both the singular and the plural, unless otherwise indicated herein or clearly contradicted by context.

As used herein, the term "adipocytes" refers to the fat cells that are a primary component of adipose tissue. For purposes herein, the other primary component of adipose tissue is the stromal vascular fraction.

As used herein, the term "adipose tissue" refers to loose connective tissue that stores energy, insulates the body and, in the case of brown adipose tissue, generates body heat.

As used herein, the term "augmentation" in the context of soft tissue augmentation refers to the use of prepared adipose tissue for the replacement of volume loss and enhancement of dermal, subcutaneous, and muscular deficiencies that result from trauma, surgical defects, lipoatrophic conditions, photoaging, or chronological aging. Examples of synthetic or bio-engineered filling agents used for this same purpose include, for example, Adatosil 5000 (silicone), Aquamid (poly-acrylamide gel), Artefill (bovine collagen with poly(methyl methacrylate) beads, Bolotero Soft and Boloteric Basic (non-animal hyaluronic acid derived from bacterial fermentation), Bio-Alcamid (poly-acrylamide), Captique (non-animal-stabilized hyaluronic acid (NASHA) derived from plant), Cosmoderm and Cosmoplast (recombinant human collagen), Fascian (human cadaveric preserved particulate fascia lata), subcutaneous fat (autologous), Hylaform (hyaluronic acid derived from domestic fowl coxcombs), Isolagen (autologous fibroblasts), Juvederm (non-animal-stabilized hyaluronic acid (NASHA) derived from bacterial fermentation), Ultra Plus XC (non-animal-stabilized hyaluronic acid (NASHA) derived from bacterial fermentation, with 0.3% lidocaine), Prevelle Silk (non-animal-stabilized hyaluronic acid with 0.3% lidocaine), Radiesse (synthetic calcium hydroxylapatite), Restylane (non-animal-stabilized hyaluronic acid (NASHA) derived from bacterial fermentation), Perlane L (non-animal-stabilized hyaluronic acid (NASHA) derived from bacterial fermentation, with 0.3% lidocaine), Silikone-1000 and Adatosil-5000 (silicone), Softform (Gore-Tex), Sculptra (lyophilized poly-L-lactic acid), Zyderm and Zyplast (bovine collagen). Augmentation can also be achieved with products that are used as a "matrix" (or "scaffold") such as, but not limited to, Alloderm (acellular processed human cadaveric dermal allograft) which forms a structure that the body fills in with its natural tissue-regeneration process. Such a matrix (or scaffold) can be used with the single-use kits disclosed herein when configured for augmentation in order to accelerate what the body would otherwise do naturally.

As used herein, the term "biological material" refers to products of biological processes, such as cells, tissue, organs, polynucleotides, genomic DNA, plasmid DNA, DNA fragments, RNA, oligonucleotides, proteins, peptides, viruses, etc., and to such products that are synthetically made (e.g., synthetic peptides).

As used herein, the term "culture" is used to denote the maintenance or cultivation of cells in vitro including the culture of single cells. Cultures can be cell, tissue, or organ cultures, depending upon the extent of organization.

As used herein, the term "differentiated" refers to those cells that maintain in culture all, or a substantial amount of, their specialized structure and function typical of the cell type in vivo. Partially differentiated cells maintain less than a substantial amount of their full complement of specialized structure and/or function.

As used herein, the term "healthcare practitioner" means one or more medical professionals (as is appropriate and in accordance with local regulations) that may include, for example, physician(s), physician's assistant(s), nurse(s) medical technicians(s), and/or individual(s) performing research and experimentation for healthcare purposes. A healthcare practitioner that uses the single-use kits disclosed herein may be a sterile healthcare practitioner or non-sterile healthcare practitioner.

As used herein, the term "sterile healthcare practitioner" refers to a healthcare practitioner of the single-use kits disclosed herein who is sterile or "scrubbed" and who works directly in a sterile field and/or comes in contact with a sterile single-use kit, packaging frame, sub-kit, component, or other sterile item, while following the principles of aseptic technique. The principles of aseptic technique include, but are not limited to, the following principles: scrubbed persons functioning within a sterile field; sterile drapes used to create a sterile field; all items used within a sterile field being sterile; all items introduced into a sterile field being opened, dispensed, and transferred by methods that maintain sterility; a sterile field that is maintained and monitored constantly; all personnel moving within or around a sterile field doing so in a manner which maintains the sterile field; and, policies and procedures for maintaining a sterile field that are in written form, reviewed annually, and readily available to healthcare practitioners associated with each respective sterile field.

As used herein, the term "non-sterile healthcare practitioner" refers to a healthcare practitioner of the single-use kits disclosed herein who is not necessarily sterile or "scrubbed" and whose activities are not performed in a sterile field and do not require adherence to the principles of aseptic technique.

As used herein, the term "isolated" means removal from its native environment, and can include removal from its immediate native environment.

As used herein, the term "modular" refers to a structure that is an independent unit but is constructed on the basis of a standard pattern and/or dimensions such that it can be easily expanded or interconnected with other like structures, with each contributing to collectively form a higher order configuration comprising each structure as a component.

As used herein, the term "single-use" refers to a device or component of a device that is intended to perform its intended function during the operational parameters of a single operational procedure; however, such term is not to exclude reconditioning and/or recycling a device or component for future use.

As used herein, the phrase "each particular type of single-use kit" refers to a single-use kit which has been configured for a particular purpose and for use in accordance with a particular method as set forth with the included instructions. Particular types of single-use kits include, but are not limited to, tissue engineering kits, research kits, cell preservation kits, diagnostic kits, stem cell therapy kits and veterinary kits, for example.

As used herein, the term "tissue engineering" refers to the preparation of adipose tissue to yield tissue concentrate and the most viable adipocytes for physician use in treating patients.

Figure 3:
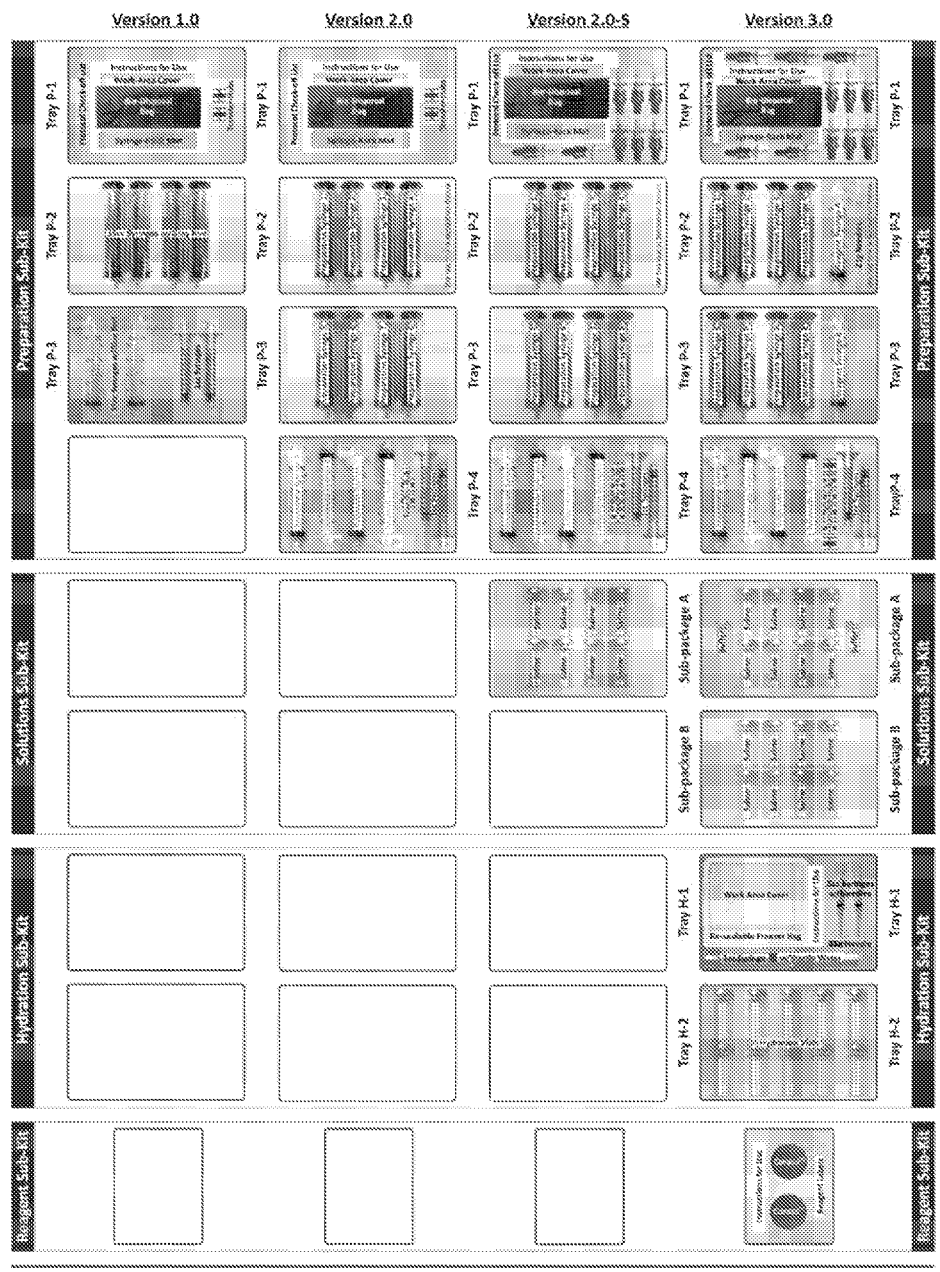
FIG. 3 depicts the components comprised in four versions of a tissue engineering kit that is configured for augmentation, which is an embodiment of the single-use kit described herein. Each column of FIG. 3 corresponds to a version of this particular type of tissue engineering kit (i.e., version 1.0, version 2.0, version 2.0-S, and version 3.0) and each row corresponds to sub-kits of this tissue engineering kit (i.e., preparation sub-kit, solutions sub-kit, hydration sub-kit and reagent sub-kit).
Figure 4:
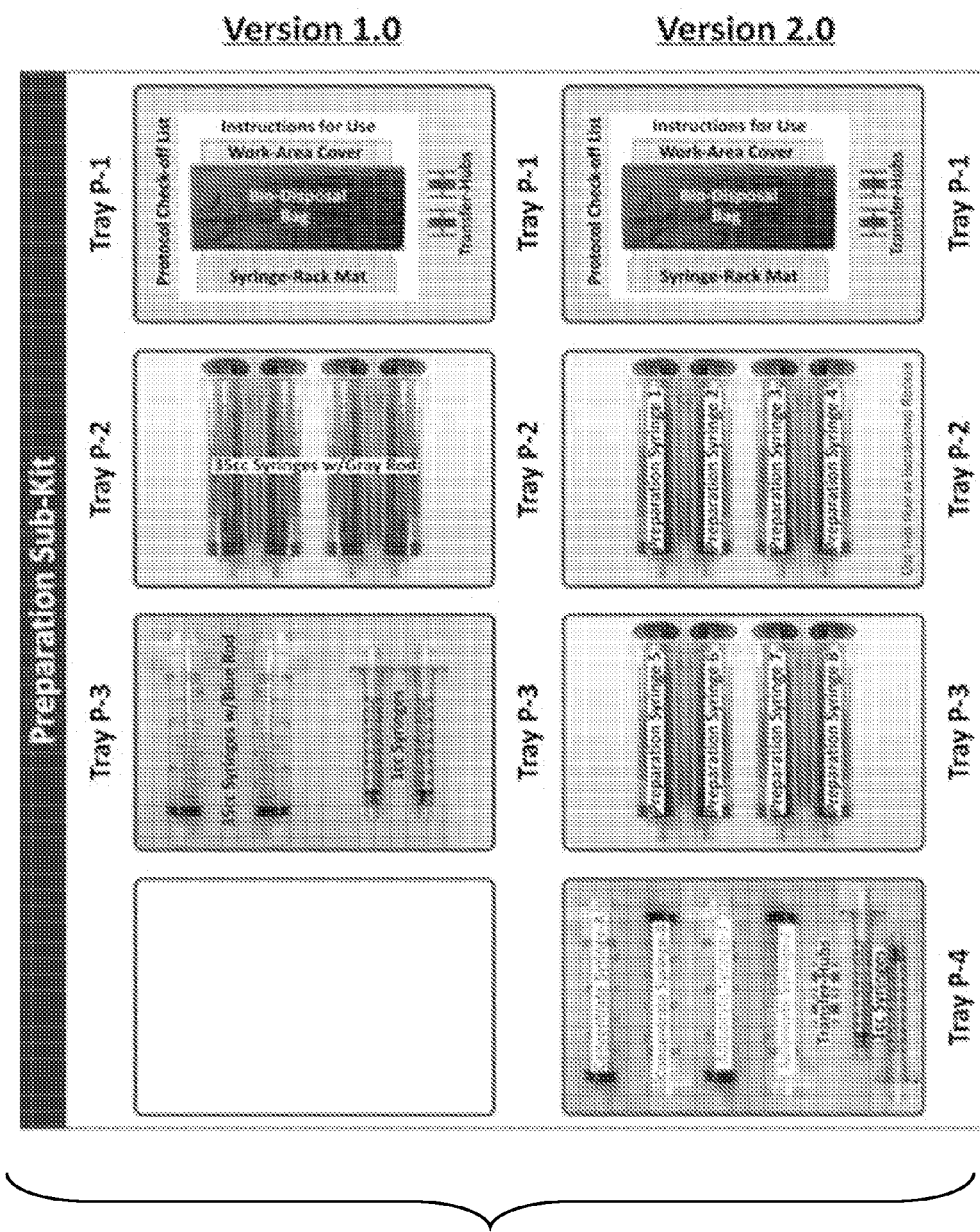
FIG. 4 depicts an enlargement of a portion of FIG. 3, showing embodiments of a version 1.0 (left) and a version 2.0 (right) tissue engineering kit.

As used herein, "tissue engineering kit(s)" refers to the single-use kits disclosed herein when configured with certain combinations of sub-kits, trays and components for use in tissue engineering in accordance with the instructions included with each type of tissue engineering kit. Tissue engineering kit types include, but are not limited to, those configured for volume augmentation, wound restoration and surgical reconstruction, for example. Tissue engineering kits configured for volume augmentation have been highlighted in this disclosure. Tissue engineering kits, when configured for volume augmentation, do not include a matrix, scaffold or any other component that would be introduced into the patient whereas wound restoration kits and surgical reconstruction kits may contain components for treatment of a wound (and/or other components) in addition to the components to be used for augmenting the tissue damaged as a result of the wound. Likewise, surgical reconstruction kits may include a matrix or scaffold (and/or other components which may be implanted into the patient) in addition to the components to be used for augmenting the tissue in need of reconstruction. For example, plastic surgeons and dermatologists can use a tissue engineering kit configured for augmentation for purposes of preparing adipose tissue for facial augmentation. FIG. 3 depicts the components in four versions of a tissue engineering kit that is configured for augmentation.

As used herein, the term "research kit(s)" refers to the single-use kits disclosed herein when configured with certain combinations of sub-kits, trays and components for use by healthcare practitioners for purposes of developing new, or improving upon existing, medical technologies that can be delivered to patients by healthcare practitioners who use single-use kits and methods (once fully developed and commercialized) to treat their patients. Such research kits and the included instructions are highly adaptable to the research and/or experimentation being conducted and can be produced in small quantities for highly-defined purposes.

As used herein, the term "cell preservation kit(s)" refers to the single-use kit disclosed herein when configured with certain combinations of sub-kits, trays and components for use in identifying and preserving cells for future use, wherein tissue concentrate (or certain cells thereof) are preserved for storage.

As used herein, the term "diagnostic kit(s)" refers to the single-use kit disclosed herein when configured with certain combinations of sub-kits, trays and components for use by healthcare practitioners who need to identify the nature and cause of a particular patient ailment, and/or to determine the effectiveness and/or dosage (or other such parameters) of a certain treatment for a particular patient.

As used herein, the term "stem cell therapy kit(s)" refers to the single-use kit disclosed herein when configured with certain combinations of sub-kits, trays and components for use in identifying, isolating and/or differentiating and utilizing (or storing) certain cells for therapeutic purposes (or for further preparation for immediate or future use).

As used herein, the term "veterinary kit(s)" refers to the single-use kit disclosed herein when configured with certain combinations of sub-kits, trays and components for use in identifying, isolating and/or differentiating and utilizing (or storing) certain cells for therapeutic use in animals (or for further preparation for immediate or future use).

As used herein, the term "optimized" in the context of the single-use kits disclosed herein, refers to the optimization of a protocol to achieve a desired result and the configuration of each kit accordingly. Instead of leaving important details to the discretion of the user, the single-use kits disclosed herein eliminate variation in results because a variety of users is given the capability to conduct a given protocol in the exact same way. Each kit is, essentially, a "protocol-in-a-box" and not merely a tool. Thus, a highly optimized protocol can be conducted the same way, each and every time, no matter the user.

As used herein, the term "standardized" refers to the (i) modularity of the single-use kits, packaging frames and trays which makes possible a variety of configurations that conform to the same basic design of the single-use kit and (ii) consistency of the specifications for each single-use component that is identified for a specific purpose in the instructions included with each single-use kit. The purpose of such "standardization" is to make it possible for healthcare practitioners to achieve predictable, consistent and repeatable results when using the single-use kits and methods disclosed herein.

As used herein, the term "sterile" refers to a substance or article that is non-pyrogenic and free of any germs or living microorganisms.

As used herein, the term "stromal vascular fraction" refers to that portion of adipose tissue which comprises ASCs (adipose stromal cells, which are progenitor cells).

As used herein, the term "tissue concentrate" refers to that portion of centrifuged adipose tissue which is primarily composed of the stromal vascular fraction.

As used herein, the terms "subject" and "patient" are used interchangeably to refer to humans or non-human animals, such as non-human mammals, including non-human primates, rodents, and pigs, for example. Specific examples of source and recipient species of biological material include, but are not limited to, humans, apes, chimpanzees, orangutans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, giant pandas, hyena, seals, sea lions, elephant seals, porpoises, dolphins, and whales.

Unless otherwise indicated, all numbers expressing quantities of ingredients, properties such as molecular weight, reaction conditions, and so forth used in this disclosure (including those in any figures and attachments) are to be understood as being modified in all instances by the term "about." Accordingly, unless indicated to the contrary, the numerical parameters set forth in this disclosure (including those in any figures and attachments) are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Any reference(s) to patents and printed publications made throughout this disclosure are hereby individually incorporated herein by reference in their entirety.

The embodiments of the invention(s) disclosed herein are illustrative of the principles of such and any refinements or modifications thereof are to be understood as being within the scope of the invention(s). Thus, by way of example, but not of limitation, there are numerous variations possible for the single-use kits disclosed herein, given the modularity of the packaging frames and trays as well as the multitude of components that could be comprised in each. Further, alternative configurations of the invention(s) disclosed herein may be utilized in accordance with that which is described herein. Accordingly, the invention described herein is not intended to be fully comprehensive for purposes of this disclosure nor limited to that as precisely shown and/or described.

All patents, patent applications, provisional applications, and publications referred to or cited herein are incorporated by reference in their entirety, including all figures and tables, to the extent they are not inconsistent with the explicit teachings of this specification.

EXAMPLES

Following are examples that illustrate procedures for practicing the invention. These examples should not be construed as limiting. All percentages are by weight and all solvent mixture proportions are by volume unless otherwise noted.

Example 1

Reviticell Kit 1.0 Tissue Augmentation Protocol

General Notes

The purpose of this 1.0 Tissue Augmentation Protocol is to prepare and utilize a patient's adipose tissue at the time of patient's procedure for therapeutic use. Universal strict sterile technique is required during this protocol which is comprised of seven annotated steps in four phases as follows:

Set-up phase to lay out components and set up equipment;
Harvesting phase to remove adipose tissue from patient;
Preparation phase to concentrate select portions of adipose tissue; and,
Utilization phase to utilize prepared adipose tissue to treat donor patient.

The 1.0 Tissue Augmentation Protocol is to be used with a 1.0 Reviticell Tissue Augmentation Kit which is comprised of a sterile packaging frame with three sterile trays. These trays contain sterile components used during certain steps of this protocol as indicated in the instructions for use.

After discarding any packing-and-shipping materials, the 1.0 Reviticell Tissue Augmentation Kit is to be stored (unopened in its protective wrapping) in a safe, secure and convenient place that is not subject to high temperatures.

If any part or component of the 3.0 Tissue Augmentation Kit is damaged or missing, the point of purchase should be notified so that which has been damaged or is missing can be replaced. In no event should a damaged component be used nor should any substitutions be made for any missing components.

The 1.0 Reviticell Tissue Augmentation Kit is to be used with the ancillary equipment that follows.

A small centrifuge that spins 4 carrier inserts horizontally which is to be operated at a speed of 2400 RPM (1020×g) and a break-force of 5 for three-minutes.

Four centrifuge carrier inserts (with syringe adapters) that are to be autoclaved after each procedure.

A syringe rack that is to be autoclaved after each procedure.

A bio-disposal rack that is to be autoclaved after each procedure.

A harvesting cannula that is to be autoclaved after each procedure.

An injection cannula that is to be autoclaved after each procedure.

Sub-Kit Component Details

The 1.0 Reviticell Augmentation Kit is comprised of a sterile packaging frame that houses four sterile trays containing sterile components as identified below.

Tray P-1:
Work-area cover
Instructions for use
Protocol check-list
Syringe-Rack Mat
Bio-disposal bag
Transfer-hubs (2)
Tray P-2:
35 cc syringes w/caps (4), having gray plunger rods that can be disconnected from each respective plunger seal with a twisting motion (to maintain sterility of syringe contents during centrifugation).
Tray P-3:
35 cc syringes w/caps (2), having fixed plunger rods that are blue.
1 cc Syringes (2)

Steps Required for 1.0 Tissue Augmentation Protocol

Note: The healthcare practitioner(s) performing all or any portion of the following steps is (are) to properly prepare and be outfitted for sterile use of packaging frame, tray(s) and/or component(s) (as the case may be) unless all or any portion of a particular step is addressed to "[non-sterile healthcare practitioner]" in which case sterile healthcare practitioner may not perform the step (or portion thereof) so noted.

Step 1: Set-Up Phase—Set Up Sterile Work-Area (a) (i) [Non-sterile healthcare practitioner] open preparation sub-kit wrapping (which acts as the sterile barrier for the packaging frame) so that sterile healthcare practitioner can reach in and move sterile packaging frame to sterile field; alternatively, (ii) [Non-sterile healthcare practitioner] open preparation sub-kit wrapping and remove protective cover from packaging frame so that sterile healthcare practitioner can reach in and move sterile trays to sterile field; alternatively, (iii)[Non-sterile healthcare practitioner] open preparation sub-kit wrapping, remove protective cover from packaging frame, remove each tray when directed by sterile healthcare practitioner. (Do not set trays on sterile field.) Remove protective seal from each tray when directed by sterile healthcare practitioner and either allow sterile healthcare practitioner to reach in and remove sterile components or dump contents of tray onto sterile field as directed by sterile healthcare practitioner. Be careful not to touch components or any part of tray protected by protective seal.

The remaining steps of this protocol are set forth assuming that one of the first two of these three alternatives has been selected.

(b) Remove work-area cover from Tray P-1 and cover work area; then, place contents of Tray P-1 on work-area cover (which is sterile) and dispose of Tray P-1.

(c) [Non-sterile healthcare practitioner] open and hold autoclave bags containing harvesting cannula, syringe rack, bio-disposal rack and injection cannula so that sterile healthcare practitioner can remove items for placement on work-area cover and/or sterile field as is appropriate. Syringe-rack mat (from Tray P-1) is to be placed below syringe rack.

(d) Place bio-disposal bag (from Tray P-1) over bio-disposal rack and then place assembly on sterile work-area cover; hand protocol check-list to non-sterile healthcare practitioner for use in a non-sterile area.

(e) [Non-sterile healthcare practitioner] fill in appropriate information on protocol check-list, being sure to include a patient reference number (which does not directly disclose patient identity) that corresponds to patient's file.

Note that bio-disposal bag is only for collection of syringe contents (i.e., liquids) and is to be properly disposed of after each procedure—it is not to be used for any components or other items that could puncture bag.

Step 2: Set-Up Phase—Set Up Equipment (a) [Non-sterile healthcare practitioner] turn on centrifuge power switch (but do not start spinning of carrier), adjust settings to a speed of 2,400 RPM (1020×g) and a break-force of 5 (in each instance when called for).

(b) [Non-sterile healthcare practitioner] open autoclave bag(s) containing carrier inserts so that sterile healthcare practitioner can reach in and place them in centrifuge carrier.

Step 3: Harvesting Phase—Prepare Patient

Using sound medical judgment, patient's physician should include the following steps as a part of physician's protocol for preparing patient:

(a) Identify harvesting area(s);

(b) Prepare harvesting areas(s) using physician-provided sterile preparation;

(c) Anesthetize access site(s) using physician-provided anesthetic;

(d) Create access site(s) by incising skin with physician-provided scalpel; and, (e) Gently infuse patient's subcutaneous adipose tissue via access site(s) by injecting physician-provided solution which contains a mixture of saline, anesthetic and epinephrine.

Step 4: Harvesting Phase—Harvest Adipose Tissue

Using sound medical judgment, patient's physician should (i) allow sufficient time to elapse prior to harvesting adipose tissue (as judged by adequate skin blanching which is caused by epinephrine) so as to collect adipose tissue with as little blood in it as possible and (ii) proceed with the steps that follow:

(a) Remove caps from each of four syringes with gray plunger rods (from Tray P-2) and attach harvesting cannula to first Preparation Syringe;

(b) Harvest adipose tissue via patient's access site(s), filling the first syringe to 35 cc mark;

(c) Repeat process for remaining three syringes (doing so will result in 30 cc of prepared tissue for use in Step 7); and, (d) Place filled syringes in syringe rack when done and dispose of Tray P-2.

Step 5: Preparation Phase—Centrifuge Harvested Adipose Tissue (a) [Non-sterile healthcare practitioner] open centrifuge lid.

(b) Twist plunger rods to remove them from plunger seals of syringes with gray plunger rods.

(c) Place each syringe barrels (with syringe-tip down) into each of the four centrifuge carrier inserts.

(d) [Non-sterile healthcare practitioner] close centrifuge lid, set timer for 3 minutes, start cycle, and open lid at end of cycle.

Step 6: Preparation Phase—Transfer Post-Centrifugation Layers (a) Connect a syringe with blue plunger rod (from Tray P-3) to a transfer-hub (from Tray P-1).

(b) Remove a syringe barrel from centrifuge carrier insert and reconnect a gray plunger rod to plunger seal (holding syringe barrel vertical with syringe-tip down so as not to disturb layers that separate during centrifugation).

(c) Carefully remove cap and connect to transfer-hub on syringe with blue plunger rod (while maintaining position of syringe with gray plunger rod so as not to disturb separated layers).

(d) Gently flick tip of syringe with gray plunger rod to break up tissue concentrate which may have adhered to the plastic.

(e) Carefully transfer into syringe with blue plunger rod bottom layer from syringe with gray plunger rod (which is referred to as Tissue Concentrate) and a minute amount of solution from just above it (which is referred to as Aqueous Solution).

(f) Disconnect syringe with blue plunger rod from transfer-hub and cap it.

(g) Expel Aqueous Solution from syringe with gray plunger rod (which still has transfer-hub connected) into bio-disposal bag, except for a minute amount of Aqueous Solution just below suspended layer above (which is referred to as Parenchyma).

(h) Remove cap from syringe with blue plunger rod and reconnect it to transfer-hub on syringe with gray plunger rod (while continuing to hold syringe with gray plunger rod vertical with syringe-tip down).

(i) Gently transfer 7.5 cc Parenchyma into syringe with blue plunger rod then remove it from transfer-hub and cap it. Dispose of syringe with gray plunger rod.

(j) Repeat Step 6(b) through Step 6(i) but use a new syringe with gray plunger rod (from Tray P-2). When done, the syringe with blue plunger rod will contain 15 cc Parenchyma and Tissue Concentrate from the first two syringes with gray plunger rods.

(k) Repeat Step 6(b) through Step 6(i) but use the remaining two syringes with gray plunger rods (from Tray P-2) and make transfers into the remaining syringe with blue plunger rod (from Tray P-3). When done, the second syringe with blue plunger-rod will contain 15 cc Parenchyma and Tissue Concentrate from the second two syringes with gray plunger rods.

Step 7: Utilization Phase—Utilize Recombined Tissue Concentrate and Adipocytes (a) Connect syringes with blue plunger-rods using transfer-hub and transfer contents from one into the other, then back into the first, then half back into the second.

(b) Remove one syringe from transfer-hub and connect in its place a 1 cc syringe (from Tray P-3) or to an alternative injection syringe provided by physician.

(c) Transfer a portion of prepared adipose tissue into the syringe to be used for injection then remove injection syringe from transfer-hub and attach injection cannula.

(d) The prepared adipose tissue in both syringes can be transferred and utilized as determined by physician.

(e) When physician is finished, mark protocol check-list in space provided to indicate current time.

(f) Properly dispose of bio-disposal bag and all remaining 1.0 Tissue Augmentation Kit components and packaging.

(g) Autoclave harvesting cannula, bio-disposal rack, centrifuge carrier inserts and injection cannula.

Example 2

Reviticell Kit 2.0 Tissue Augmentation Protocol

General Notes

The purpose of this 2.0 Tissue Augmentation Protocol is to prepare and utilize a patient's adipose tissue at the time of patient's procedure for therapeutic use. Universal strict sterile technique is required during this protocol which is comprised of eleven annotated steps in four phases as follows:

Set-up phase to lay out components and set up equipment;
Harvesting phase to remove adipose tissue from patient;
Preparation phase to concentrate select portions of adipose tissue; and,
Utilization phase to utilize prepared adipose tissue to treat donor patient.

This 2.0 Tissue Augmentation Protocol requires use of a 2.0 Tissue Augmentation Kit which is comprised of a sterile packaging frame with four sterile trays. These trays contain sterile components used during certain steps of this protocol as indicated in the instructions for use.

After discarding any packing-and-shipping materials, this kit is to be stored (unopened in its protective wrapping) in a safe, secure and convenient place that is not subject to high temperatures.

If any part or component of the 2.0 Tissue Augmentation Kit is damaged or missing, the point of purchase should be notified so that which has been damaged or is missing can be replaced. In no event should a damaged component be used nor should any substitutions be made for any missing components.

The 2.0 Tissue Augmentation Kit is to be used with the ancillary equipment as follows.

Preparation cold-block that is to be used during this protocol to maintain a cold temperature for Adipocyte Syringes and Concentrate Syringes (later described). Preparation cold-block is to be autoclaved after each procedure and placed into a refrigeration unit (in unopened autoclave bag).

A small centrifuge that spins 8 carrier inserts horizontally which is to be operated at a speed of 2400 RPM (1020×g) and a break-force of 5 for three minutes (in each instance when called for).

Eight centrifuge carrier inserts (with syringe adapters) that are to be autoclaved after each procedure.

An incubating rocker which is to be operated at temperature of 37° C. and a tilt-level of 6 for twenty minutes (in each instance when called for).

A syringe rack that is to be autoclaved after each procedure.

A bio-disposal rack that is to be autoclaved after each procedure.

A harvesting cannula that is to be autoclaved after each procedure.

An injection cannula that is to be autoclaved after each procedure.

Sub-Kit Component Details

The 2.0 Tissue Augmentation Kit is comprised of a sterile packaging frame that houses four sterile trays containing the sterile components as identified below.

Tray P-1:
Work-area cover
Instructions for use
Protocol check-list
Syringe-rack mat
Bio-disposal bag
Transfer-hubs (2)

Tray P-2:
35 cc syringes w/caps (4), labeled Preparation Syringe-1, Preparation Syringe-2, Preparation Syringe-3 and Preparation Syringe-4, having gray plunger rods that can be disconnected from each respective plunger seal with a twisting motion (to maintain sterility of syringe contents during centrifugation).

Tray P-3:
35 cc syringes w/caps labeled (4), Preparation Syringe-5, Preparation Syringe-6, Preparation Syringe-7 and Preparation Syringe-8, having gray plunger rods that can be disconnected from plunger seals.

Tray P-4:
35 cc syringes w/caps (2), labeled Concentrate Syringe-A and Concentrate Syringe-B, having fixed plunger rods that are blue.

35 cc syringes w/caps (2), labeled Adipocyte Syringe-Y and Adipocyte Syringe-Z, having fixed plunger rods that are yellow.

1 cc Syringes (2)
Transfer-hubs (2)

Steps Required for 2.0 Tissue Augmentation Protocol

Note: The healthcare practitioner(s) performing all or any portion of the following steps is (are) to properly prepare and be outfitted for sterile use of packaging frame, tray(s) and/or component(s) (as the case may be) unless all or any portion of a particular step is addressed to "[non-sterile healthcare practitioner]" in which case sterile healthcare practitioner may not perform the step (or portion thereof) so noted.

Step 1: Set-Up Phase—Set Up Sterile Work-Area (a) (i) [Non-sterile healthcare practitioner] open preparation sub-kit wrapping (which acts as the sterile barrier for the packaging frame) so that sterile healthcare practitioner can reach in and move sterile packaging frame to sterile field; alternatively, (ii) [Non-sterile healthcare practitioner] open preparation sub-kit wrapping and remove protective cover from packaging frame so that sterile healthcare practitioner can reach in and move sterile trays to sterile field; alternatively, (iii) [Non-sterile healthcare practitioner] open preparation sub-kit wrapping, remove protective cover from packaging frame, remove each tray when directed by sterile healthcare practitioner. (Do not set trays on sterile field.) Remove protective seal from each tray when directed by sterile healthcare practitioner and either allow sterile healthcare practitioner to reach in and remove sterile components or dump contents of tray onto sterile field as directed by sterile healthcare practitioner. Be careful not to touch components or any part of tray protected by protective seal. Place Tray P-2 in incubating rocker when empty and dispose of the other trays when empty.

The remaining steps of this protocol are set forth assuming that one of the first two of these three alternatives has been selected.

(b) Remove work-area cover from Tray P-1 and cover work area; then, place contents of Tray P-1 on work-area cover (which is sterile) and dispose of Tray P-1

(c) [Non-sterile healthcare practitioner] open and hold autoclave bags containing harvesting cannula, syringe rack, bio-disposal rack and injection cannula so that sterile healthcare practitioner can remove items for placement on work-area cover and/or sterile field as is appropriate. Syringe-rack mat (from Tray P-1) is to be placed below syringe rack.

(d) Place bio-disposal bag (from Tray P-1) over bio-disposal rack and then place assembly on work-area cover; hand protocol check-list to non-sterile healthcare practitioner for use in a non-sterile area.

(e) [Non-sterile healthcare practitioner] fill in appropriate information on protocol check-list, being sure to include a patient reference number (which does not directly disclose patient identity) that corresponds to patient's file.

Note that bio-disposal bag is only for collection of syringe contents (i.e., liquids) and is to be properly disposed of after each procedure—it is not to be used for any components or other items that could puncture bag.

Step 2: Set-Up Phase—Set Up Equipment (a) [Non-sterile healthcare practitioner] turn on incubating rocker power switch and adjust settings to a temperature of 37° C. and a tilt-level of 6.

(b) [Non-sterile healthcare practitioner] turn on centrifuge power switch (but do not start spinning of carrier), adjust settings to a speed of 2400 RPM (1020×g) and a break-force of 5.

(c) [Non-sterile healthcare practitioner] open autoclave bag(s) containing carrier inserts so that sterile healthcare practitioner can reach in and place them in centrifuge carrier.

Step 3: Harvesting Phase—Prepare Patient

Using sound medical judgment, patient's physician should include the following steps as a part of physician's protocol for preparing patient:

(a) Identify harvesting area(s);

(b) Prepare harvesting areas(s) using physician-provided sterile preparation;

(c) Anesthetize access site(s) using physician-provided anesthetic;

(d) Create access site(s) by incising skin with physician-provided scalpel; and, (e) Gently infuse patient's subcutaneous adipose tissue via access site(s) by injecting physician-provided solution which contains a mixture of saline, anesthetic and epinephrine.

Step 4: Harvesting Phase—Harvest Adipose Tissue

Using sound medical judgment, patient's physician should (i) allow sufficient time to elapse prior to harvesting adipose tissue (as judged by adequate skin blanching which is caused by epinephrine) so as to collect adipose tissue with as little blood in it as possible and (ii) proceed with the steps that follow:

(a) Remove caps from Preparation Syringes 1-4 (from Tray P-2) and Preparation Syringes 5-8 (from Tray P-3) and attach harvesting cannula to Preparation Syringe-1;

(b) Harvest adipose tissue via patient's access site(s), filling Preparation Syringe-1 to the bold red line located halfway up syringe barrel;

(c) Repeat process for Preparation Syringes 2-8 (doing so will result in 30 cc of prepared tissue for use in Step 11); and, (d) Place syringes in syringe rack when each is done and dispose of Tray P-3 (but keep Tray P-2 for use in Step 8).

Step 5: Preparation Phase—Centrifuge Harvested Adipose Tissue (a) [Non-sterile healthcare practitioner] open centrifuge lid.

(b) Twist plunger rods to remove them from Preparation Syringes 1-8 plunger seals.

(c) Place each Preparation Syringe barrel (with syringe-tip down) into each of the eight centrifuge carrier inserts.

(d) [Non-sterile healthcare practitioner] close centrifuge lid, set timer for 3 minutes, start cycle, and open lid at end of cycle.

Step 6: Preparation Phase—Transfer Post-Centrifugation Layers (a) [Non-sterile healthcare practitioner] remove preparation cold-block from refrigeration unit and open autoclave bag so that sterile healthcare practitioner can reach in and move preparation cold-block to the work-area cover.

(b) Connect Concentrate Syringe-A (from Tray P-4) to a transfer-hub (from Tray P-1).

(c) Remove Preparation Syringe-1 from centrifuge carrier insert and reconnect a gray plunger rod to plunger seal (holding Syringe-1 vertical with syringe-tip down so as not to disturb layers that separate during centrifugation).

(d) Carefully remove cap and connect to transfer-hub on Concentrate Syringe-A (while maintaining position of Preparation Syringe-1 so as not to disturb separated layers).

(e) Gently flick tip of Preparation Syringe-1 to break up tissue concentrate which may have adhered to the plastic.

(f) Carefully transfer into Concentrate Syringe-A bottom layer of Preparation Syringe-1 (which is referred to as Tissue Concentrate) and a minute amount of solution from just above it (which is referred to as Aqueous Solution).

(g) Disconnect Concentrate Syringe-A from transfer-hub, cap it, and place it in preparation cold-block with syringe-tip down.

(h) Expel Aqueous Solution from Preparation Syringe-1 (which still has transfer-hub connected) into bio-disposal bag, except for a minute amount of Aqueous Solution just below suspended layer above (which is referred to as Parenchyma).

(i) Hold Adipocyte Syringe-Y (from Tray P-4) below Preparation Syringe-1 and connect to transfer-hub (continuing to hold Preparation Syringe-1 vertical with syringe-tip down).

(j) Gently transfer enough Parenchyma to fill Adipocyte Syringe-Y to first bold black line, then remove Adipocyte Syringe-Y from transfer-hub, cap it, and place it in into preparation cold-block with syringe-tip down.

(k) Expel remainder of Preparation Syringe-1 contents into bio-disposal bag, remove transfer-hub then place it in syringe rack with syringe-tip down.

(l) Repeat Step 6(c) through Step 6(k) but transfer enough Parenchyma from Preparation Syringe-2 to fill Adipocyte Syringe-Y to second bold black line.

(m) Repeat Step 6(c) through Step 6(k) but transfer enough Parenchyma from Preparation Syringe-3 to fill Adipocyte Syringe-Z to first bold black line.

(n) Repeat Step 6(m) but transfer enough Parenchyma from Preparation Syringe-4 to fill Adipocyte Syringe-Z to second bold black line. When done (i) Adipocyte Syringe-Y and Adipocyte Syringe-Z will be slightly less than half full (i.e., filled to level of second bold black line), (ii) Concentrate Syringe-A will contain Tissue Concentrate from Preparation Syringes 1-4, and (iii) Preparation Syringes 1-4 will be empty.

(o) Repeat Step 6(c) through Step 6(k) but connect a transfer-hub to Preparation Syringe-5 and carefully transfer (i) Tissue Concentrate into Concentrate Syringe-B and (ii) enough Parenchyma from Preparation Syringe-5 to fill Preparation Syringes-1 to first bold black line.

(p) Repeat Step 6(o) but transfer enough Parenchyma from Preparation Syringe-6 to fill Preparation Syringe-1 to second bold black line.

(q) Repeat Step 6(p) but transfer enough Parenchyma from Preparation Syringe-7 to fill Preparation Syringe-2 to first bold black line.

(r) Repeat Step 6(q) but transfer enough Parenchyma from Preparation Syringe-8 to fill Preparation Syringe-2 to second bold black line. When done, (i) Concentrate Syringe-B will contain Tissue Concentrate from Preparation Syringes 5-8, (ii) Preparation Syringes 1-2 will be filled to second bold black line with Parenchyma, and (iii) Preparation Syringe 3-8 will be empty. Dispose of Preparation Syringe 5-8 but attach transfer-hubs to Preparation Syringes 3-4 and save them for use in Step 9).

Step 7: Preparation Phase—Combine Parenchyma and Tissue Concentrate (a) Hold Concentrate Syringe-A with syringe-tip up, remove cap and connect transfer-hub.

(b) Hold Preparation Syringe-1 above Concentrate Syringe-A and connect it to transfer-hub. Gently transfer Parenchyma into Concentrate Syringe-A then remove Concentrate Syringe-A from transfer-hub and cap it. Keep Preparation Syringe-1 with transfer-hub connected for use in Step 9.

(c) Repeat Step 7(b) but transfer Parenchyma from Preparation Syringe 2 into Concentrate Syringe-B. Keep Preparation Syringe-2 with transfer-hub connected for use in Step 9.

Step 8: Preparation Phase—Incubate Parenchyma and Tissue Concentrate (a) [Non-sterile healthcare practitioner] open incubating rocker and mark protocol check-list in space provided to indicate current time.

(b) Place Tray P-2 in incubating rocker.

(c) Gently rock Concentrate Syringes back-and-forth to thoroughly mix then place on Tray P-2 in incubating rocker.

(d) [Non-sterile healthcare practitioner] close lid, set timer for 20 minutes, start cycle and, at end of cycle, open lid.

Step 9: Preparation Phase—Centrifuge Incubated Parenchyma (a) Remove Concentrate Syringe-A from incubating rocker, hold it with syringe-tip up, remove cap, and connect to transfer-hub on Preparation Syringe-1.

(b) Transfer half the contents of Concentrate Syringe-A into Preparation Syringe-1. Remove Preparation Syringe-1 from transfer-hub, cap it, and place in syringe rack.

(c) Repeat 9(b) for Preparation Syringe-2. When done, also place Concentrate Syringe-A in syringe rack.

(d) Repeat step 9(a) through 9(c) but Remove Concentrate Syringe-B from incubating rocker and transfer its contents into Preparation Syringe-3 and Preparation Syringe-4. After removing Preparation Syringe-4, dispose of Concentrate Syringe-B.

(e) Disconnect plunger rods from plunger seals of Preparation Syringes 1-4 and place syringe barrels in centrifuge carrier inserts with syringe-tips down.

(f) [Non-sterile healthcare practitioner] close centrifuge lid, set timer for 3 minutes, start cycle, and open lid at end of cycle. Dispose of Tray P-2.

Step 10: Preparation Phase—Recombine Tissue Concentrate with Adipocytes (a) Remove Adipocyte Syringe-Y from preparation cold-block, hold with syringe-tip up, remove cap, and connect transfer-hub.

(b) Remove Preparation Syringe-1 from centrifuge carrier insert and reconnect plunger rod to plunger seal (hold it vertical with syringe-tip down so as not to disturb layers that separate during centrifugation).

(c) Carefully remove cap and connect to transfer-hub on Adipocyte Syringe-Y (maintaining position of Preparation Syringe-1 so as not to disturb layers).

(d) Gently flick tip of Preparation Syringe-1 to break up tissue concentrate which may have adhered to the plastic.

(e) Gently transfer Tissue Concentrate from Preparation Syringe-1 and a minute amount of the liquid from just above it.

(f) Remove Preparation Syringe-1 from transfer-hub and properly dispose of it (with remaining liquid still inside).

(g) Repeat Step 10(b) through 10(f) but transfer Tissue Concentrate from Preparation Syringes 2 into Adipocyte Syringe-Y.

(h) Remove transfer-hub from Adipocyte Syringe-Y, cap it, and place it on work-surface cover.

(i) Remove Adipocyte Syringe-Z from preparation cold-block, hold with syringe tip up, remove cap, and connect transfer-hub.

(j) Repeat Step 10(b) through 10(f) but transfer Tissue Concentrate from Preparation Syringe-3 and Preparation Syringe-4 into Adipocyte Syringe-Z.

(k) Remove transfer-hub from Adipocyte Syringe-Z, cap it, and place it on work-surface cover. When done, Adipocyte Syringe-Y and Adipocyte Syringe-Z will each contain equal amounts of Parenchyma that has not been incubated and (ii) equal amounts of Tissue Concentrate from all Preparation Syringes.

(l) Remove Concentrate Syringe-A from preparation cold-block, remove cap, and connect transfer-hub.

(m) Gently rock Adipocyte Syringe-Y to mix contents, remove cap, and connect it to transfer-hub on Concentrate Syringe-A.

(n) Gently transfer contents of Adipocyte Syringe-Y into Concentrate Syringe-A then back into Adipocyte Syringe-Y.

(o) Remove Adipocyte Syringe-Y from transfer-hub on Concentrate Syringe-A and cap it.

(p) Repeat Step 10(m) through 10(o) but with Adipocyte Syringe-Z.

(q) Dispose of Concentrate Syringe-A.

Step 11: Utilization Phase—Utilize Recombined Tissue Concentrate and Adipocytes (a) Connect transfer-hub to 1 cc syringe (from Tray P-4) or to an alternative syringe provided by physician.

(b) Connect Adipocyte Syringe-Y to transfer-hub on injection syringe then transfer enough prepared adipose tissue to fill 1 cc syringe (or alternative syringe provided by physician).

(c) Remove syringe from transfer-hub on Adipocyte Syringe-Y and attach injection cannula (or an alternative injection cannula of physician's preference).

(d) If physician has clinical assistance, then a second syringe can be attached to Adipocyte Syringe-Y using transfer-hub and an additional portion of prepared adipose tissue in Adipocyte Syringe-Y can be transferred into second syringe.

(e) Prepared adipose tissue in both Adipocyte Syringe-Y and Adipocyte Syringe-Z can be transferred and utilized as determined by physician.

(f) When physician is finished, mark protocol check-list in space provided to indicate current time.

(g) Properly dispose of bio-disposal bag and all remaining 2.0 Tissue Augmentation Kit components and packaging.

(h) Autoclave harvesting cannula, syringe rack, bio-disposal rack, centrifuge carrier inserts, preparation cold-block, and injection cannula. Place preparation cold-block back into refrigeration unit.

Example 3

Reviticell Kit 2.0-S Tissue Augmentation Protocol

General Notes

The purpose of this 2.0-S Tissue Augmentation Protocol is to prepare and utilize a patient's adipose tissue at the time of patient's procedure for therapeutic use. Universal strict sterile technique is required during this protocol which is comprised of eleven annotated steps in four phases as follows:

Set-up phase to lay out components and set up equipment;
Harvesting phase to remove adipose tissue from patient;
Preparation phase to concentrate select portions of adipose tissue; and,
Utilization phase to utilize prepared adipose tissue to treat donor patient.

This 2.0-S Tissue Augmentation Protocol requires use of a 2.0-S Tissue Augmentation Kit which includes two sub-kits as follows:

(1) Preparation sub-kit which is comprised of a sterile packaging frame with four sterile trays. These trays contain sterile components used during certain steps of this protocol as indicated in the instructions for use. After discarding any packing-and-shipping materials, this sub-kit is to be stored (unopened in its protective wrapping) in a safe, secure and convenient place that is not subject to high temperatures.

(2) Solutions sub-kit which contains sterile vials of sterile saline. After discarding any packing-and-shipping materials, this sub-kit is to be stored (unopened in its protective wrapping) in a safe, secure and convenient place that is not subject to high temperatures (preferably with or near to preparation sub-kit storage).

If any part or component of the 2.0-S Tissue Augmentation Kit is damaged or missing, the point of purchase should be notified so that which has been damaged or is missing can be replaced. In no event should a damaged component be used nor should any substitutions be made for any missing components.

The 2.0-S Tissue Augmentation Kit is to be used with the ancillary equipment as follows.

Preparation cold-block that is to be used during this protocol to maintain a cold temperature for Adipocyte Syringes and Concentrate Syringes (later described). Preparation cold-block is to be autoclaved after each procedure and placed into a refrigeration unit (in unopened autoclave bag).

A small centrifuge that spins 8 carrier inserts horizontally which is to be operated at a speed of 2400 RPM (1020×g) and a break-force of 5 for three minutes (in each instance when called for).

Eight centrifuge carrier inserts (with syringe adapters) that are to be autoclaved after each procedure.

An incubating rocker which is to be operated at temperature of 37° C. and a tilt-level of 6 for twenty minutes (in each instance when called for).

A syringe rack that is to be autoclaved after each procedure.

A bio-disposal rack that is to be autoclaved after each procedure.

A harvesting cannula that is to be autoclaved after each procedure.

An injection cannula that is to be autoclaved after each procedure.

Sub-Kit Component Details

The 2.0-S Preparation Sub-Kit is comprised of a sterile packaging frame that houses four sterile trays containing the sterile components as identified below.

Tray P-1:
Work-area cover
Instructions for use
Protocol check-list
Syringe-rack mat
Bio-disposal bag
Vial-to-syringe adapters (8)

Tray P-2:
35 cc syringes w/caps (4), labeled Preparation Syringe-1, Preparation Syringe-2, Preparation Syringe-3 and Preparation Syringe-4, having gray plunger rods that can be disconnected from each respective plunger seal with a twisting motion (to maintain sterility of syringe contents during centrifugation).

Tray P-3:
35 cc syringes w/caps labeled (4), Preparation Syringe-5, Preparation Syringe-6, Preparation Syringe-7 and Preparation Syringe-8, having gray plunger rods that can be disconnected from plunger seals.

Tray P-4:
35 cc syringes w/caps (2), labeled Concentrate Syringe-A and Concentrate Syringe-B, having fixed plunger rods that are blue.

35 cc syringes w/caps (2), labeled Adipocyte Syringe-Y and Adipocyte Syringe-Z, having fixed plunger rods that are yellow.

1 cc Syringes (2)
Transfer-hubs (4)

The 2.0-S Solutions Sub-Kit contains the sterile components identified below.
Instructions for Use
20 cc vials of sterile saline (8)

Steps Required for 2.0-S Tissue Augmentation Protocol

Note: The healthcare practitioner(s) performing all or any portion of the following steps is (are) to properly prepare and be outfitted for sterile use of packaging frame, tray(s) and/or component(s) (as the case may be) unless all or any portion of a particular step is addressed to "[non-sterile healthcare practitioner]" in which case sterile healthcare practitioner may not perform the step (or portion thereof) so noted.

Step 1: Set-Up Phase—Set Up Sterile Work-Area (a) (i) [Non-sterile healthcare practitioner] open preparation sub-kit wrapping (which acts as the sterile barrier for the packaging frame) so that sterile healthcare practitioner can reach in and move sterile packaging frame to sterile field; alternatively, (ii) [Non-sterile healthcare practitioner] open preparation sub-kit wrapping and remove protective cover from packaging frame so that sterile healthcare practitioner can reach in and move sterile trays to sterile field; alternatively, (iii) [Non-sterile healthcare practitioner] open preparation sub-kit wrapping, remove protective cover from packaging frame, remove each tray when directed by sterile healthcare practitioner. (Do not set trays on sterile field.) Remove protective seal from each tray when directed by sterile healthcare practitioner and either allow sterile healthcare practitioner to reach in and remove sterile components or dump contents of tray onto sterile field as directed by sterile healthcare practitioner. Be careful not to touch components or any part of tray protected by protective seal. Place Tray P-2 in incubating rocker when empty and dispose of the other trays when empty.

The remaining steps of this protocol are set forth assuming that one of the first two of these three alternatives has been selected.

(b) Remove work-area cover from Tray P-1 and cover work area; then, place contents of Tray P-1 on work-area cover (which is sterile) and dispose of Tray P-1

(c) [Non-sterile healthcare practitioner] open and hold autoclave bags containing harvesting cannula, syringe rack, bio-disposal rack and injection cannula so that sterile healthcare practitioner can remove items for placement on work-area cover and/or sterile field as is appropriate. Syringe-rack mat (from Tray P-1) is to be placed below syringe rack.

(d) Place bio-disposal bag (from Tray P-1) over bio-disposal rack and then place assembly on work-area cover; hand protocol check-list to non-sterile healthcare practitioner for use in a non-sterile area.

(e) [Non-sterile healthcare practitioner] fill in appropriate information on protocol check-list, being sure to include a patient reference number (which does not directly disclose patient identity) that corresponds to patient's file.

Note that bio-disposal bag is only for collection of syringe contents (i.e., liquids) and is to be properly disposed of after each procedure—it is not to be used for any components or other items that could puncture bag.

Step 2: Set-Up Phase—Set Up Equipment (a) [Non-sterile healthcare practitioner] turn on incubating rocker power switch and adjust settings to a temperature of 37° C. and a tilt-level of 6.

(b) [Non-sterile healthcare practitioner] turn on centrifuge power switch (but do not start spinning of carrier), adjust settings to a speed of 2400 RPM (1020×g) and a break-force of 5.

(c) [Non-sterile healthcare practitioner] open autoclave bag(s) containing carrier inserts so that sterile healthcare practitioner can reach in and place them in centrifuge carrier.

Step 3: Harvesting Phase—Prepare Patient

Using sound medical judgment, patient's physician should include the following steps as a part of physician's protocol for preparing patient:

(a) Identify harvesting area(s);
(b) Prepare harvesting areas(s) using physician-provided sterile preparation;
(c) Anesthetize access site(s) using physician-provided anesthetic;
(d) Create access site(s) by incising skin with physician-provided scalpel; and,
(e) Gently infuse patient's subcutaneous adipose tissue via access site(s) by injecting physician-provided solution which contains a mixture of saline, anesthetic and epinephrine.

Step 4: Harvesting Phase—Harvest Adipose Tissue

Using sound medical judgment, patient's physician should (i) allow sufficient time to elapse prior to harvesting adipose tissue (as judged by adequate skin blanching which is caused by epinephrine) so as to collect adipose tissue with as little blood in it as possible and (ii) proceed with the steps that follow:

(a) Remove caps from Preparation Syringes 1-4 (from Tray P-2) and Preparation Syringes 5-8 (from Tray P-3) and attach harvesting cannula to Preparation Syringe-1;

(b) Harvest adipose tissue via patient's access site(s), filling Preparation Syringe-1 to the bold red line located halfway up syringe barrel;

(c) Repeat process for Preparation Syringes 2-8 (doing so will result in 30 cc of prepared tissue for use in Step 11); and, (d) Place syringes in syringe rack when each is done and dispose of Tray P-3 (but keep Tray P-2 for use in Step 8).

Step 5: Preparation Phase—Centrifuge Harvested Adipose Tissue (a) [Non-sterile healthcare practitioner] open centrifuge lid.

(b) [Non-sterile healthcare practitioner] open solutions sub-kit so that either (i) sterile healthcare practitioner can reach in and remove sterile contents and place them on work-area cover or (ii) dump sterile contents onto work-area cover (being careful not to touch sterile components).

(c) Place tip of vial-to-syringe adapter (from Tray P-1) on seal of first sterile saline vial (from solutions sub-kit) and apply pressure so that tip penetrates seal. Repeat process using a vial-to-syringe adapter for each vial of sterile saline.

(d) Connect Preparation Syringe-1 to vial-to-syringe adapter on first sterile saline vial.

(e) Draw sterile saline into Preparation Syringe-1 until filled.

(f) Disconnect Preparation Syringe-1 from vial-to-syringe adapter (which is attached to sterile saline vial) while holding syringe-tip up; dispose of empty vial and vial-to-syringe adapter.

(g) Put cap on Preparation Syringe-1 and twist plunger rod to remove it from plunger seal.

(h) Place Preparation Syringe-1 barrel into a centrifuge carrier insert (with syringe-tip down).

(i) Repeat Steps 5(c) through 5(h) for remaining seven Preparation Syringes.

(j) [Non-sterile healthcare practitioner] close centrifuge lid, set timer for 3 minutes, start cycle, and open lid at end of cycle.

Step 6: Preparation Phase—Transfer Post-Centrifugation Layers (a) [Non-sterile healthcare practitioner] remove preparation cold-block from refrigeration unit and open autoclave bag so that sterile healthcare practitioner can reach in and move preparation cold-block to the work-area cover.

(b) Connect Concentrate Syringe-A (from Tray P-4) to a transfer-hub (from Tray P-4).

(c) Remove Preparation Syringe-1 from centrifuge carrier insert and reconnect a gray plunger rod to plunger seal (holding Syringe-1 vertical with syringe-tip down so as not to disturb layers that separate during centrifugation).

(d) Carefully remove cap and connect to transfer-hub on Concentrate Syringe-A (while maintaining position of Preparation Syringe-1 so as not to disturb separated layers).

(e) Gently flick tip of Preparation Syringe-1 to break up tissue concentrate which may have adhered to the plastic.

(f) Carefully transfer into Concentrate Syringe-A bottom layer of Preparation Syringe-1 (which is referred to as Tissue Concentrate) and a minute amount of solution from just above it (which is referred to as Aqueous Solution).

(g) Disconnect Concentrate Syringe-A from transfer-hub, cap it, and place it in preparation cold-block with syringe-tip down.

(h) Expel Aqueous Solution from Preparation Syringe-1 (which still has transfer-hub connected) into bio-disposal bag, except for a minute amount of Aqueous Solution just below suspended layer above (which is referred to as Parenchyma).

(i) Hold Adipocyte Syringe-Y (from Tray P-4) below Preparation Syringe-1 and connect to transfer-hub (continuing to hold Preparation Syringe-1 vertical with syringe-tip down).

(j) Gently transfer enough Parenchyma to fill Adipocyte Syringe-Y to first bold black line, then remove Adipocyte Syringe-Y from transfer-hub, cap it, and place it in into preparation cold-block with syringe-tip down.

(k) Expel remainder of Preparation Syringe-1 contents into bio-disposal bag, remove transfer-hub then place it in syringe rack with syringe-tip down.

(l) Repeat Step 6(c) through Step 6(k) but transfer enough Parenchyma from Preparation Syringe-2 to fill Adipocyte Syringe-Y to second bold black line.

(m) Repeat Step 6(c) through Step 6(k) but transfer enough Parenchyma from Preparation Syringe-3 to fill Adipocyte Syringe-Z to first bold black line.

(n) Repeat Step 6(m) but transfer enough Parenchyma from Preparation Syringe-4 to fill Adipocyte Syringe-Z to second bold black line. When done (i) Adipocyte Syringe-Y and Adipocyte Syringe-Z will be slightly less than half full (i.e., filled to level of second bold black line), (ii) Concentrate Syringe-A will contain Tissue Concentrate from Preparation Syringes 1-4, and (iii) Preparation Syringes 1-4 will be empty.

(o) Repeat Step 6(c) through Step 6(k) but connect a transfer-hub to Preparation Syringe-5 and carefully transfer (i) Tissue Concentrate into Concentrate Syringe-B and (ii) enough Parenchyma from Preparation Syringe-5 to fill Preparation Syringes-1 to first bold black line.

(p) Repeat Step 6(o) but transfer enough Parenchyma from Preparation Syringe-6 to fill Preparation Syringe-1 to second bold black line.

(q) Repeat Step 6(p) but transfer enough Parenchyma from Preparation Syringe-7 to fill Preparation Syringe-2 to first bold black line.

(r) Repeat Step 6(q) but transfer enough Parenchyma from Preparation Syringe-8 to fill Preparation Syringe-2 to second bold black line. When done, (i) Concentrate Syringe-B will contain Tissue Concentrate from Preparation Syringes 5-8, (ii) Preparation Syringes 1-2 will be filled to second bold black line with Parenchyma, and (iii) Preparation Syringe 3-8 will be empty. Dispose of Preparation Syringe 5-8 but attach transfer-hubs to Preparation Syringes 3-4 and save them for use in Step 9).

Step 7: Preparation Phase—Combine Parenchyma and Tissue Concentrate (a) Hold Concentrate Syringe-A with syringe-tip up, remove cap and connect transfer-hub.

(b) Hold Preparation Syringe-1 above Concentrate Syringe-A and connect it to transfer-hub. Gently transfer Parenchyma into Concentrate Syringe-A then remove Concentrate Syringe-A from transfer-hub and cap it. Keep Preparation Syringe-1 with transfer-hub connected for use in Step 9.

(c) Repeat Step 7(b) but transfer Parenchyma from Preparation Syringe 2 into Concentrate Syringe-B. Keep Preparation Syringe-2 with transfer-hub connected for use in Step 9.

Step 8: Preparation Phase—Incubate Parenchyma and Tissue Concentrate (a) [Non-sterile healthcare practitioner] open incubating rocker and mark protocol check-list in space provided to indicate current time.

(b) Place Tray P-2 in incubating rocker.

(c) Gently rock Concentrate Syringes back-and-forth to thoroughly mix then place on Tray P-2 in incubating rocker.

(d) [Non-sterile healthcare practitioner] close lid, set timer for 20 minutes, start cycle and, at end of cycle, open lid.

Step 9: Preparation Phase—Centrifuge Incubated Parenchyma (a) Remove Concentrate Syringe-A from incubating rocker, hold it with syringe-tip up, remove cap, and connect to transfer-hub on Preparation Syringe-1.

(b) Transfer half the contents of Concentrate Syringe-A into Preparation Syringe-1. Remove Preparation Syringe-1 from transfer-hub, cap it, and place in syringe rack.

(c) Repeat 9(b) for Preparation Syringe-2. When done, also place Concentrate Syringe-A in syringe rack.

(d) Repeat step 9(a) through 9(c) but Remove Concentrate Syringe-B from incubating rocker and transfer its contents into Preparation Syringe-3 and Preparation Syringe-4. After removing Preparation Syringe-4, dispose of Concentrate Syringe-B.

(e) Disconnect plunger rods from plunger seals of Preparation Syringes 1-4 and place syringe barrels in centrifuge carrier inserts with syringe-tips down.

(f) [Non-sterile healthcare practitioner] close centrifuge lid, set timer for 3 minutes, start cycle, and open lid at end of cycle. Dispose of Tray P-2.

Step 10: Preparation Phase—Recombine Tissue Concentrate with Adipocytes (a) Remove Adipocyte Syringe-Y from preparation cold-block, hold with syringe-tip up, remove cap, and connect transfer-hub.

(b) Remove Preparation Syringe-1 from centrifuge carrier insert and reconnect plunger rod to plunger seal (hold it vertical with syringe-tip down so as not to disturb layers that separate during centrifugation).

(c) Carefully remove cap and connect to transfer-hub on Adipocyte Syringe-Y (maintaining position of Preparation Syringe-1 so as not to disturb layers).

(d) Gently flick tip of Preparation Syringe-1 to break up tissue concentrate which may have adhered to the plastic.

(e) Gently transfer Tissue Concentrate from Preparation Syringe-1 and a minute amount of the liquid from just above it.

(f) Remove Preparation Syringe-1 from transfer-hub and properly dispose of it (with remaining liquid still inside).

(g) Repeat Step 10(b) through 10(f) but transfer Tissue Concentrate from Preparation Syringes 2 into Adipocyte Syringe-Y.

(h) Remove transfer-hub from Adipocyte Syringe-Y, cap it, and place it on work-surface cover.

(i) Remove Adipocyte Syringe-Z from preparation cold-block, hold with syringe tip up, remove cap, and connect transfer-hub.

(j) Repeat Step 10(b) through 10(f) but transfer Tissue Concentrate from Preparation Syringe-3 and Preparation Syringe-4 into Adipocyte Syringe-Z.

(k) Remove transfer-hub from Adipocyte Syringe-Z, cap it, and place on work-surface cover. When done, Adipocyte Syringe-Y and Adipocyte Syringe-Z will each contain equal amounts of Parenchyma that has not been incubated and (ii) equal amounts of Tissue Concentrate from all Preparation Syringes.

(l) Remove Concentrate Syringe-A from preparation cold-block, remove cap, and connect transfer-hub.

(m) Gently rock Adipocyte Syringe-Y to mix contents, remove cap, and connect it to transfer-hub on Concentrate Syringe-A.

(n) Gently transfer contents of Adipocyte Syringe-Y into Concentrate Syringe-A then back into Adipocyte Syringe-Y.

(o) Remove Adipocyte Syringe-Y from transfer-hub on Concentrate Syringe-A and cap it.

(p) Repeat Step 10(m) through 10(o) but with Adipocyte Syringe-Z.

(q) Dispose of Concentrate Syringe-A.

Step 11: Utilization Phase—Utilize Recombined Tissue Concentrate and Adipocytes (a) Connect transfer-hub to 1 cc syringe (from Tray P-4) or to an alternative syringe provided by physician.

(b) Connect Adipocyte Syringe-Y to transfer-hub on injection syringe then transfer enough prepared adipose tissue to fill 1 cc syringe (or alternative syringe provided by physician).

(c) Remove syringe from transfer-hub on Adipocyte Syringe-Y and attach injection cannula (or an alternative injection cannula of physician's preference).

(d) If physician has clinical assistance, then a second syringe can be attached to Adipocyte Syringe-Y using transfer-hub and an additional portion of prepared adipose tissue in Adipocyte Syringe-Y can be transferred into second syringe.

(e) Prepared adipose tissue in both Adipocyte Syringe-Y and Adipocyte Syringe-Z can be transferred and utilized as determined by physician.

(f) When physician is finished, mark protocol check-list in space provided to indicate current time.

(g) Properly dispose of bio-disposal bag and all remaining 2.0-S Tissue Augmentation Kit components and packaging.

(h) Autoclave harvesting cannula, syringe rack, bio-disposal rack, centrifuge carrier inserts, preparation cold-block, and injection cannula. Place preparation cold-block back into refrigeration unit.

Example 4

Reviticell Kit 3.0 Tissue Augmentation Protocol

General Notes

This 3.0 Tissue Augmentation Protocol includes two distinct sub-protocols as set forth below.

(1) Preoperative Protocol:

To reconstitute (hydrate) an enzymatic reagent and distribute it into hydration vials prior to a patient's procedure. Aseptic technique is required during the preoperative protocol which is comprised of four annotated steps.

(2) Operative Protocol:

To prepare and utilize a patient's adipose tissue at the time of patient's procedure for therapeutic use. Universal strict sterile technique is required during this protocol which is comprised of twelve annotated steps in four phases as follows:

Set-up phase to lay out components and set up equipment;
    Harvesting phase to remove adipose tissue from patient;
    Preparation phase to concentrate select portions of adipose tissue; and,
    Utilization phase to utilize prepared adipose tissue to treat donor patient.

This 3.0 Tissue Augmentation Protocol requires use of a 3.0 Tissue Augmentation Kit which includes four sub-kits as follows:

(1) Reagent sub-kit for use during pre-operative protocol which is comprised of a package with two canisters each of which contains a vial of sterile enzymatic reagent. After discarding any packing-and-shipping materials, this sub-kit is to be stored (unopened in its protective wrapping) in the freezer unit provided as a part of the equipment later described.

(2) Hydration sub-kit for use during pre-operative protocol which is comprised of a packaging frame with two trays. Tray H-1 contains components (some of which are sterile) needed to reconstitute (hydrate) an enzymatic reagent. Tray H-2 contains hydration vials with sterile interiors into which enzymatic reagent is to be distributed. After discarding any packing-and-shipping materials, this sub-kit is to be stored (unopened in its protective wrapping) in the refrigeration unit provided as a part of the equipment later described.

(3) Preparation sub-kit for use during operative protocol which is comprised of a sterile packaging frame with four sterile trays. These trays contain sterile components used during certain steps of this protocol as indicated in the instructions for use. After discarding any packing-and-shipping materials, this sub-kit is to be stored (unopened in its protective wrapping) in a safe, secure and convenient place that is not subject to high temperatures.

(4) Solutions sub-kit for use during operative protocol which contains sterile vials of sterile saline. After discarding any packing-and-shipping materials, this sub-kit is to be stored (unopened in its protective wrapping) in a safe, secure and convenient place that is not subject to high temperatures (preferably with or near to preparation sub-kit storage).

If any part or component of the 3.0 Tissue Augmentation Kit is damaged or missing, the point of purchase should be notified so that which has been damaged or is missing can be replaced. In no event should a damaged component be used nor should any substitutions be made for any missing components.

The 3.0 Tissue Augmentation Kit is to be used with the ancillary equipment as follows.

- A small, pharmaceutical-grade freezer unit and refrigeration unit (which may be one device or separate devices).
- A pre-op cold-block that is to be used during preoperative protocol to maintain cold temperature of hydration vials into which hydrated enzymatic reagent is to be distributed. Pre-op cold-block is to be autoclaved and placed into refrigeration unit (in unopened autoclave bag).
- A Preparation cold-block that is to be used during this protocol to maintain a cold temperature for Adipocyte Syringes and Concentrate Syringes (later described). Preparation cold-block is to be autoclaved after each procedure and placed into a refrigeration unit (in unopened autoclave bag).
- A small centrifuge that spins 8 carrier inserts horizontally which is to be operated at a speed of 2400 RPM (1020×g) and a break-force of 5 for three minutes (in each instance when called for).
- Eight centrifuge carrier inserts (with syringe adapters) that are to be autoclaved after each procedure.
- An incubating rocker which is to be operated at temperature of 37° C. and a tilt-level of 6 for twenty minutes (in each instance when called for).
- A syringe rack that is to be autoclaved after each procedure.
- A bio-disposal rack that is to be autoclaved after each procedure.
- A harvesting cannula that is to be autoclaved after each procedure.
- An injection cannula that is to be autoclaved after each procedure.

Preoperative Protocol

Sub-Kit Component Details

The 3.0 Reagent Sub-Kit contains the components identified below.

Instructions for use

Two canisters that each contain a vial with 5 mg of sterile, GMP-rated, enzymatic reagent in a lyophilized form Hydration vial labels (20)

The 3.0 Hydration Sub-Kit is comprised of a packaging frame that houses two trays containing the components as identified below.

Tray H-1:
Work-area cover
Instructions for use
Re-sealable freezer bag
5 cc sterile syringe prefilled with sterile water
21 g needle
0.5 cc syringe with attached needle (2)
Tray H-2:
20 cc hydration vials (10) capped to seal the sterile interior Steps Required for 3.0 Pre-Operative Protocol Step 1: Set-Up Work-Area (a) Remove hydration sub-kit from refrigeration unit and open it to access Tray H-1 and Tray H-2.

(b) Open Tray H-1, remove syringe prefilled with sterile water and place it (unopened) in refrigeration unit along with Tray H-2.

(c) Remove work-area cover from Tray H-1 and position it on surface to be used for reconstituting and distributing enzymatic reagent into hydration vials.

(d) Remove remainder of Tray H-1 contents and place on work-area cover.

(e) Dispose of Tray H-1 and hydration sub-kit packaging materials.

Step 2: Reconstitute Enzymatic Reagent (a) Remove reagent sub-kit from freezer unit.

(b) Open reagent sub-kit, remove labels, and fill-in requested information.

(c) Remove pre-op cold-block from refrigeration unit and from autoclave bag; place it on work-area cover.

(d) Remove Tray H-2 from refrigeration unit, open it, remove vial holder with hydration vials, and place hydration vials in holes of pre-op cold-block (do not dispose of vial holder).

(e) Remove canisters from reagent sub-kit and remove vials of enzymatic reagent from canisters; dispose of Tray H-2 and reagent sub-kit packaging and canisters.

(f) Remove syringe prefilled with sterile water from refrigeration unit and attach 21 g needle (from Tray H-1).

(g) Inject 2.5 cc sterile water (half of syringe contents) into the first enzymatic reagent vial and swirl resulting reagent solution to thoroughly mix it.

(h) Repeat step 1(h) but using second half of sterile water for second enzymatic reagent vial.

Step 3: Transfer Reagent Solution (a) Use first 0.5 cc syringe with needle to draw in 0.5 cc reagent solution from first enzymatic reagent vial.

(b) Transfer contents of 0.5 cc syringe into first hydration vial (keep hydration vial in pre-op cold-block while doing so).

(c) Repeat Step 3(b) to transfer 0.5 cc reagent solution into 4 more hydration vials.

(d) Use second 0.5 cc syringe with needle to draw in 0.5 cc reagent solution from second enzymatic reagent vial.

(e) Transfer contents of 0.5 cc syringe into sixth hydration vial (keep hydration vial in pre-op cold-block while doing so).

(f) Repeat Step 3(e) to transfer 0.5 cc reagent solution final 4 hydration vials.

Step 4: Label and Store Hydration Vials (a) Move hydration vials (one at a time) from pre-op cold-block to vial holder (from Tray H-2) and affix one reagent label to each when doing so.

(b) Place vial holder with labeled hydration vials and remaining reagent labels (10) in re-sealable freezer bag and store in freezer unit. These 10 hydration vials will be used for 5 3.0 Tissue Augmentation procedures.

(c) Properly dispose of used components not otherwise to be stored in freezer unit.

(d) Autoclave pre-op cold-block and, when done, place it back into freezer in unopened autoclave bag.

Operative Protocol

Sub-Kit Component Details

The 3.0 Preparation Sub-Kit is Comprised of a Sterile Packaging Frame that Houses four sterile trays containing the sterile components as identified below.

Tray P-1:
Work-area cover
Instructions for use
Protocol check-list
Syringe-rack mat
Bio-disposal bag
Vial-to-syringe adapters (11)

Tray P-2:
35 cc syringes w/caps (4), labeled Preparation Syringe-1, Preparation Syringe-2, Preparation Syringe-3 and Preparation Syringe-4, having gray plunger rods that can be disconnected from each respective plunger seal with a twisting motion (to maintain sterility of syringe contents during centrifugation).
35 cc syringe with cap labeled Reagent Syringe-A, having a fixed plunger rod that is red.
21 g needles (2)

Tray P-3:
35 cc syringes w/caps labeled (4), Preparation Syringe-5, Preparation Syringe-6, Preparation Syringe-7 and Preparation Syringe-8, having gray plunger rods that can be disconnected from plunger seals.
35 cc syringe with cap labeled Reagent Syringe-B, having a fixed plunger rod that is red.

Tray P-4:
35 cc syringes w/caps (2), labeled Concentrate Syringe-A and Concentrate Syringe-B, having fixed plunger rods that are blue.
35 cc syringes w/caps (2), labeled Adipocyte Syringe-Y and Adipocyte Syringe-Z, having fixed plunger rods that are yellow.
1 cc Syringes (2)
Transfer-hubs (6)

The 2.0-S Solutions Sub-Kit contains the sterile components identified below.
Instructions for Use
20 cc vials of sterile saline (16)
15 cc vials of sterile buffer solution (2)

Steps Required for Operative Protocol

Note: The healthcare practitioner(s) performing all or any portion of the following steps is (are) to properly prepare and be outfitted for sterile use of packaging frame, tray(s) and/or component(s) (as the case may be) unless all or any portion of a particular step is addressed to "[non-sterile healthcare practitioner]" in which case sterile healthcare practitioner may not perform the step (or portion thereof) so noted.

Step 1: Set-Up Phase—Set Up Sterile Work-Area (a) (i) [Non-sterile healthcare practitioner] open preparation sub-kit wrapping (which acts as the sterile barrier for the packaging frame) so that sterile healthcare practitioner can reach in and move sterile packaging frame to sterile field; alternatively, (ii) [Non-sterile healthcare practitioner] open preparation sub-kit wrapping and remove protective cover from packaging frame so that sterile healthcare practitioner can reach in and move sterile trays to sterile field; alternatively, (iii)[Non-sterile healthcare practitioner] open preparation sub-kit wrapping, remove protective cover from packaging frame, remove each tray when directed by sterile healthcare practitioner. (Do not set trays on sterile field.) Remove protective seal from each tray when directed by sterile healthcare practitioner and either allow sterile healthcare practitioner to reach in and remove sterile components or dump contents of tray onto sterile field as directed by sterile healthcare practitioner. Be careful not to touch components or any part of tray protected by protective seal. Place Tray P-2 in incubating rocker when empty and dispose of the other trays when empty.

The remaining steps of this protocol are set forth assuming that one of the first two of these three alternatives has been selected.

(b) Remove work-area cover from Tray P-1 and cover work area; then, place contents of Tray P-1 on work-area cover (which is sterile) and dispose of Tray P-1

(c) [Non-sterile healthcare practitioner] open and hold autoclave bags containing harvesting cannula, syringe rack, bio-disposal rack and injection cannula so that sterile healthcare practitioner can remove items for placement on work-area cover and/or sterile field as is appropriate. Syringe-rack mat (from Tray P-1) is to be placed below syringe rack.

(d) Place bio-disposal bag (from Tray P-1) over bio-disposal rack and then place assembly on work-area cover; hand protocol check-list to non-sterile healthcare practitioner for use in a non-sterile area.

(e) [Non-sterile healthcare practitioner] fill in appropriate information on protocol check-list, being sure to include a patient reference number (which does not directly disclose patient identity) that corresponds to patient's file.

Note that bio-disposal bag is only for collection of syringe contents (i.e., liquids) and is to be properly disposed of after each procedure—it is not to be used for any components or other items that could puncture bag.

Step 2: Set-Up Phase—Set Up Equipment (a) [Non-sterile healthcare practitioner] turn on incubating rocker power switch and adjust settings to a temperature of 37° C. and a tilt-level of 6.

(b) [Non-sterile healthcare practitioner] turn on centrifuge power switch (but do not start spinning of carrier), adjust settings to a speed of 2400 RPM (1020×g) and a break-force of 5.

(c) [Non-sterile healthcare practitioner] open autoclave bag(s) containing carrier inserts so that sterile healthcare practitioner can reach in and place them in centrifuge carrier.

Step 3: Harvesting Phase—Prepare Patient

Using sound medical judgment, patient's physician should include the following steps as a part of physician's protocol for preparing patient:

(a) Identify harvesting area(s);

(b) Prepare harvesting areas(s) using physician-provided sterile preparation;

(c) Anesthetize access site(s) using physician-provided anesthetic;

(d) Create access site(s) by incising skin with physician-provided scalpel; and, (e) Gently infuse patient's subcutaneous adipose tissue via access site(s) by injecting physician-provided solution which contains a mixture of saline, anesthetic and epinephrine.

Step 4: Harvesting Phase—Harvest Adipose Tissue

Using sound medical judgment, patient's physician should (i) allow sufficient time to elapse prior to harvesting adipose tissue (as judged by adequate skin blanching which is caused by epinephrine) so as to collect adipose tissue with as little blood in it as possible and (ii) proceed with the steps that follow:

(a) Remove caps from Preparation Syringes 1-4 (from Tray P-2) and Preparation Syringes 5-8 (from Tray P-3) and attach harvesting cannula to Preparation Syringe-1;

(b) Harvest adipose tissue via patient's access site(s), filling Preparation Syringe-1 to the bold red line located halfway up syringe barrel;

(c) Repeat process for Preparation Syringes 2-8 (doing so will result in 30 cc of prepared tissue for use in Step 11); and, (d) Place syringes in syringe rack when each is done and dispose of Tray P-3 (but keep Tray P-2 for use in Step 8).

Step 5: Preparation Phase—Prepare Reagent Solution (a) [Non-sterile healthcare practitioner] remove two hydration vials and two reagent labels from re-sealable freezer bag in freezer and affix reagent labels to protocol check-list (the information on reagent labels affixed to hydration vials should be the same information as on reagent labels affixed to protocol check-list).

(b) [Non-sterile healthcare practitioner] open solutions sub-kit so that either (a) sterile healthcare practitioner can reach in and remove sterile contents and place them on work-area cover or (b) dump sterile contents onto work-area cover (being careful not to touch sterile components).

(c) Place tip of vial-to-syringe adapter (from Tray P-1) on seal of sterile buffer vial (from solutions sub-kit) and apply pressure so that tip penetrates seal.

(d) Connect Reagent Syringe-A (from Tray P-2) to vial-to-syringe adapter on sterile buffer vial and draw in buffer.

(e) Remove Reagent Syringe-A from vial-to-syringe adapter and attach first 21 g needle (from Tray P-2); dispose of sterile buffer vial and vial-to-syringe adapter.

(f) [Non-sterile healthcare practitioner] wipe rubber port of first hydration vial with physician-provided alcohol wipe; continue holding hydration vial while sterile healthcare practitioner injects solution using Reagent Syringe-A.

(g) [Non-sterile healthcare practitioner] gently swirl buffer solution to thaw frozen reagent solution; continue holding hydration vial while sterile healthcare practitioner uses Reagent Syringe-A to draw out all of combined solution.

(h) Remove 21 g needle from Reagent Syringe-A, cap it, and place on Tray P-2 (which is sitting on work-area cover).

(i) Repeat steps 5(a) through (5h) but use a new syringe-to-vial adapter (from Tray P-1), sterile buffer vial (from Solutions Sub-kit), Reagent Syringe-B (from Tray P-3), and second needle (from Tray P-2).

(j) Dispose of Tray P-3 and enzymatic reagent vials but save Tray P-2 for later use.

(k) [Non-sterile healthcare practitioner] open lid of incubating rocker and sterile healthcare practitioner place Tray P-2 (which contains Reagent Syringe-A and Reagent Syringe-B) on rocking-platform inside.

(l) [Non-sterile healthcare practitioner] close incubating rocker lid and set timer for 30 minutes so that the working solution of reagent and buffer have sufficient time to pre-warm until needed in Step 10.

Step 6: Preparation Phase—Centrifuge Harvested Adipose Tissue (a) [Non-sterile healthcare practitioner] open centrifuge lid.

(b) [Non-sterile healthcare practitioner] open solutions sub-kit so that either (i) sterile healthcare practitioner can reach in and remove sterile contents and place them on work-area cover or (ii) dump sterile contents onto work-area cover (being careful not to touch sterile components).

(c) Place tip of vial-to-syringe adapter (from Tray P-1) on seal of first sterile saline vial (from solutions sub-kit) and apply pressure so that tip penetrates seal. Repeat process using a vial-to-syringe adapter for each vial of sterile saline.

(d) Connect Preparation Syringe-1 to vial-to-syringe adapter on first sterile saline vial.

(e) Draw sterile saline into Preparation Syringe-1 until filled.

(f) Disconnect Preparation Syringe-1 from vial-to-syringe adapter (which is attached to sterile saline vial) while holding syringe-tip up; dispose of empty vial and vial-to-syringe adapter.

(g) Put cap on Preparation Syringe-1 and twist plunger rod to remove it from plunger seal.

(h) Place Preparation Syringe-1 barrel into a centrifuge carrier insert (with syringe-tip down).

(i) Repeat Steps 6(c) through 6(h) for remaining seven Preparation Syringes.

(j) [Non-sterile healthcare practitioner] close centrifuge lid, set timer for 3 minutes, start cycle, and open lid at end of cycle.

Step 7: Preparation Phase—Transfer Post-Centrifugation Layers (a) [Non-sterile healthcare practitioner] remove preparation cold-block from refrigeration unit and open autoclave bag so that sterile healthcare practitioner can reach in and move preparation cold-block to the work-area cover.

(b) Connect Concentrate Syringe-A (from Tray P-4) to a transfer-hub (from Tray P-4).

(c) Remove Preparation Syringe-1 from centrifuge carrier insert and reconnect a gray plunger rod to plunger seal (holding Syringe-1 vertical with syringe-tip down so as not to disturb layers that separate during centrifugation).

(d) Carefully remove cap and connect to transfer-hub on Concentrate Syringe-A (while maintaining position of Preparation Syringe-1 so as not to disturb separated layers).

(e) Gently flick tip of Preparation Syringe-1 to break up tissue concentrate which may have adhered to the plastic.

(f) Carefully transfer into Concentrate Syringe-A bottom layer of Preparation Syringe-1 (which is referred to as Tissue Concentrate) and a minute amount of solution from just above it (which is referred to as Aqueous Solution).

(g) Disconnect Concentrate Syringe-A from transfer-hub, cap it, and place it in preparation cold-block with syringe-tip down.

(h) Expel Aqueous Solution from Preparation Syringe-1 (which still has transfer-hub connected) into bio-disposal bag, except for a minute amount of Aqueous Solution just below suspended layer above (which is referred to as Parenchyma).

(i) Hold Adipocyte Syringe-Y (from Tray P-4) below Preparation Syringe-1 and connect to transfer-hub (continuing to hold Preparation Syringe-1 vertical with syringe-tip down).

(j) Gently transfer enough Parenchyma to fill Adipocyte Syringe-Y to first bold black line, then remove Adipocyte Syringe-Y from transfer-hub, cap it, and place it in into preparation cold-block with syringe-tip down.

(k) Expel remainder of Preparation Syringe-1 contents into bio-disposal bag, remove transfer-hub then place it in syringe rack with syringe-tip down.

(l) Repeat Step 7(c) through Step 7(k) but transfer enough Parenchyma from Preparation Syringe-2 to fill Adipocyte Syringe-Y to second bold black line.

(m) Repeat Step 7(c) through Step 7(k) but transfer enough Parenchyma from Preparation Syringe-3 to fill Adipocyte Syringe-Z to first bold black line.

(n) Repeat Step 7(m) but transfer enough Parenchyma from Preparation Syringe-4 to fill Adipocyte Syringe-Z to second bold black line. When done (i) Adipocyte Syringe-Y and Adipocyte Syringe-Z will be slightly less than half full (i.e., filled to level of second bold black line), (ii) Concentrate Syringe-A will contain Tissue Concentrate from Preparation Syringes 1-4, and (iii) Preparation Syringes 1-4 will be empty.

(o) Repeat Step 7(c) through Step 7(k) but connect a transfer-hub to Preparation Syringe-5 and carefully transfer (i) Tissue Concentrate into Concentrate Syringe-B and (ii) enough Parenchyma from Preparation Syringe-5 to fill Preparation Syringes-1 to first bold black line.

(p) Repeat Step 7(o) but transfer enough Parenchyma from Preparation Syringe-6 to fill Preparation Syringe-1 to second bold black line.

(q) Repeat Step 7(p) but transfer enough Parenchyma from Preparation Syringe-7 to fill Preparation Syringe-2 to first bold black line.

(r) Repeat Step 6(q) but transfer enough Parenchyma from Preparation Syringe-8 to fill Preparation Syringe-2 to second bold black line. When done, (i) Concentrate Syringe-B will contain Tissue Concentrate from Preparation Syringes 5-8, (ii) Preparation Syringes 1-2 will be filled to second bold black line with Parenchyma, and (iii) Preparation Syringe 3-8 will be empty. Dispose of Preparation Syringe 5-8 but attach transfer-hubs to Preparation Syringes 3-4 and save them for use in Step 10).

Step 8: Preparation Phase—Combine Parenchyma and Tissue Concentrate (a) Hold Concentrate Syringe-A with syringe-tip up, remove cap and connect transfer-hub.

(b) Hold Preparation Syringe-1 above Concentrate Syringe-A and connect it to transfer-hub. Gently transfer Parenchyma into Concentrate Syringe-A then remove Concentrate Syringe-A from transfer-hub and cap it. Keep Preparation Syringe-1 with transfer-hub connected for use in Step 10.

(c) Repeat Step 8(b) but transfer Parenchyma from Preparation Syringe 2 into Concentrate Syringe-B. Keep Preparation Syringe-2 with transfer-hub connected for use in Step 10.

Step 9: Preparation Phase—Incubate Parenchyma and Tissue Concentrate (a) [Non-sterile healthcare practitioner] open incubating rocker and mark protocol check-list in space provided to indicate current time.

(b) Connect transfer-hub to Concentrate Syringe-A.

(c) Connect Reagent Syringe-A (from incubating rocker) to transfer-hub.

(d) Gently transfer contents of Concentrate Syringe-A into Reagent Syringe-A.

(e) Remove Reagent Syringe-A from transfer-hub, cap it, and gently rock it back-and-forth to thoroughly mix.

(f) Place Reagent Syringe-A on Tray P-2 in incubating rocker.

(g) Repeat Step 9(a) through 9(f) but transfer contents of Concentrate Syringe-B into Reagent Syringe-B. Place Reagent Syringe-B on Tray P-2 in incubating rocker; place Concentrate Syringe-A in syringe-rack, and dispose of Concentrate Syringe-B.

(h) [Non-sterile healthcare practitioner] close lid, set timer for 20 minutes, start cycle and, at end of cycle, open lid.

Step 10: Preparation Phase—Centrifuge Incubated Parenchyma (a) Place tip of vial-to-syringe adapter (from Tray P-1) on seal of sterile saline vial (from solutions sub-kit) and apply pressure so that tip penetrates seal. Repeat process using a vial-to-syringe adapter for each remaining vial of sterile saline.

(b) Remove Reagent Syringe-A from incubating rocker, hold it with syringe-tip up, remove cap, and connect to transfer-hub on Preparation Syringe-1.

(c) Transfer one-quarter of Reagent Syringe-A contents into Preparation Syringe-1 (which will reduce the contents of Reagent Syringe-A to the first bold black line nearest top of the syringe barrel). Remove Preparation Syringe-1 from transfer-hub, cap it, and place in syringe-rack.

(d) Transfer next one-quarter of contents into Preparation Syringe-2 (which will reduce the contents of Reagent Syringe-A to the bold black line half-way down syringe barrel).

(e) Transfer next one-quarter of contents into Preparation Syringe-2 (which will reduce the contents of Reagent Syringe-A to the bold black line nearest the bottom of syringe barrel).

(f) Transfer final one-quarter of contents into Preparation Syringe-2.

(g) Repeat Step 10(b) through 10(f) but transfer contents of Reagent Syringe-B into Preparation Syringes 5-8.

(h) Connect Preparation Syringe-1 to vial-to-syringe adapter on first sterile saline vial.

(i) Draw sterile saline into Preparation Syringe-1 until filled.

(j) Disconnect Preparation Syringe-1 from vial-to-syringe adapter (which is attached to sterile saline vial) while holding syringe-tip up; dispose of empty vial and vial-to-syringe adapter.

(k) Put cap on Preparation Syringe-1 and invert twist plunger rod to remove it from plunger seal.

(l) Gently rock Preparation Syringe-1 syringe barrel back-and-forth, then place into a centrifuge carrier insert (with syringe-tip down).

(m) Repeat Steps 10(h) through 10(l) but for Preparation Syringes 2-8.

(n) [Non-sterile healthcare practitioner] close centrifuge lid, set timer for 3 minutes, start cycle, and open lid at end of cycle. Dispose of Reagent Syringe-A, Reagent Syringe-B, Tray P-2 and used transfer-hubs (two unused transfer-hubs should still be in Tray P-4).

Step 11: Preparation Phase—Recombine Tissue Concentrate with Adipocytes (a) Remove Adipocyte Syringe-Y from preparation cold-block, hold with syringe-tip up, remove cap, and connect transfer-hub (from Tray P-4).

(b) Remove Preparation Syringe-1 from centrifuge carrier insert and reconnect plunger rod to plunger seal (hold it vertical with syringe-tip down so as not to disturb layers that separate during centrifugation).

(c) Carefully remove cap and connect to transfer-hub on Adipocyte Syringe-Y (maintaining position of Preparation Syringe-1 so as not to disturb layers).

(d) Gently flick tip of Preparation Syringe-1 to break up tissue concentrate which may have adhered to the plastic.

(e) Gently transfer Tissue Concentrate from Preparation Syringe-1 and a minute amount of the liquid from just above it.

(f) Remove Preparation Syringe-1 from transfer-hub and properly dispose of it (with remaining liquid still inside).

(g) Repeat Step 11(b) through 11(f) but transfer Tissue Concentrate from Preparation Syringes 2 into Adipocyte Syringe-Y.

(h) Remove transfer-hub from Adipocyte Syringe-Y, cap it, and place it on work-surface cover.

(i) Remove Adipocyte Syringe-Z from preparation cold-block, hold with syringe tip up, remove cap, and connect transfer-hub.

(j) Repeat Step 11(b) through 11(f) but transfer Tissue Concentrate from Preparation Syringe-3 and Preparation Syringe-4 into Adipocyte Syringe-Z.

(k) Remove transfer-hub from Adipocyte Syringe-Z, cap it, and place it on work-surface cover. When done, Adipocyte Syringe-Y and Adipocyte Syringe-Z will each contain equal amounts of Parenchyma that has not been incubated and (ii) equal amounts of Tissue Concentrate from all Preparation Syringes.

(l) Remove Concentrate Syringe-A from preparation cold-block, remove cap, and connect transfer-hub.

(m) Gently rock Adipocyte Syringe-Y to mix contents, remove cap, and connect it to transfer-hub on Concentrate Syringe-A.

(n) Gently transfer contents of Adipocyte Syringe-Y into Concentrate Syringe-A then back into Adipocyte Syringe-Y.

(o) Remove Adipocyte Syringe-Y from transfer-hub on Concentrate Syringe-A and cap it.

(p) Repeat Step 11(m) through 11(o) but with Adipocyte Syringe-Z.

(q) Dispose of Concentrate Syringe-A.

Step 12: Utilization Phase—Utilize Recombined Tissue Concentrate and Adipocytes (a) Connect transfer-hub to 1 cc syringe (from Tray P-4) or to an alternative syringe provided by physician.

(b) Connect Adipocyte Syringe-Y to transfer-hub on injection syringe then transfer enough prepared adipose tissue to fill 1 cc syringe (or alternative syringe provided by physician).

(c) Remove syringe from transfer-hub on Adipocyte Syringe-Y and attach injection cannula (or an alternative injection cannula of physician's preference).

(d) If physician has clinical assistance, then a second syringe can be attached to Adipocyte Syringe-Y using transfer-hub and an additional portion of prepared adipose tissue in Adipocyte Syringe-Y can be transferred into second syringe.

(e) Prepared adipose tissue in both Adipocyte Syringe-Y and Adipocyte Syringe-Z can be transferred and utilized as determined by physician.

(f) When physician is finished, mark protocol check-list in space provided to indicate current time.

(g) Properly dispose of bio-disposal bag and all remaining 3.0 Tissue Augmentation Kit components and packaging.

(h) Autoclave harvesting cannula, syringe rack, bio-disposal rack, centrifuge carrier inserts, preparation cold-block, and injection cannula. Place preparation cold-block back into refrigeration unit.

What is claimed is:

1. A standardized and optimized, modular, single-use kit for sterile or non-sterile preparation of biological material, the single-use kit comprising:
   at least one modular single-use packaging frame that is a first single-use packaging frame;
   a plurality of modular single-use trays disposed within the first single-use packaging frame, wherein each modular single-use tray of the plurality of modular single-use trays has an identifying label;
   at least one single-use component organized within each modular single-use tray of the plurality of modular single use trays; and
   printed instructions for use comprising a sequence of steps directing use of the single-use kit for the sterile or non-sterile preparation of biological material, wherein one or more of the steps of the instructions corresponds to the identifying label on one or more of the modular single-use trays of the plurality of modular single-use trays,
   wherein the identifying labels of the plurality of modular single-use trays are arranged sequentially, with numbers or letters in ascending or descending order, and one or more steps of the instructions correspond to the sequentially arranged identifying labels, and
   wherein the at least one single-use component of at least one of the plurality of modular single-use trays comprises a plurality of syringes, wherein each syringe of the plurality of syringes comprises a syringe barrel and plunger, wherein the syringe barrel has an inner surface and a syringe-tip with a quick-release connector, wherein the plunger comprises a plunger seal and plunger rod, wherein the plunger rod is used to move the plunger seal along the inner surface of the syringe barrel, and wherein the plunger seal maintains a sterile seal with the inner surface of the plunger barrel or when being moved along the inner surface of the syringe barrel.

2. The kit of claim 1, wherein the plunger rod can be disconnected from and reconnected to the plunger seal while the plunger seal remains in the syringe barrel of each respective syringe, thereby maintaining a sterile seal when the plunger rod is disconnected from the plunger seal.

3. The kit of claim 1, wherein the at least one single-use packaging frame includes a second single-use packaging frame, wherein the second single-use packaging frame has at least one single-use tray disposed therein, wherein the at least one single-use tray of the second single-use packaging frame has at least one single-use component organized therein, and wherein the at least one single-use component of the second single-use packaging frame includes a container containing a liquid to be used with the first single-use packaging frame.

4. The kit of claim 3, wherein the at least one single-use packaging frame includes a third single-use packaging frame having at least one single-use tray disposed therein, wherein the at least one single-use tray of the third single-use packaging frame has at least one single-use component organized therein to be used prior to a patient's procedure in order to prepare aliquots of an enzymatic reagent to be used with the first single-use packaging frame at the time of a patient's procedure.

5. The kit of claim 4, wherein the at least one single-use packaging frame includes a fourth single-use packaging frame having at least one single-use tray disposed therein, wherein the at least one single-use tray has at least one single-use component organized therein, wherein the at least one single-use component of the fourth single use packaging frame includes an enzymatic reagent to be used with the third single-use packaging frame so that the enzymatic reagent can be hydrated and distributed into aliquots to be stored for use with the first single-use packaging frame.

6. The kit of claim 1, wherein the plurality of modular single-use trays of the first single-use packaging frame includes four labeled trays comprising a first labeled tray, a second labeled tray, a third labeled tray, and a fourth labeled tray, wherein:

the first labeled tray is organized with a work area cover, a protocol check-off list, a syringe-rack mat, a bio-disposal bag, and four transfer hubs, and wherein the printed instructions for use include printed instructions for using the first single-use packaging frame, wherein the printed instructions for using the first single-use packaging frame comprise a sequence of eleven steps, wherein the sequence of eleven steps is an operative protocol and is divided into a set-up phase, harvesting phase, preparation phase, and utilization phase, the second labeled tray is organized with four labeled syringes, wherein each of the four labeled syringes has a syringe barrel and a plunger comprising a plunger seal and a detachable plunger rod of a first color, and four syringe-tip caps for the four labeled syringes, wherein the plunger rods of the four labeled syringes can be disconnected from and reconnected to the plunger seals while the plunger seals remain in the syringe barrels of the four labeled syringes, thereby maintaining a sterile seal when the plunger rods are disconnected, the third labeled tray is organized with four labeled syringes, wherein each of the four labeled syringes comprises a syringe barrel and a plunger comprising a plunger seal and a detachable plunger rod of a second color, and four syringe-tip caps for the four labeled syringes, wherein the plunger rods of the four labeled syringes can be disconnected from and reconnected to the plunger seals while the plunger seals remain in the syringe barrels of the four syringes, thereby maintaining a sterile seal when the plunger rods are disconnected, and the fourth labeled tray is organized with a first labeled syringe comprising a syringe barrel and a plunger comprising a plunger seal and a fixed plunger rod of a third color, a second and third labeled syringe, each comprising a syringe barrel and a plunger comprising a plunger seal and a fixed plunger rod of a fourth color, a fourth and fifth labeled syringe, each comprising a syringe barrel and a plunger comprising a plunger seal and a fixed plunger rod of a fifth color, and two transfer-hubs, wherein the work area cover is a peel-back, chevron-type seal and the single packaging frame, labeled trays and single-use components are terminally sterilized after the single packaging frame with labeled trays and single-use components therein is sealed with tamper-evident wrapping, and wherein the at least one single-use component is sterile and the sequence of steps set forth in the printed instructions are for the sterile harvesting, sterile preparation, and sterile utilization of autologous human adipose tissue for implantation or other such therapeutic use or uses.

7. The kit of claim 6, wherein the steps of the operative protocol require the at least one single-use component of the first single-use packaging frame and ancillary equipment including a centrifuge that spins centrifuge-carrier inserts horizontally, a plurality of centrifuge carrier inserts with syringe adapters, an incubating rocker, a preparation cold-block, a syringe rack, a bio-disposal rack, a harvesting cannula, and an injection cannula.

8. The kit of claim 1, wherein the at least one single-use component is sterile and the sequence of steps set forth in the printed instructions are for the sterile harvesting, sterile preparation, and sterile utilization of autologous human adipose tissue for implantation or other such therapeutic use or uses, wherein the at least one single-use packaging frame includes a second single-use packaging frame, wherein the at least one-single-use component and the printed instructions are contained in the first single-use packaging frame and the second single-use packaging frame, wherein the plurality of single-use trays of the first single-use packaging frame comprises:

four labeled trays, including a first labeled tray, a second labeled tray, a third labeled tray, and a fourth labeled tray, wherein:

the first labeled tray is organized with a work area cover, a protocol check-off list, a syringe-rack mat, a bio-disposal bag, vial-to-syringe adapters, and printed instructions for using the first single-use packaging frame, wherein the printed instructions for using the first single-use packaging frame comprise a sequence of eleven steps, wherein the sequence of eleven steps is an operative protocol divided into a set-up phase, harvesting phase, preparation phase, and utilization phase, the second labeled tray is organized with four labeled syringes, wherein each of the four labeled syringes has a syringe barrel and a plunger comprising a plunger seal and a detachable plunger rod of a first color, and four syringe-tip caps for the four labeled syringes, wherein the plunger rods of the four labeled syringes can be disconnected from reconnected to the plunger seals while the plunger seals remain in the syringe barrels of the four labeled syringes, thereby maintaining a sterile seal when the plunger rods are disconnected, the third labeled tray is organized with four labeled syringes, wherein each of the four labeled syringes comprises a syringe barrel and a plunger comprising a plunger seal and a detachable plunger rod of a second color, and four syringe-tip caps for the four labeled syringes, wherein the plunger rods of the four labeled syringes can be disconnected from and reconnected to the plunger seals while the plunger seals remain in the syringe barrels of the four labeled syringes, thereby maintaining a sterile seal when the plunger rods are disconnected, and the fourth labeled tray is organized with a first labeled syringe comprising a syringe barrel and a plunger comprising a plunger seal and a fixed plunger rod of a third color, a second and third labeled syringe each comprising a syringe barrel and a plunger comprising a plunger seal and a fixed plunger rod of a fourth color, a fourth and fifth labeled syringe, each comprising a syringe barrel and a plunger comprising a plunger seal and a fixed plunger rod of a fifth color, and two transfer-hubs, wherein the work area cover is a peel-back, chevron-type seal and the single packaging frame, labeled trays and single-use components are terminally sterilized after the single packaging frame with labeled trays and single-use components therein is sealed with tamper-evident wrapping; and wherein the second single-use packaging frame comprises:

at least one single-use tray disposed therein, wherein the at least one single-use tray of the second single-use packaging frame has at least one single-use component organized therein, wherein the at least one single-use component of the second single-use packaging frame includes a container containing a liquid to be used with the first single-use packaging frame, wherein the container comprises eight vials of sterile saline, and the second single-use packaging frame further includes printed instructions contained within the second single-use packaging frame, wherein the printed instructions are for using the second single-use packaging frame, wherein the at least one single-use component that is sterile is separately packaged in a sterile holder prior to being sealed with tamper-evident wrapping, and wherein the steps of the operative protocol require the at least one single-use component of the first single-use packaging frame and the second single-use packaging frame as well as ancillary equipment including a centrifuge that spins centrifuge-carrier inserts horizontally, a plurality of centrifuge carrier inserts with syringe adapters, an incubating rocker, a preparation cold-block, a syringe rack, a bio-disposal rack, a harvesting cannula, and an injection cannula.

9. The kit of claim 1, wherein the at least one single-use packaging frame includes a second single-use packaging frame, a third single-use packaging frame, and a fourth single-use packaging frame, wherein the at least one single-use component is sterile and the sequence of steps set forth in the printed instructions are for the sterile harvesting, sterile preparation, and sterile utilization of autologous human adipose tissue for implantation or other such therapeutic use or uses, wherein the at least one single-use component and printed instructions are in the first single-use packaging frame, the second single-use packaging frame, the third single-use packaging frame, and the fourth single-use packaging frame, wherein the fourth single-use packaging frame comprises:
a single packaging frame and at least one single-use component organized therein, wherein the at least one single-use component is a container containing an enzymatic reagent to be used with the third single-use packaging frame so that the enzymatic reagent can be hydrated and distributed into aliquots to be stored for use with the first single-use packaging frame, wherein the fourth single-use packaging frame includes two canisters that each contains a vial of sterile, Good Manufacturing Practices-rated, enzymatic reagent in a lyophilized form, twenty hydration vial labels, and the printed instructions are for using the fourth single-use packaging frame, wherein the fourth single-use packaging frame is sealed with tamper-evident wrapping, wherein the third single-use packaging frame comprises a single packaging frame that is disposed with at least one tray organized with at least one single-use component to be used prior to a patient's procedure in order to prepare aliquots of an enzymatic reagent to be used with the first single-use packaging frame at the time of a patient's procedure, wherein the cover on each labeled tray is a peel-back, chevron-type seal and the packaging frame, labeled trays and components are terminally sterilized after the packaging frame with labeled trays and components therein is sealed with tamper-evident wrapping, wherein the first single-use packaging frame comprises:
four labeled trays disposed in the single packaging frame, including a first labeled tray, a second labeled tray, a third labeled tray, and a fourth labeled tray, wherein:

the first labeled tray is organized with a work area cover, a protocol check-off list, a syringe-rack mat, a bio-disposal bag, eleven syringe-to-vial adapters, and printed instructions for using the first single-use packaging frame, wherein the printed instructions for using the first single-use packaging frame comprise a sequence of eleven steps, wherein the sequence of eleven steps is an operative protocol divided into a set-up phase, harvesting phase, preparation phase, and utilization phase, the second labeled tray is organized with four labeled syringes, wherein each of the four labeled syringes has a syringe barrel and a plunger comprising a plunger seal and a detachable plunger rod of a first color, and four syringe-tip caps for the four labeled syringes, wherein the plunger rods of the tour labeled syringes can be disconnected from reconnected to the plunger seals while the plunger seals remain in the syringe barrels of the four labeled syringes, thereby maintaining a sterile seal when the plunger rods are disconnected, the third labeled tray is organized with four labeled syringes, wherein each of the four labeled syringes comprises a syringe barrel and a plunger comprising a plunger seal and a detachable plunger rod of a second color, and four syringe-tip caps for the four labeled syringes, wherein the plunger rods of the four labeled syringes can be disconnected from and reconnected to the plunger seals while the plunger seals remain in the syringe barrels of the four labeled syringes, thereby maintaining a sterile seal when the plunger rods are disconnected, and the fourth labeled tray is organized with a first labeled syringe comprising a syringe barrel and a plunger comprising a plunger seal and a fixed plunger rod of a third color, a second and third labeled syringe, each comprising a syringe barrel and a plunger comprising a plunger seal and a fixed plunger rod of a fourth color, a fourth and fifth labeled syringe, each comprising a syringe barrel and a plunger comprising a plunger seal and a fixed plunger rod of a fifth color, and two transfer-hubs, wherein the work area cover is a peel-back, chevron-type seal and the single packaging frame, labeled trays and single-use components are terminally sterilized after the single packaging frame with labeled trays and singe-use components therein is sealed with tamper-evident wrapping; and wherein the second single-use packaging frame comprises:

at least one single-use tray disposed therein, wherein the at least one single-use tray of the second single-use packaging frame has at least one single-use component organized therein, wherein the at least one single-use component of the second single-use packaging frame includes a container containing a liquid to be used with the first single-use packaging frame, wherein the container comprises eight vials of sterile saline, and the second single-use packaging frame further includes printed instructions contained within the second single-use packaging frame, wherein the printed instructions are for using the second single-use packaging frame, wherein the at least one single-use component that is sterile is separately packaged in a sterile holder prior to being sealed with tamper-evident wrapping.

10. The kit of claim 9, wherein the steps of the operative protocol require at least one single-use component of the first single-use packaging frame and the second single-use packaging frame as well as ancillary equipment including a centrifuge that spins centrifuge-carrier inserts horizontally, a plurality of centrifuge carrier inserts with syringe adapters, an incubating rocker, a preparation cold-block, a syringe rack, bio-disposal rack, a harvesting cannula, and an injection cannula.

11. A standardized and optimized, modular, single-use kit for sterile or non-sterile preparation of biological material, the single-use kit comprising:
at least one modular single-use packaging frame;
a plurality of modular single-use trays disposed within the packaging frame, wherein each single-use tray of the plurality of single-use trays has an identifying label;
at least one single-use component organized within each single-use tray of the plurality of single-use trays disposed within the packaging frame; and
printed instructions for use comprising a sequence of steps directing use of the single-use kit for the sterile or non-sterile preparation of biological material, wherein one or more of the steps of the instructions corresponds to the identifying label on one or more of the plurality of single-use trays disposed within the packaging,
wherein the identifying labels of the plurality of single-use trays are arranged sequentially, with numbers or letters in ascending or descending order, and one or more steps of the instructions correspond to the plurality of sequentially labeled single-use trays,
wherein the at least one single-use component is sterile and the sequence of steps set forth in the instructions are for the sterile harvesting, sterile preparation, and sterile utilization of biological material for implantation or other such therapeutic use or uses,
wherein the biological material is autologous human adipose tissue, and
wherein the single-use packaging frame includes a first single-use packaging frame, wherein the at least one single-use component that is sterile is separately packaged prior to being organized in each labeled tray, and the single packaging frame with the labeled trays and at least one single-use component therein is sealed with tamper-evident wrapping.

12. The kit of claim 11, wherein the steps of the operative protocol require the at least one single-use component of the first single-use packaging frame and ancillary equipment including a centrifuge that spins centrifuge-carrier inserts horizontally, a plurality of centrifuge carrier inserts with syringe adapters, a syringe rack, a bio-disposal rack, a harvesting cannula, and an injection cannula.

13. A method for sterile or non-sterile preparation of biological material, comprising providing a standardized and optimized, modular, single-use kit of claim 1, and carrying out the sequence of steps in the printed instructions directing use of the single-use kit, wherein the sequence of steps set forth in the instructions are for the sterile preparation of biological material, and wherein the sequence of steps comprises:
(1) providing a sterile work area;
(2) providing equipment including a centrifuge;
(3) centrifuging biological material using the centrifuge, resulting in centrifuged biological material;
(4) collecting and setting aside certain portions of the centrifuged biological material;
(5) collecting certain portions of the centrifuged biological material for further preparation;
(6) further preparing certain portions of the biological material; and
(7) combining certain portions of the further-prepared biological material with certain portions of the biological material that was set aside.

14. A method for sterile or non-sterile preparation of biological material, comprising providing a standardized and optimized, modular, single-use kit of claim 1, and carrying out the sequence of steps in the printed instructions directing use of the single-use kit, wherein the sequence of steps set forth in the instructions are for the sterile harvesting, sterile preparation, preservation and storage of biological material, and wherein the sequence of steps comprises:
(1) providing a sterile work area;
(2) providing equipment including a centrifuge;
(3) harvesting the biological material from a patient;
(4) centrifuging the biological material using the centrifuge, resulting in centrifuged biological material;
(5) collecting and setting aside certain portions of the centrifuged biological material;
(6) collecting certain portions of the centrifuged biological material for further preparation;
(7) further preparing certain portions of the centrifuged biological material;
(8) combining certain portions of the further-prepared biological material with certain portions of the centrifuged biological material that was set aside;
(9) preparing the combined biological material for storage; and
(10) packaging and shipping the combined biological material to be stored.

15. A method for sterile or non-sterile preparation of biological material, comprising providing a standardized and optimized, modular, single-use kit of claim 1, and carrying out the sequence of steps in the printed instructions directing use of the single-use kit, wherein the sequence of steps set forth in the instructions for sterile harvesting, sterile preparation, and sterile utilization of biological material for non-autologous implantation or other therapeutic use, and wherein the sequence of steps comprises:
(1) providing a sterile work area;
(2) providing equipment including a centrifuge;
(3) harvesting the biological material from a donor patient;
(4) centrifuging the biological material using the centrifuge, resulting in centrifuged biological material;
(5) collecting and setting aside certain portions of the centrifuged biological material;
(6) collecting certain portions of the centrifuged biological material for further preparation;
(7) further preparing certain portions of the centrifuged biological material;
(8) combining certain portions of the further-prepared biological material with certain portions of the centrifuged biological material that was set aside; and
(9) temporarily storing the combined biological material to be used in a patient other than the donor patient.

16. A method for sterile or non-sterile preparation of biological material, comprising providing a standardized and optimized, modular, single-use kit of claim 1, and carrying out the sequence of steps in the printed instructions directing use of the single-use kit, wherein the sequence of steps set forth in the instructions are for the non-autologous sterile harvesting, sterile preparation, identification, isolation, and use of stem cells, and wherein the sequence of steps comprises:
(1) providing a sterile work area;
(2) providing equipment including a centrifuge;
(3) harvesting the biological material from a donor patient;
(4) centrifuging the biological material using the centrifuge, resulting in centrifuged biological material;
(5) collecting certain portions of the centrifuged biological material for further preparation;
(6) further preparing certain portions of the biological material;
(7) analyzing the prepared biological material to identify and isolate stem cells; and
(8) using the stem cells to treat a patient other than the donor patient.

17. A method for sterile or non-sterile preparation of biological material, comprising providing a standardized and optimized, modular, single-use kit of claim 1, and carrying out the sequence of steps in the printed instructions directing use of the single-use kit, wherein the sequence of steps set forth in the instructions a for the non-autologous sterile harvesting, sterile preparation, identification, isolation, differentiation, and use of stem cells, and wherein the sequence of steps comprises:
(1) providing a sterile work area;
(2) providing equipment including a centrifuge;
(3) harvesting the biological material from a donor patient;
(4) centrifuging the biological material using the centrifuge, resulting in centrifuged biological material;
(5) collecting certain portions of the centrifuged biological material for further preparation;
(6) further preparing certain portion of the biological material;
(7) analyzing the prepared biological material to identify, isolate and differentiate certain stem cells; and
(8) temporarily storing the differentiated stem cells to be used in a patient other than the donor patent.

18. A method for sterile or non-sterile preparation of biological material, comprising providing a standardized and optimized, modular, single-use kit of claim 1, and carrying out the sequence of step in the printed instructions directing use of the single-use kit, wherein the sequence of steps set forth in the instructions are for the autologous sterile harvesting, sterile preparation, identification, isolation, differentiation, and use of stem cells, and wherein the sequence of steps comprises:
(1) providing a sterile work area;
(2) providing equipment including a centrifuge;
(3) harvesting the biological material from a donor patent;
(4) centrifuging the biological material using the centrifuge, resulting in centrifuged biological material;
(5) collecting certain portions of the biological material for further preparation;
(6) further preparing certain portions of the biological material;
(7) analyzing the prepared biological material to identify, isolate and differentiate certain stem cells; and
(8) using the differentiated stem cells to treat the donor patient.

19. A method for sterile or non-sterile preparation of biological material, comprising providing a standardized and optimized, modular, single-use kit of claim 1, and carrying out the sequence of steps in the printed instructions directing use of the single-use kit, wherein the sequence of steps comprises:
(1) providing a sterile work area;
(2) providing equipment including a centrifuge;
(3) harvesting adipose tissue from an access site or sites on a patient;
(4) centrifuging the harvested adipose tissue using the centrifuge;
(5) transferring post-centrifugation layers wherein the post-centrifugation layers include a tissue concentrate and adipocytes;
(6) combining the tissue concentrate and adipocytes of the transferred post-centrifugation layers; and
(7) utilizing the combined tissue concentrate and adipocytes.

* * * * *

UNITED STATES PATENT AND TRADEMARK OFFICE
CERTIFICATE OF CORRECTION

PATENT NO.         : 9,988,599 B2
APPLICATION NO.    : 15/505731
DATED              : June 5, 2018
INVENTOR(S)        : Gregory G. Bendis et al.

Page 1 of 1

It is certified that error appears in the above-identified patent and that said Letters Patent is hereby corrected as shown below:

In the Specification

Column 1,
Line 9, "PCT/US15/046759" should read --PCT/US2015/046759--.

In the Claims

Column 86,
Line 62, "(8) temporarily" should read --(9) temporarily--.

Signed and Sealed this
Second Day of April, 2019

Andrei Iancu
*Director of the United States Patent and Trademark Office*